US012649980B2

(12) United States Patent
Liu et al.

(10) Patent No.: US 12,649,980 B2
(45) Date of Patent: Jun. 9, 2026

(54) THREE-DIMENSIONAL SURFACE FOR PROTEIN AND SMALL MOLECULE MICROARRAYS

(71) Applicant: The Johns Hopkins University, Baltimore, MD (US)

(72) Inventors: Jun O. Liu, Baltimore, MD (US); Zhiqiang Cheng, Baltimore, MD (US); Heng Zhu, Baltimore, MD (US); Zufeng Guo, Baltimore, MD (US); Hanjing Peng, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 917 days.

(21) Appl. No.: 17/766,570

(22) PCT Filed: Oct. 7, 2020

(86) PCT No.: PCT/US2020/054555
§ 371 (c)(1),
(2) Date: Apr. 5, 2022

(87) PCT Pub. No.: WO2021/071931
PCT Pub. Date: Apr. 15, 2021

(65) Prior Publication Data

US 2024/0024410 A1 Jan. 25, 2024

Related U.S. Application Data

(60) Provisional application No. 62/911,702, filed on Oct. 7, 2019.

(51) Int. Cl.
*C40B 40/10* (2006.01)
*G01N 33/68* (2006.01)

(52) U.S. Cl.
CPC ......... *C40B 40/10* (2013.01); *G01N 33/6845* (2013.01)

(58) Field of Classification Search
None
See application file for complete search history.

(56) References Cited

U.S. PATENT DOCUMENTS 7,846,746 B2 12/2010 Nollau et al.
9,522,971 B2 12/2016 Chang et al.
2012/0021933 A1 1/2012 Park et al.
(Continued)

FOREIGN PATENT DOCUMENTS

WO WO 2010/004304 1/2010
WO WO 2014/201405 12/2014
WO WO 2017/136708 8/2017

OTHER PUBLICATIONS

Chao, Clinical Diabetes, vol. 32, No. 1, pp. 4-1 (Year: 2014).*
(Continued)

*Primary Examiner* — Christian C Boesen
(74) *Attorney, Agent, or Firm* — Casimir Jones, S.C.; Robert A. Goetz

(57) ABSTRACT

Surface structures that enable the preparation of three-dimensional microarrays of proteins or small molecules or other types of macromolecules are disclosed. The three-dimensional microarrays possess higher sensitivity for detecting protein-macromolecule and small molecule-protein interactions in a high-throughput fashion.

5 Claims, 51 Drawing Sheets

(56) References Cited

U.S. PATENT DOCUMENTS

2014/0073581 A1 3/2014 Liu et al.
2019/0092808 A1 3/2019 Liu et al.

OTHER PUBLICATIONS

Li et al. (2011) Tetrahedron Letters vol. 52 pp. 5070 to 5072 (Year: 2011).*
Giese et al. (2016) Analytical Chemistry vol. 88 pp. 8239 to 8247 (Year: 2016).*
Barbey et al., Polymer brushes via surface-initiated controlled radical polymerization: synthesis, characterization, properties, and applications. Chem Rev. Nov. 2009;109(11):5437-527.
Barbey et al., Protein microarrays based on polymer brushes prepared via surface-initiated atom transfer radical polymerization. Biomacromolecules. Dec. 13, 2010;11(12):3467-79.
Bierer et al., Two distinct signal transmission pathways in T lymphocytes are inhibited by complexes formed between an immunophilin and either FK506 or rapamycin. Proc Natl Acad Sci U S A. Dec. 1990;87(23):9231-5.
Cao et al., Glucose uptake inhibitor sensitizes cancer cells to daunorubicin and overcomes drug resistance in hypoxia. Cancer Chemother Pharmacol. Mar. 2007;59(4):495-505.
Chan et al., Targeting GLUT1 and the Warburg effect in renal cell carcinoma by chemical synthetic lethality. Sci Transl Med. Aug. 3, 2011;3(94):94ra70.
Chen et al., Regulation of glut1 mRNA by hypoxia-inducible factor-1. Interaction between H-ras and hypoxia. J Biol Chem. Mar. 23, 2001;276(12):9519-25.
Debosch et al., Trehalose inhibits solute carrier 2A (SLC2A) proteins to induce autophagy and prevent hepatic steatosis. Sci Signal. Feb. 23, 2016;9(416):ra21.
Foong et al., Current advances in peptide and small molecule microarray technologies. Curr Opin Chem Biol. Apr. 2012;16(1-2):234-42.
Griffith et al., X-ray structure of calcineurin inhibited by the immunophilin-immunosuppressant FKBP12-FK506 complex. Cell. Aug. 11, 1995;82(3):507-22.
Gunnink et al., Curcumin directly inhibits the transport activity of GLUT1. Biochimie. Jun. 2016;125:179-85.
Guo et al., Rapamycin-inspired macrocycles with new target specificity. Nat Chem. Mar. 2019;11(3):254-263.
Hay. Reprogramming glucose metabolism in cancer: can it be exploited for cancer therapy? Nat Rev Cancer. Oct. 2016;16(10):635-49.
Head et al., Simultaneous Targeting of NPC1 and VDAC1 by Itraconazole Leads to Synergistic Inhibition of mTOR Signaling and Angiogenesis. ACS Chem Biol. Jan. 20, 2017;12(1):174-182.
Heitman et al., Targets for cell cycle arrest by the immunosuppressant rapamycin in yeast. Science. Aug. 23, 1991;253(5022):905-9.
Helgerson et al., Equilibrium ligand binding to the human erythrocyte sugar transporter. Evidence for two sugar-binding sites per carrier. J Biol Chem. Apr. 25, 1987;262(12):5464-75.
Hellwig et al., Differentiation of erythrocyte-(GLUT1), liver-(GLUT2), and adipocyte-type (GLUT4) glucose transporters by binding of the inhibitory ligands cytochalasin B, forskolin, dipyridamole, and isobutylmethylxanthine. Mol Pharmacol. Sep. 1991;40(3):383-9.
Hong et al., Ligation of intersphincteric fistula tract (LIFT) to treat anal fistula: systematic review and meta-analysis. Tech Coloproctol. Aug. 2014;18(8):685-91.
Hong et al., Recent discoveries and applications involving small-molecule microarrays. Curr Opin Chem Biol. Feb. 2014;18:21-8.
International Search Report and Written Opinion for PCT/US20/54555. Mailed Jan. 12, 2021. 12 pages.
Jones et al., Tumor suppressors and cell metabolism: a recipe for cancer growth. Genes Dev. Mar. 1, 2009;23(5):537-48.
Kanoh et al., Immobilization of natural products on glass slides by using a photoaffinity reaction and the detection of protein-small-molecule interactions. Angew Chem Int Ed Engl. Nov. 24, 2003;42(45):5584-7.
Kanoh et al., Immobilization of natural products on glass slides by using a photoaffinity reaction and the detection of protein-small-molecule interactions. Angew. Chem. 2003, 115, 5742-5745.
Kapoor et al., Mechanism of inhibition of human glucose transporter GLUT1 is conserved between cytochalasin B and phenylalanine amides. Proc Natl Acad Sci U S A. Apr. 26, 2016;113(17):4711-6.
Kawatani et al., Affinity-based target identification for bioactive small molecules. Medchemcomm 2014, 5(3), 277-287.
Kissinger et al., Crystal structures of human calcineurin and the human FKBP12-FK506-calcineurin complex. Nature. Dec. 7, 1995;378(6557):641-4.
Lee et al., Permanent, nonleaching antibacterial surfaces. 1. Synthesis by atom transfer radical polymerization. Biomacromolecules. May-Jun. 2004;5(3):877-82.
Liu et al., A small-molecule inhibitor of glucose transporter 1 downregulates glycolysis, induces cell-cycle arrest, and inhibits cancer cell growth in vitro and in vivo. Mol Cancer Ther. Aug. 2012;11(8):1672-82.
Liu et al., Calcineurin is a common target of cyclophilin-cyclosporin A and FKBP-FK506 complexes. Cell. Aug. 23, 1991;66(4):807-15.
Liu et al., Development and quantitative evaluation of a high-resolution metabolomics technology. Anal Chem. Feb. 18, 2014;86(4):2175-84.
Ma et al., Surface initiated polymerization from substrates of low initiator density and its applications in biosensors. ACS Appl Mater Interfaces. Nov. 2010;2(11):3223-30.
Marinec et al., FK506-binding protein (FKBP) partitions a modified HIV protease inhibitor into blood cells and prolongs its lifetime in vivo. Proc Natl Acad Sci U S A. Feb. 3, 2009;106(5):1336-41.
Melstrom et al., Apigenin inhibits the GLUT-1 glucose transporter and the phosphoinositide 3-kinase/Akt pathway in human pancreatic cancer cells. Pancreas. Nov. 2008;37(4):426-31.
Miyazaki et al., A small-molecule inhibitor shows that pirin regulates migration of melanoma cells. Nat Chem Biol. Sep. 2010;6(9):667-73.
Mueckler et al., The SLC2 (GLUT) family of membrane transporters. Mol Aspects Med. Apr.-Jun. 2013;34(2-3):121-38.
Schwartzenberg-Bar-Yoseph et al., The tumor suppressor p53 down-regulates glucose transporters GLUT1 and GLUT4 gene expression. Cancer Res. Apr. 1, 2004;64(7):2627-33.
Siebeneicher et al., Identification and Optimization of the First Highly Selective GLUT1 Inhibitor BAY-876. ChemMedChem. Oct. 19, 2016;11(20):2261-2271.
Ulanovskaya et al., A pairwise chemical genetic screen identifies new inhibitors of glucose transport. Chem Biol. Feb. 25, 2011;18(2):222-30.
Uttamchandani et al., The Expanding World of Small Molecule Microarrays. Methods Mol Biol. 2017;1518:1-17.
Vera et al., Genistein is a natural inhibitor of hexose and dehydroascorbic acid transport through the glucose transporter, GLUT1. J Biol Chem. Apr. 12, 1996;271(15):8719-24.
Warburg, On Respiratory Impairment in Cancer Cells. Science 1956, 124, 267-272.
Wood et al., A novel inhibitor of glucose uptake sensitizes cells to FAS-induced cell death. Mol Cancer Ther. Nov. 2008;7(11):3546-55.
Yamada et al., Binding of ethacrynic acid to hepatic glutathione S-transferases in vivo in the rat. Biochem Pharmacol. Apr. 15, 1980;29(8):1205-8.
Yang et al., mTOR kinase structure, mechanism and regulation. Nature. May 9, 2013;497(7448):217-23.
Yun et al., Glucose deprivation contributes to the development of KRAS pathway mutations in tumor cells. Science. Sep. 18, 2009;325(5947):1555-9.
Zhang et al., Novel inhibitors of basal glucose transport as potential anticancer agents. Bioorg Med Chem Lett. Apr. 1, 2010;20(7):2191-4.

(56) References Cited

OTHER PUBLICATIONS

Zhang et al., Pyridinylquinazolines selectively inhibit human methionine aminopeptidase-1 in cells. J Med Chem. May 23, 2013;56(10):3996-4016.

Zoppe et al., Surface-Initiated Controlled Radical Polymerization: State-of-the-Art, Opportunities, and Challenges in Surface and Interface Engineering with Polymer Brushes. Chem Rev. Feb. 8, 2017;117(3):1105-1318.

* cited by examiner a b

JW11-D2
Rapaglutin (RgA)

HP17-C2

| | Human red blood cells | Erythrocyte membranes |
|---|---|---|
| $IC_{50}$ (nM) | 34.2±2.6 | 49.5±5.3 |

a

Biotin-RgA b

| | Jurkat T WT | Jurkat T FKBP12 KO | Jurkat T FKBP51 KO | Jurkat T FKBP52 KO |
|---|---|---|---|---|
| $IC_{50}$ (nM) | 15.3±1.6 | 16.4±1.3 | 18.3±2.2 | 22.0±1.9 |

a

FKBD10

FKBD11

FKBD12

FKBD13

FKBD14

The spot:
FKBP12:FK506

FKBP12:rapamycin

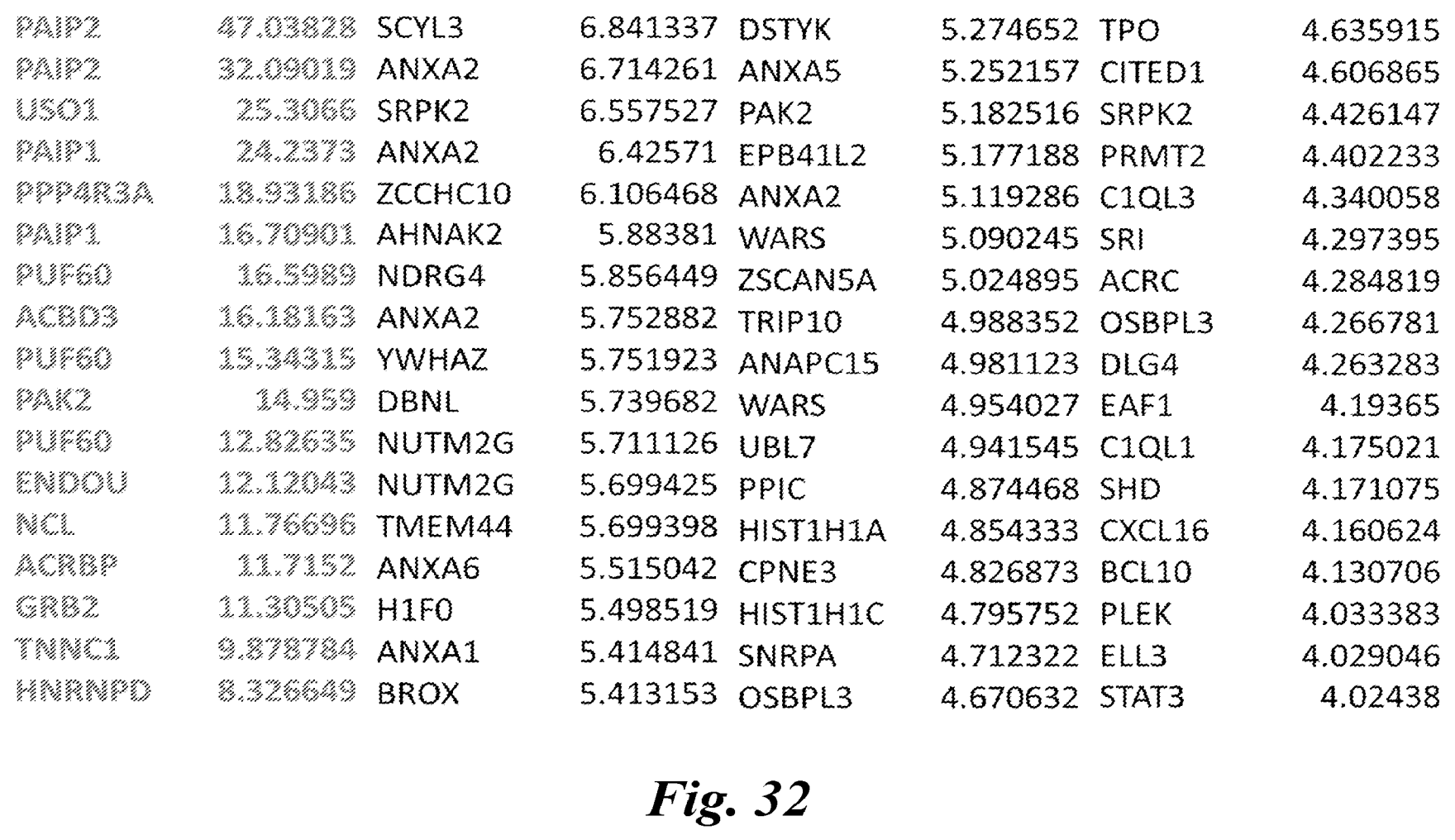

| | | | | | | | |
|---|---|---|---|---|---|---|---|
| PAIP2 | 47.03828 | SCYL3 | 6.841337 | DSTYK | 5.274652 | TPO | 4.635915 |
| PAIP2 | 32.09019 | ANXA2 | 6.714261 | ANXA5 | 5.252157 | CITED1 | 4.606865 |
| USO1 | 25.3066 | SRPK2 | 6.557527 | PAK2 | 5.182516 | SRPK2 | 4.426147 |
| PAIP1 | 24.2373 | ANXA2 | 6.42571 | EPB41L2 | 5.177188 | PRMT2 | 4.402233 |
| PPP4R3A | 18.93186 | ZCCHC10 | 6.106468 | ANXA2 | 5.119286 | C1QL3 | 4.340058 |
| PAIP1 | 16.70901 | AHNAK2 | 5.88381 | WARS | 5.090245 | SRI | 4.297395 |
| PUF60 | 16.5989 | NDRG4 | 5.856449 | ZSCAN5A | 5.024895 | ACRC | 4.284819 |
| ACBD3 | 16.18163 | ANXA2 | 5.752882 | TRIP10 | 4.988352 | OSBPL3 | 4.266781 |
| PUF60 | 15.34315 | YWHAZ | 5.751923 | ANAPC15 | 4.981123 | DLG4 | 4.263283 |
| PAK2 | 14.959 | DBNL | 5.739682 | WARS | 4.954027 | EAF1 | 4.19365 |
| PUF60 | 12.82635 | NUTM2G | 5.711126 | UBL7 | 4.941545 | C1QL1 | 4.175021 |
| ENDOU | 12.12043 | NUTM2G | 5.699425 | PPIC | 4.874468 | SHD | 4.171075 |
| NCL | 11.76696 | TMEM44 | 5.699398 | HIST1H1A | 4.854333 | CXCL16 | 4.160624 |
| ACRBP | 11.7152 | ANXA6 | 5.515042 | CPNE3 | 4.826873 | BCL10 | 4.130706 |
| GRB2 | 11.30505 | H1F0 | 5.498519 | HIST1H1C | 4.795752 | PLEK | 4.033383 |
| TNNC1 | 9.878784 | ANXA1 | 5.414841 | SNRPA | 4.712322 | ELL3 | 4.029046 |
| HNRNPD | 8.326649 | BROX | 5.413153 | OSBPL3 | 4.670632 | STAT3 | 4.02438 |

*Fig. 32*

THREE-DIMENSIONAL SURFACE FOR PROTEIN AND SMALL MOLECULE MICROARRAYS

FEDERALLY SPONSORED RESEARCH OR DEVELOPMENT

This invention was made with government support under grant CA174428 awarded by the National Institutes of Health. The government has certain rights in the invention.

BACKGROUND

Glucose is a universal cellular fuel that serves as both an energy source and building blocks for a variety of macromolecules. In comparison to normal cells, cancer cells have a higher demand for glucose due to their faster proliferation rate and aerobic glycolysis as a consequence of the Warburg effect. Warburg, *Science* 1956, 124, 267-272. Several common cancer driver mutations, such as p53 and KRAS, as well as hypoxia, have been shown to upregulate the expression of glucose transporters, prominent among which are members of the facilitative glucose transporter family, including GLUT1 and GLUT3. Hay, *Nat. Rev. Cancer* 2016, 16, 635-649; Schwartzenberg-Bar-Yoseph, et al., *Cancer Res.* 2004, 64, 2627-2633; Jun et al., *Science,* 2009, 325, 1555-1559; and Chen, et al., *J. Biol. Chem.* 2001, 276, 9519-9525.

Inhibition of GLUTs has been shown to not only block cancer cell growth, but also can sensitize cancer cells to other drugs. Cao, et al., *Cancer Chemother. Pharmacol.* 2007, 59, 495-505; Liu, et al., *Mol. Cancer Ther.* 2012, 11, 1672-1682. Extensive efforts have been made to discover new inhibitors of GLUTs, particularly GLUT1, as leads for developing novel anticancer drugs. Liu, et al., *Mol. Cancer Ther.* 2012, 11, 1672-1682; Chan, et al., *Sci. Transl. Med.* 2011, 3, 94ra70; Zhang, et al., *Bioorg. Med. Chem. Lett.* 2010, 20, 2191-2194; Gunnink, et al., *Biochimie* 2016, 125, 179-185; Wood, et al., *Mol. Cancer Ther.* 2008, 7, 3546-3555; Melstrom, et al., *Pancreas* 2008, 37, 426-431; Vera, et al, *J. Biol. Chem.* 1996, 271, 8719-8724; Ulanovskaya, et al., *Chem. Biol.* 2011, 18, 222-230; Kapoor, et al., *Proc. Natl. Acad. Sci. USA* 2016, 113, 4711-4716; DeBosch, et al., *Sci. Signal* 2016, 9, ra21; and Siebeneicher, et al., *ChemMedChem* 2016, 11, 2261-2271. Although a number of GLUT inhibitors have been reported, including BAY-876, Siebeneicher, et al., *ChemMedChem* 2016, 11, 2261-2271, a potent and isoform-specific GLUT1 inhibitor, none has entered the clinic to date.

SUMMARY

In some aspects, the presently disclosed subject matter provides a three-dimensional microarray comprising a surface-modified substrate having one or more polymer chains attached thereto, wherein the one or more polymers chains have one or more diazirine functional groups bound thereto, and wherein the one or more diazirine functional groups have one or more rapafucins covalently bound thereto.

In some aspects, the three-dimensional microarray comprises a surface-modified substrate comprises a scaffold having the following molecular structure:

In some aspects, the presently disclosed subject matter provides a three-dimensional array, wherein the surface-modified substrate comprises a scaffold having the following molecular structure:

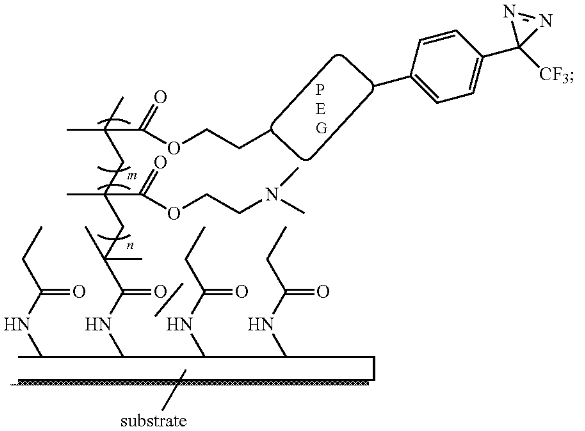

wherein m and n are each independently an integer from 1 to 1000.

In certain aspects, the presently disclosed three-dimensional array further comprises a library of small molecules printed on one or more locations on the surface, wherein the library of small molecules are immobilized to the surface through photocrosslinking to the diazirine functional groups.

In other aspects, the presently disclosed subject matter provides a method of generating a three-dimensional microarray comprising a library of small molecules, the method comprising:

- providing a surface-modified substrate having one or more polymer chains attached thereto, wherein the one or more polymers chains have one or more diazirine functional groups bound thereto;
- providing a library of small molecules in a solvent carrier;
- printing the library of small molecules in the solvent carrier onto the surface;
- evaporating substantially all of the solvent carrier from the surface; and
- exposing the printed library of small molecules to UV light of an appropriate wavelength to cause crosslinking of the small molecules to the surface through photoactivation of the one or more diazirine functional groups into one or more reactive carbene species.

In yet other aspects, the presently disclosed subject matter provides a method of screening the presently disclosed three-dimensional microarray, the method comprising:

- exposing the three-dimensional microarray to a cell lysate expressing a protein of interest (POI) or purified recombinant POI;
- washing the three-dimensional microarray to remove unbound protein; and
- detecting a POI bound to a specific small molecule by using a fluorescently labeled primary antibody against the POI or a tag that is fused to the POI, wherein the specific small molecule bound to the POI is identified by a predetermined location of the specific small molecule.

In yet other aspects, the presently disclosed subject matter provides a three-dimensional array comprising a surface-modified substrate having one or more polymer chains attached thereto, wherein the one or more polymer chains have one or more ethacrynic acid (EA) moieties bound thereto.

In particular aspects of the presently disclosed three-dimensional array, the scaffold has the following molecular structure:

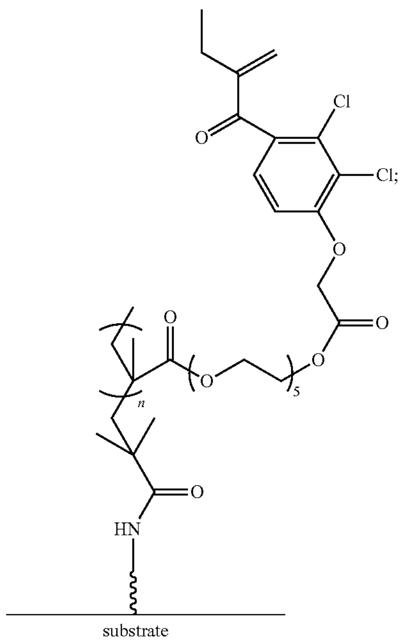

wherein n is an integer from 1 to 1000.

In certain aspects, the three-dimensional microarray further comprises a library of human proteome printed thereon, wherein each protein of the human proteome is fused to glutathione S-transferase (GST) through interaction of GST with the one or more ethacrynic acid moieties bound to the one or more polymer chains.

In other aspects, the three-dimensional protein microarray further comprises a covalent protein-ligand pair comprising a covalent bond between an immobilized small molecule ligand and the corresponding fusion tag of a protein of interest (POI), wherein the fusion tag is selected from a haloTag, a SNAP-tag, and a CLIP-tab.

In other aspects, the presently disclosed subject matter provides a method of screening the EA three-dimensional microarray for new protein-protein, protein-nucleic acid and protein-small molecule interactions, the method comprising contacting the three-dimensional microarray with one or more proteins, nucleic acids, or small molecules of interest.

In yet other aspects, the presently disclosed subject matter provides a method for identifying a glucose transporter inhibitor, the method comprising contacting a presently disclosed three-dimensional microarray(s) with one or more cells expressing a glucose transporter protein, wherein the glucose transporter protein binds to one or more rapafucins of the three-dimensional microarray, and detecting the bound glucose transporter protein.

In certain aspects, the glucose transporter protein is selected from GLUT1, GLUT3, and GLUT4. In more certain aspects, the glucose transporter protein is GLUT1.

In other aspects, the presently disclosed subject matter provides a glucose transporter inhibitor identified by the presently disclosed methods.

In yet other aspects, the presently disclosed subject matter provides a method for treating a disease, condition, or disorder associated with one or more glucose transporters, the method comprising administering to a subject in need of treatment thereof a therapeutically effective amount of a glucose transporter inhibitor or a pharmaceutically effective salt thereof.

In particular aspects, the disease, disorder, or condition is a cancer. In more particular aspects, the cancer is breast cancer.

Certain aspects of the presently disclosed subject matter having been stated hereinabove, which are addressed in whole or in part by the presently disclosed subject matter, other aspects will become evident as the description proceeds when taken in connection with the accompanying Examples and Drawings as best described herein below.

BRIEF DESCRIPTION OF THE DRAWINGS

Figure 1:
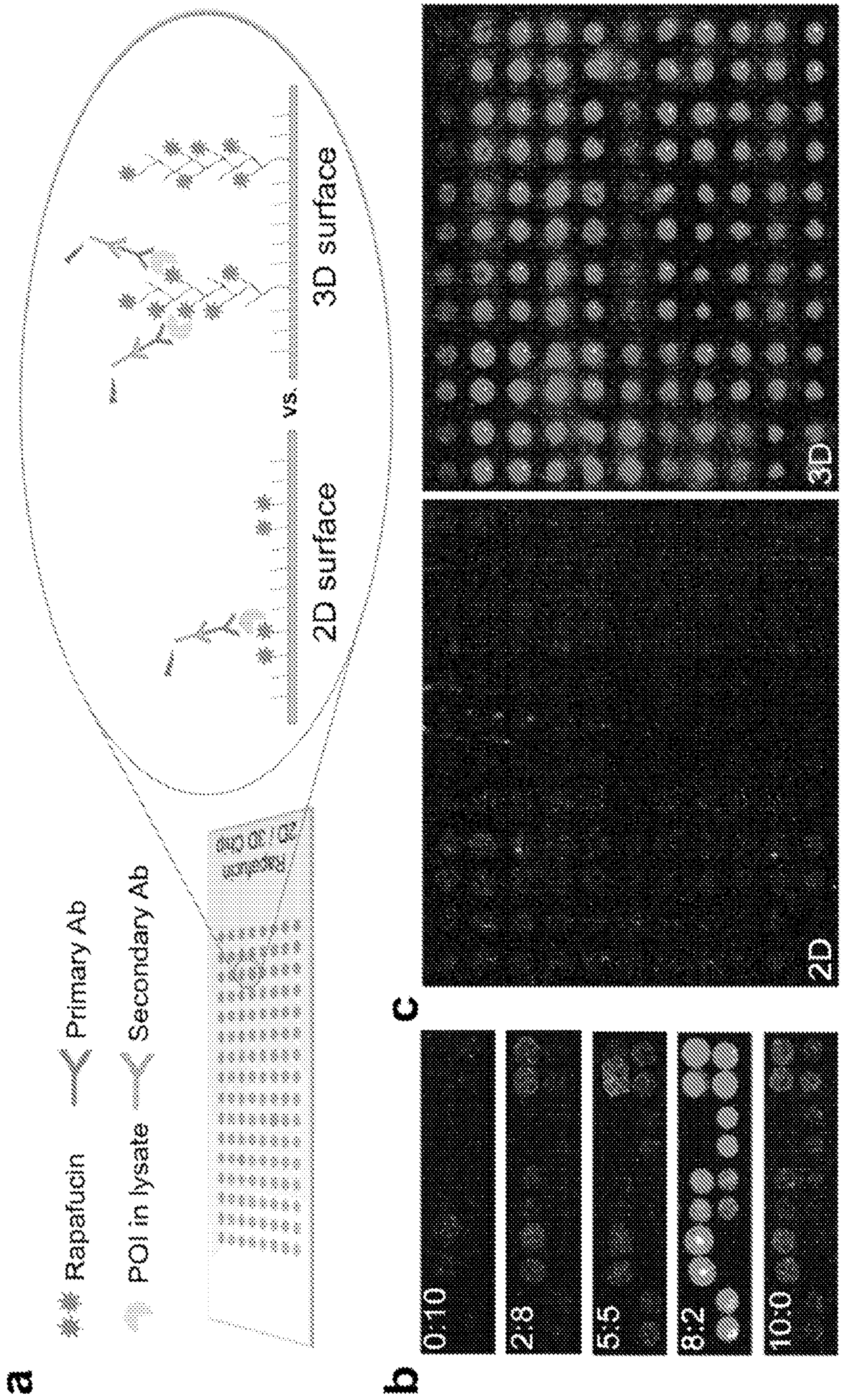
Figure 4:
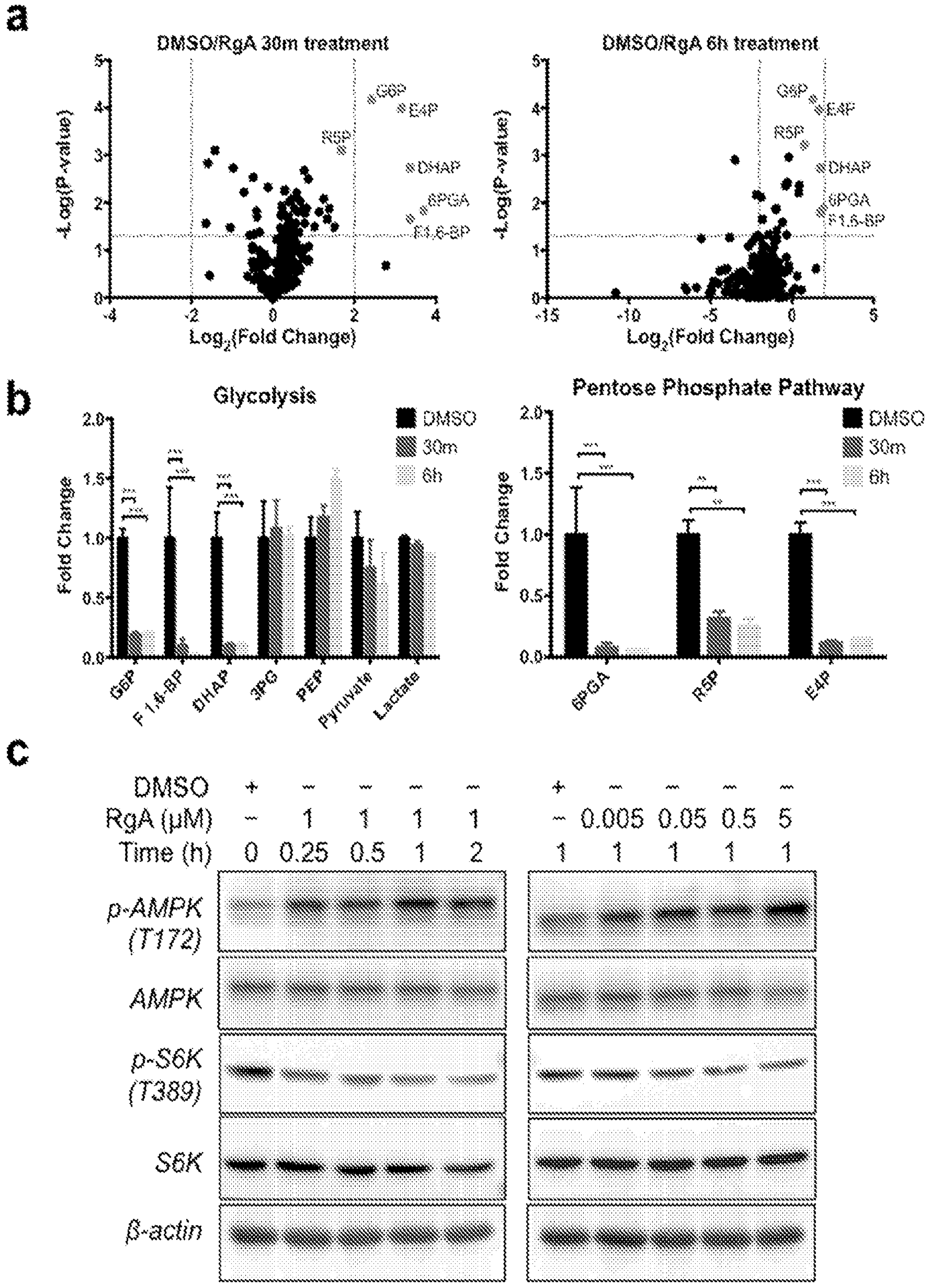
Figure 6:
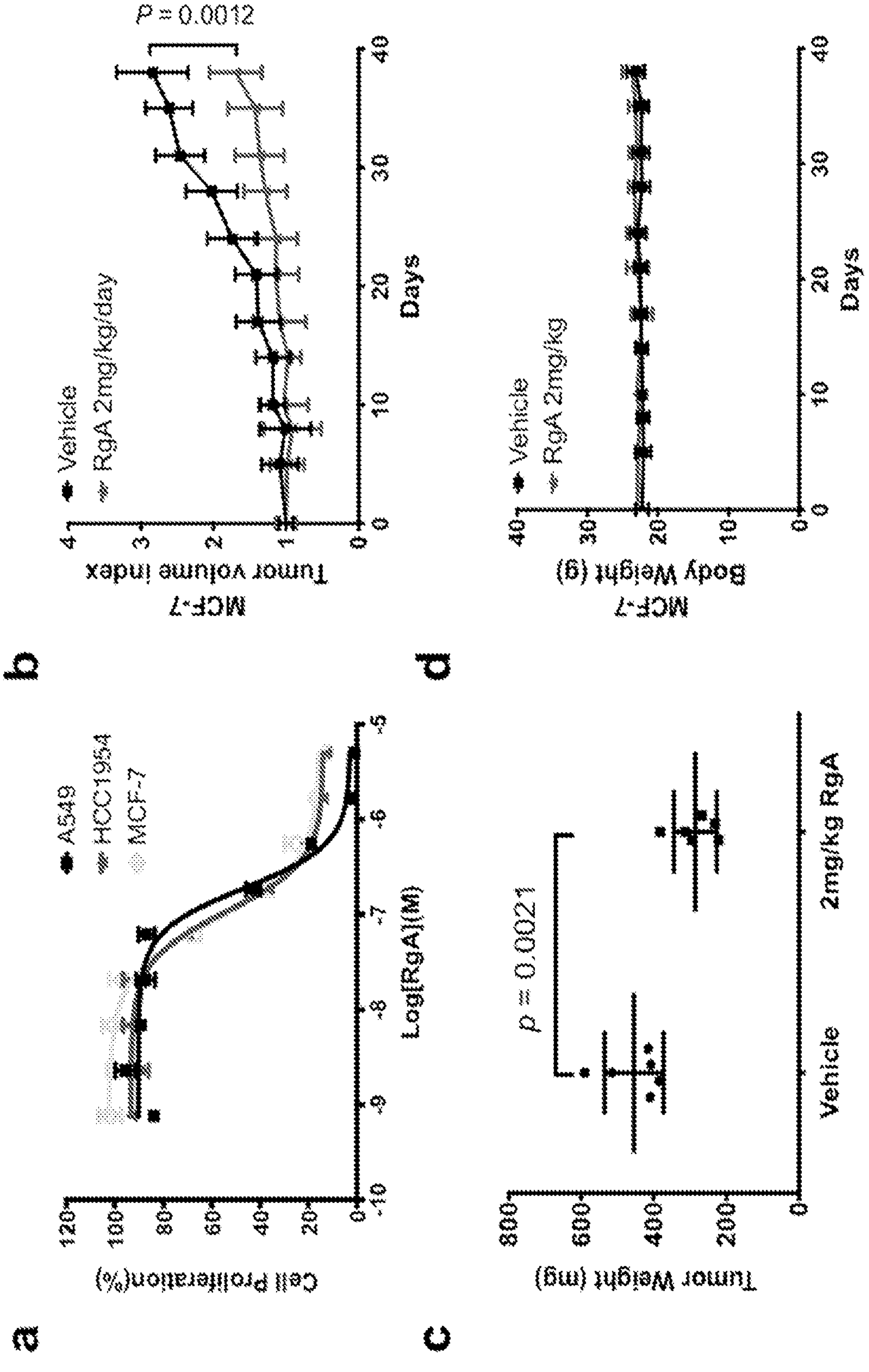
Figure 7:
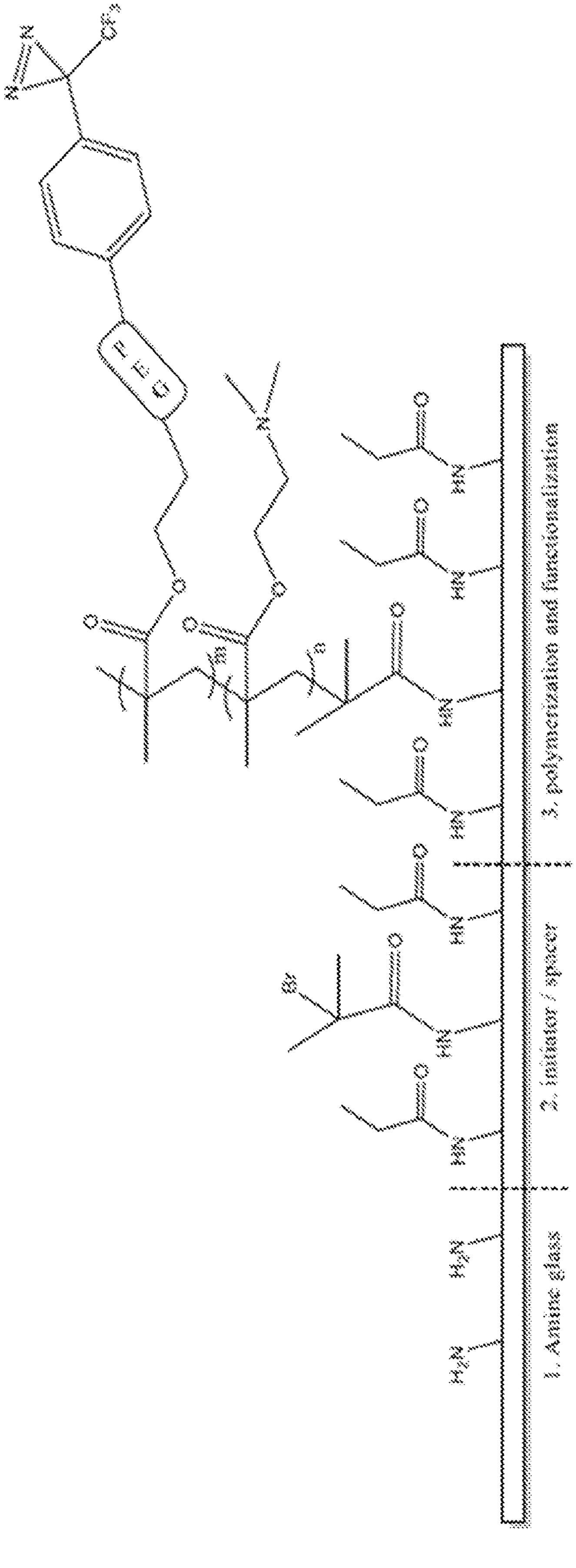
Figure 8:
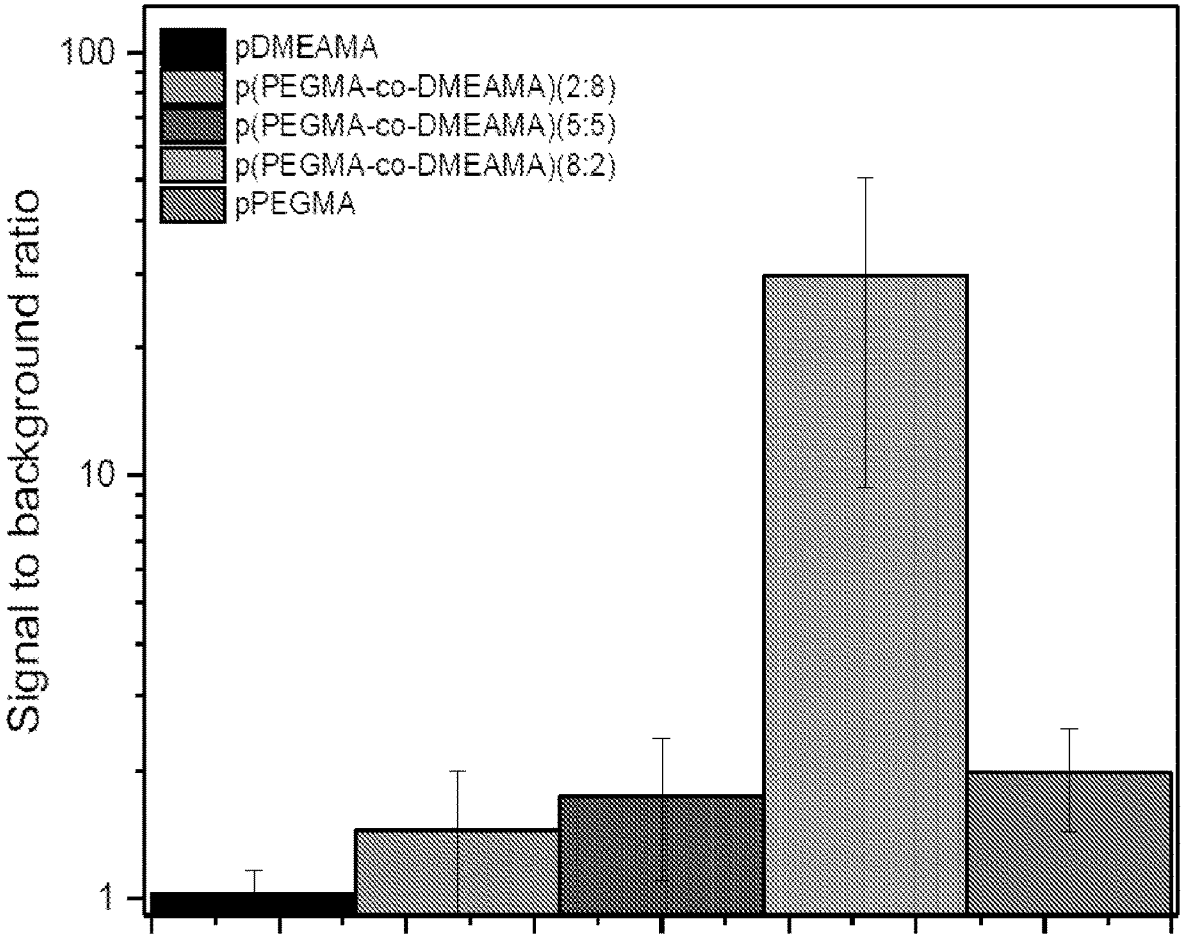
Figure 9:
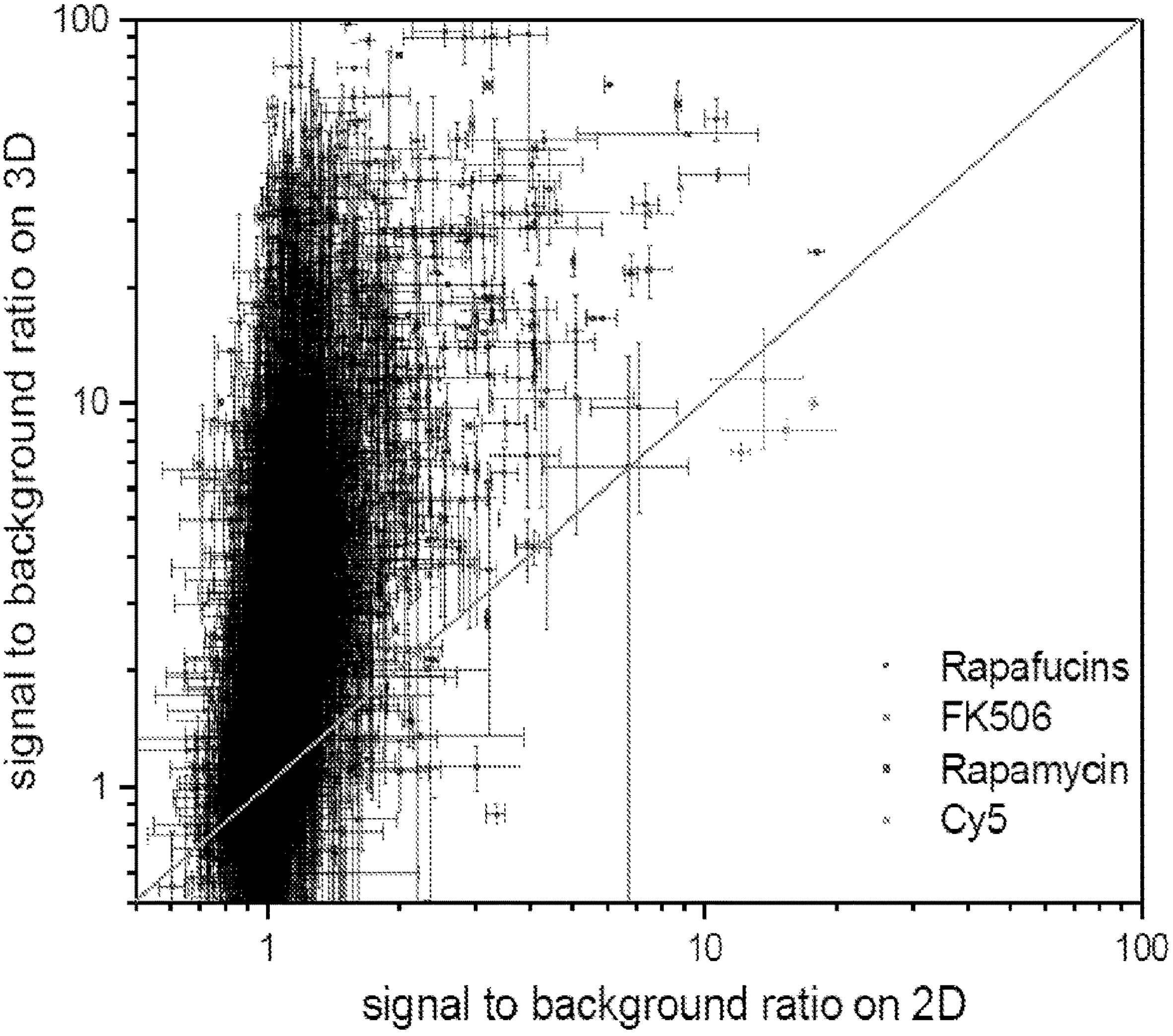
Figure 10:
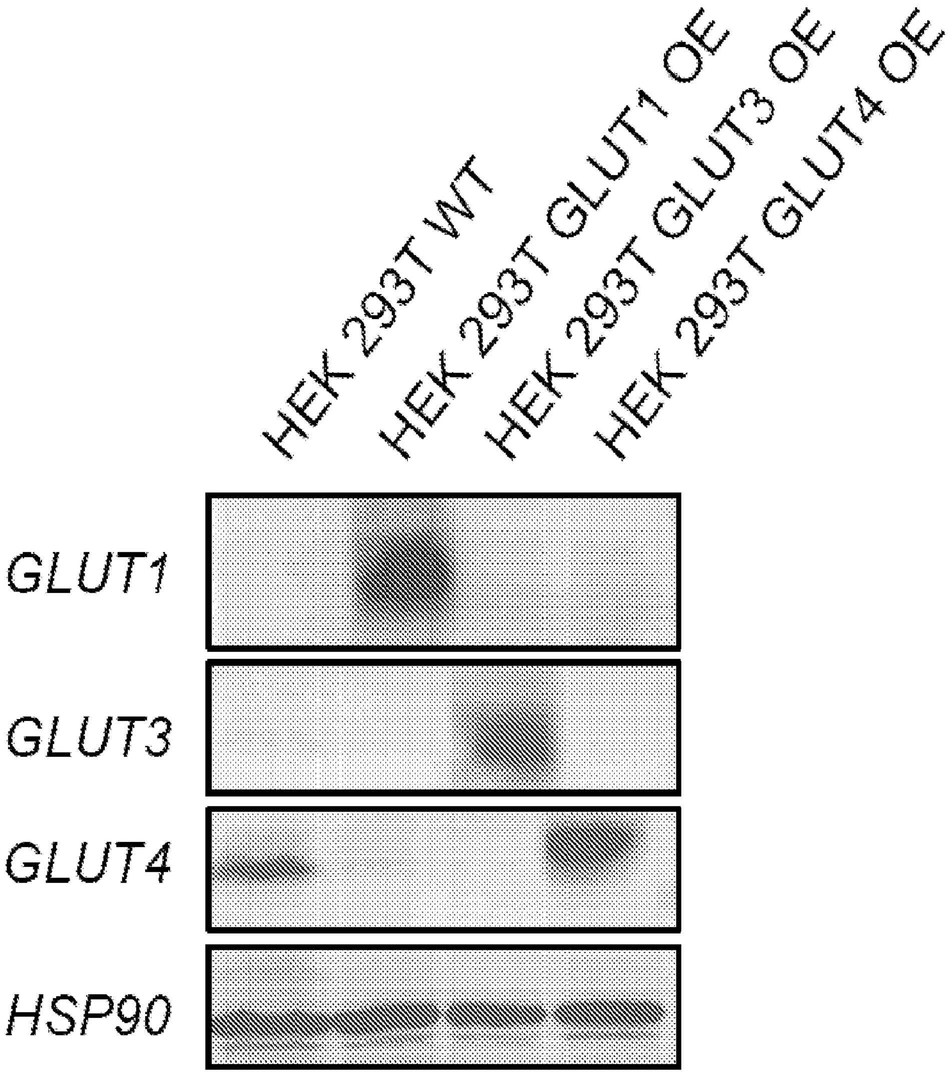
Figure 11:
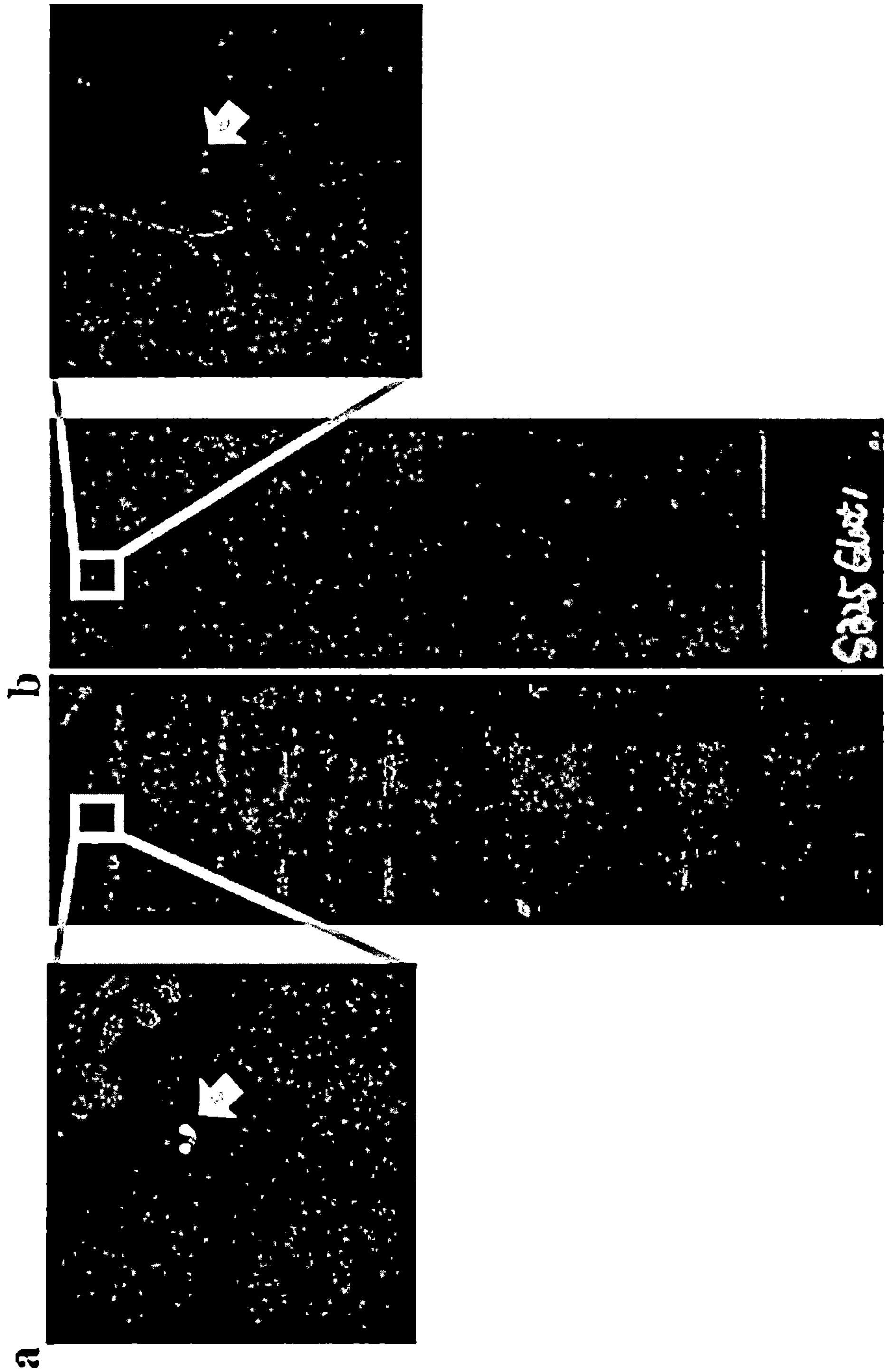
Figure 11:
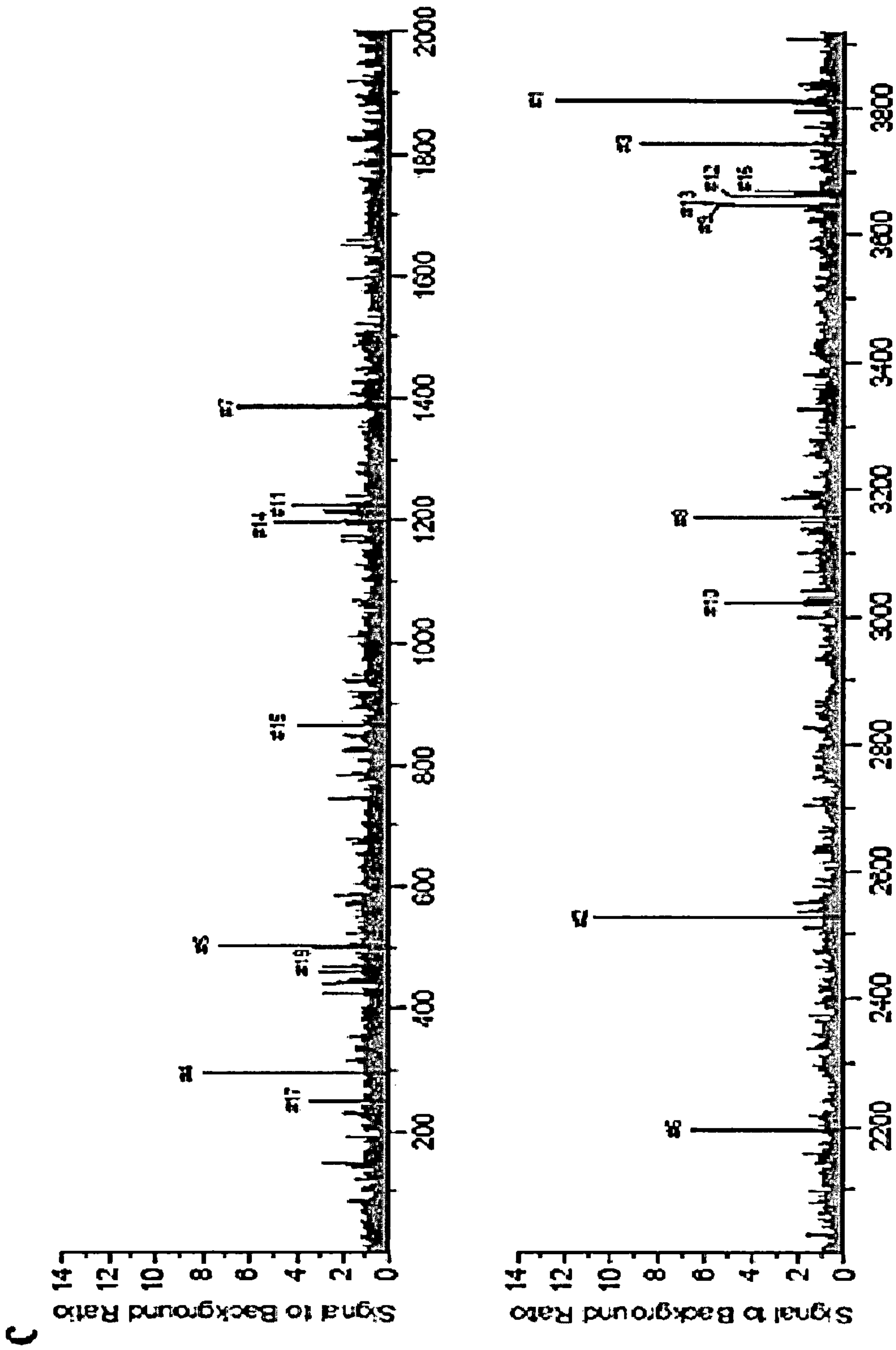
Figure 12:
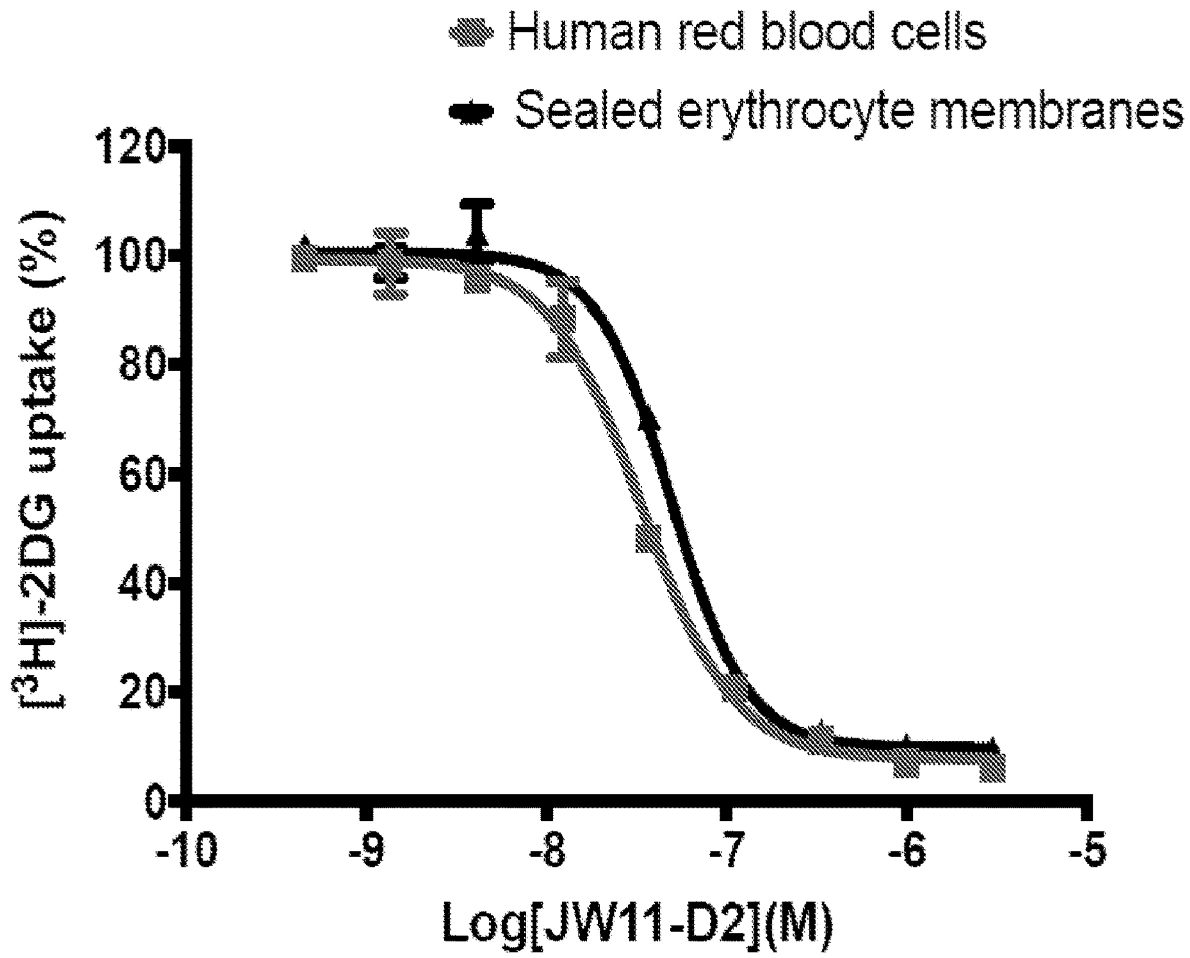
Figure 14:
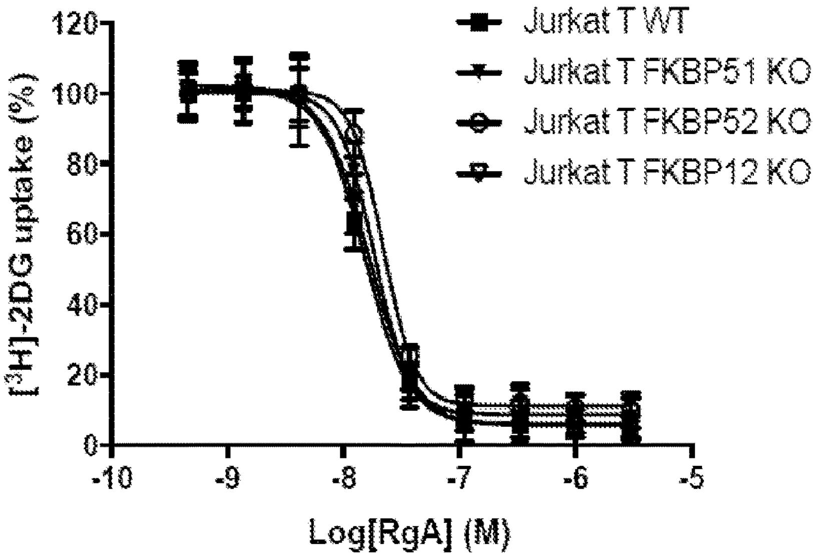
Figure 16:
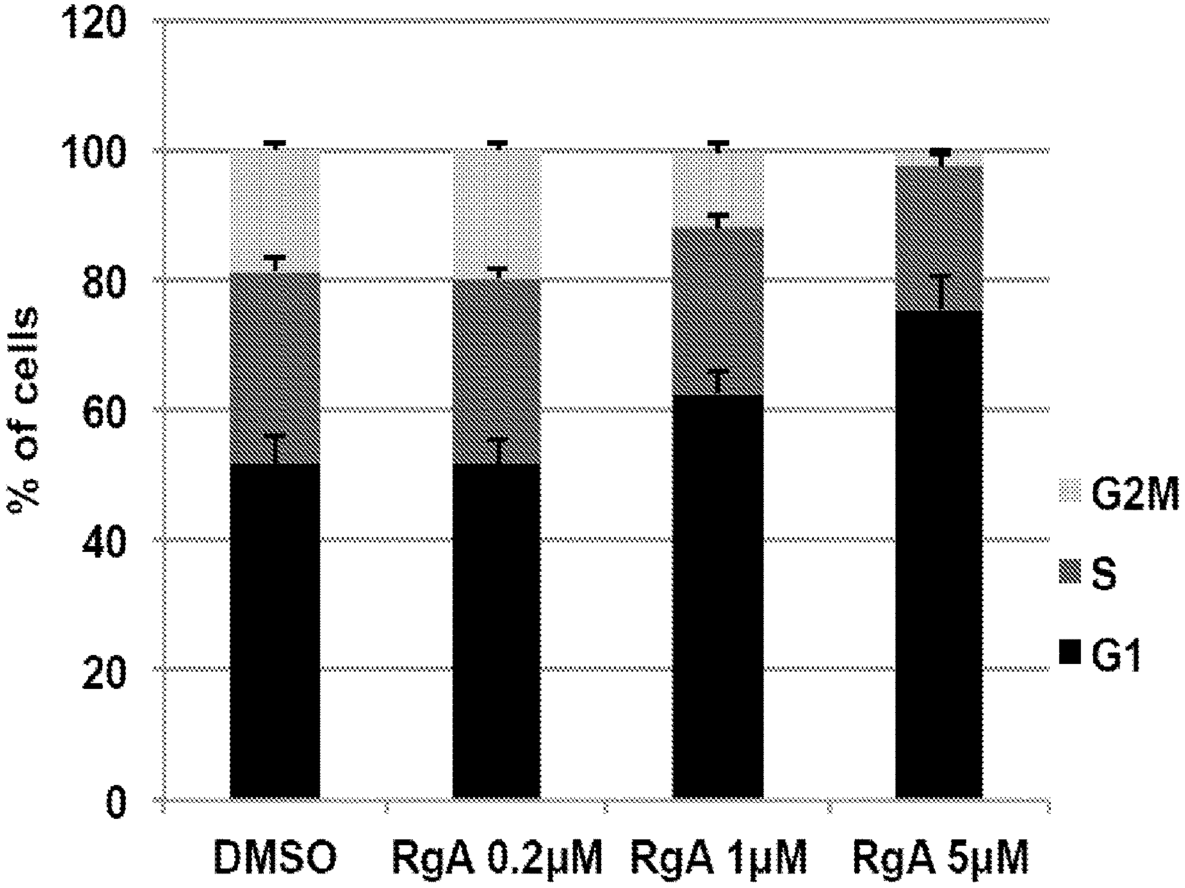
Figure 17:
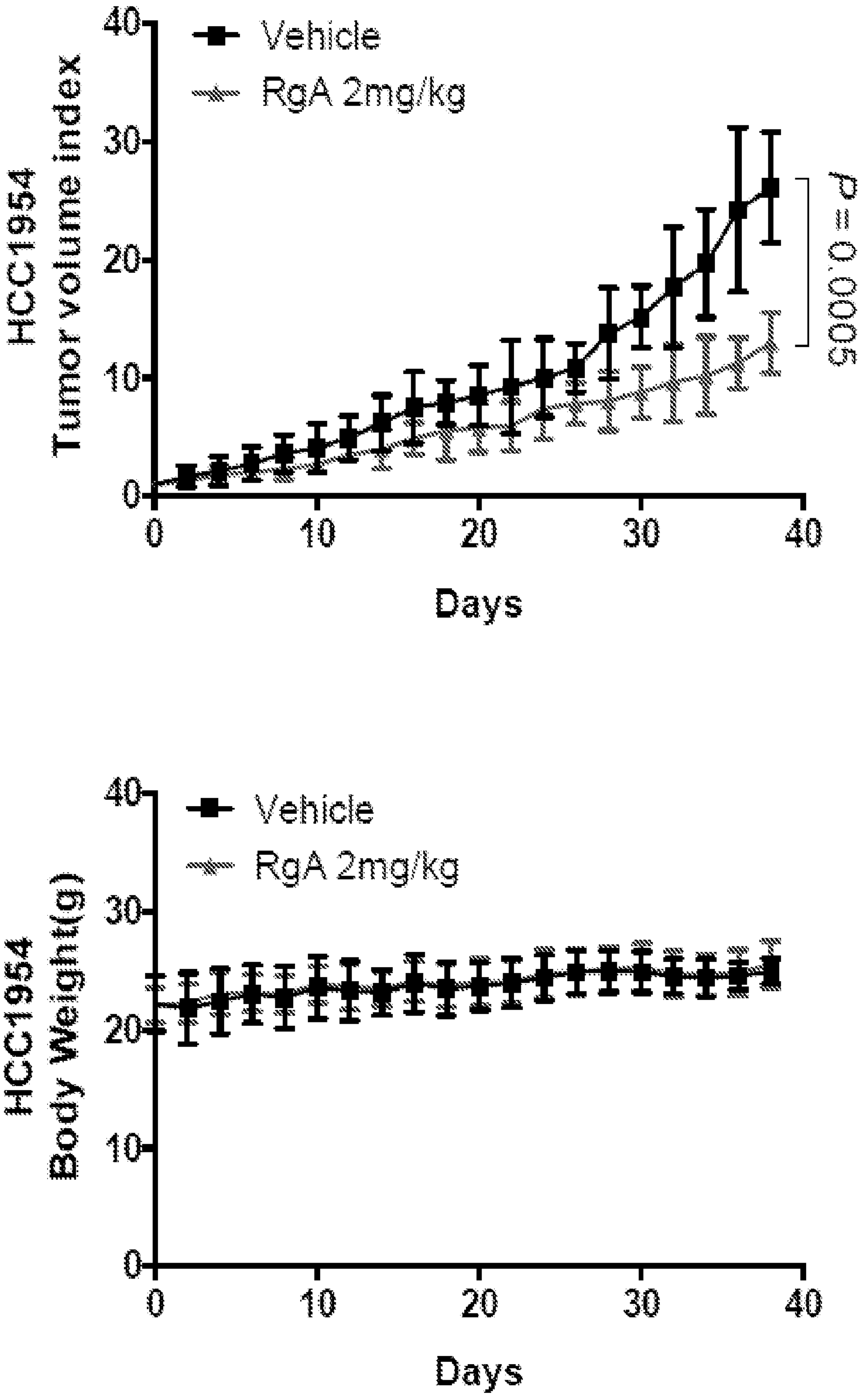
Figure 18:
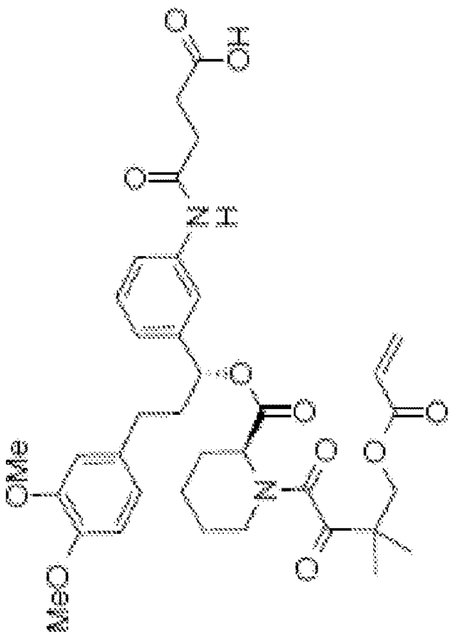
Figure 18:
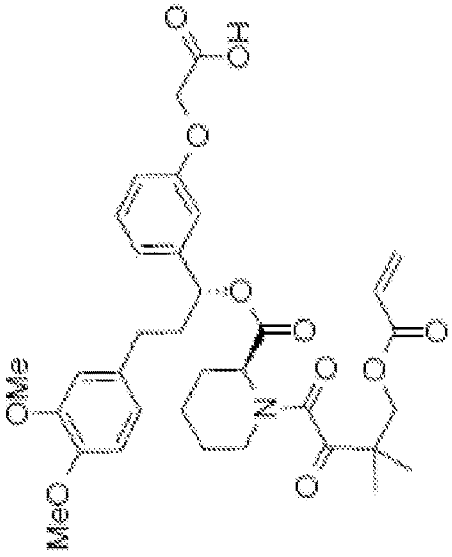
Figure 18:
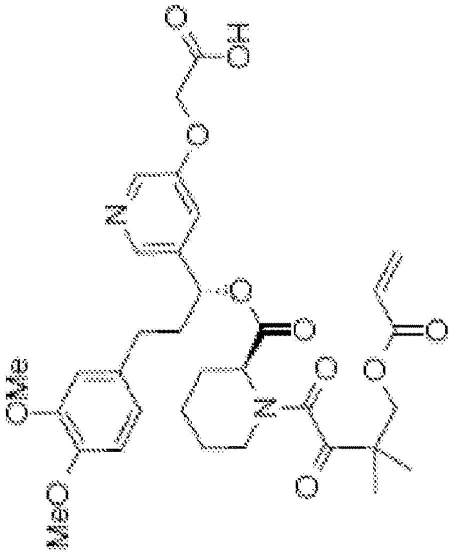
Figure 18:
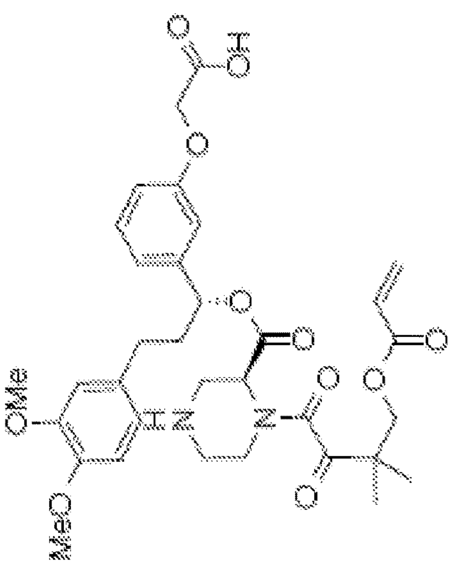
Figure 18:
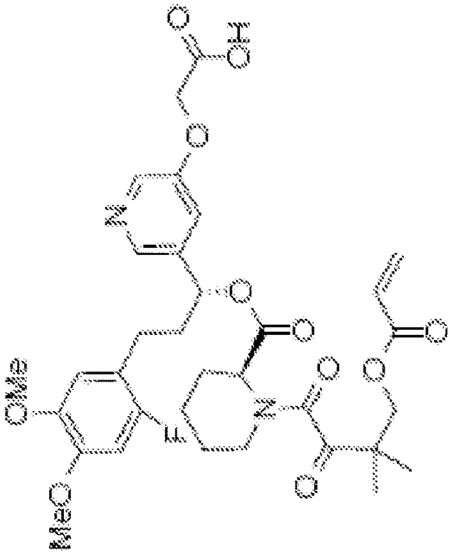
Figure 19:
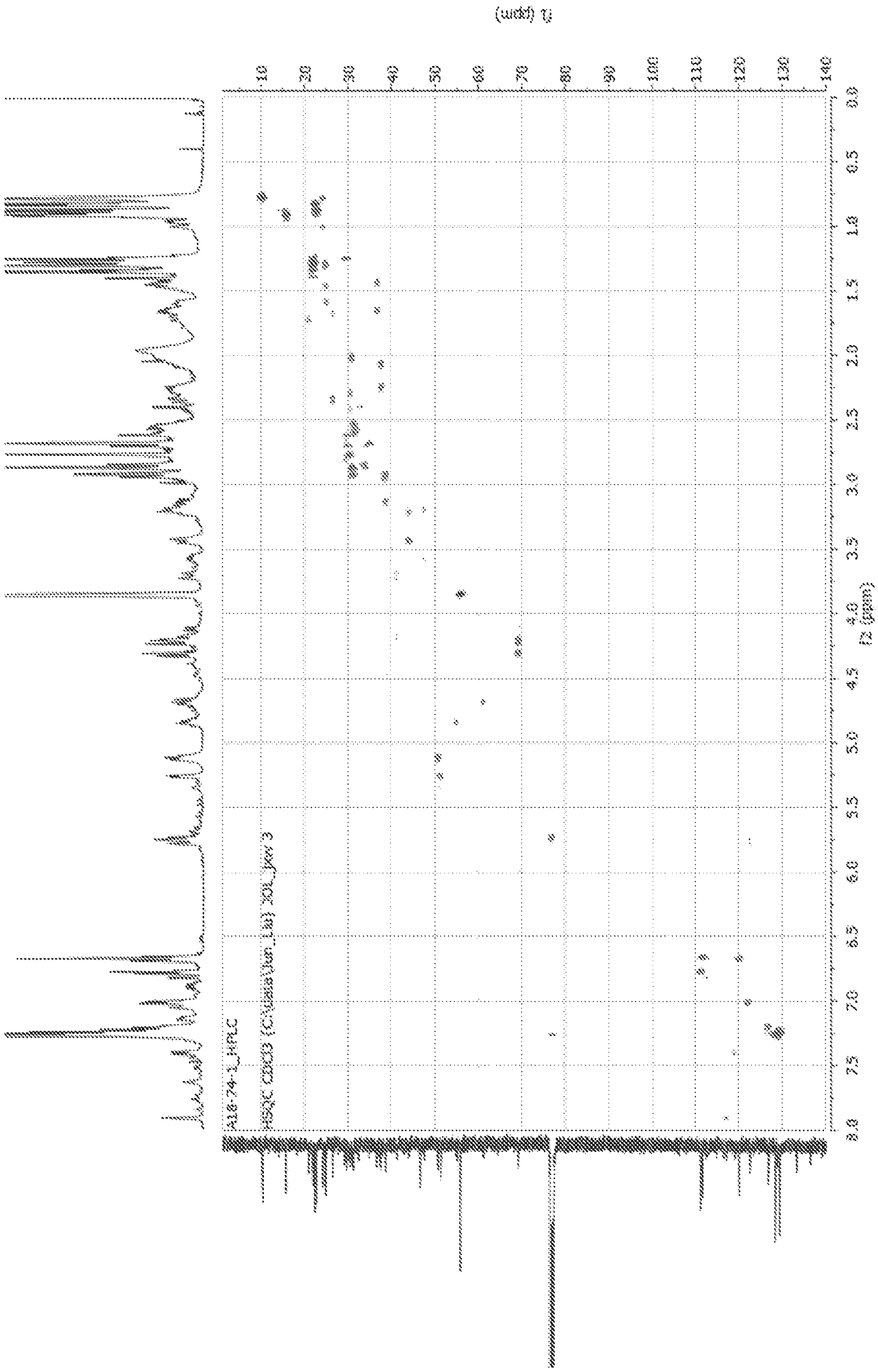
Figure 20:
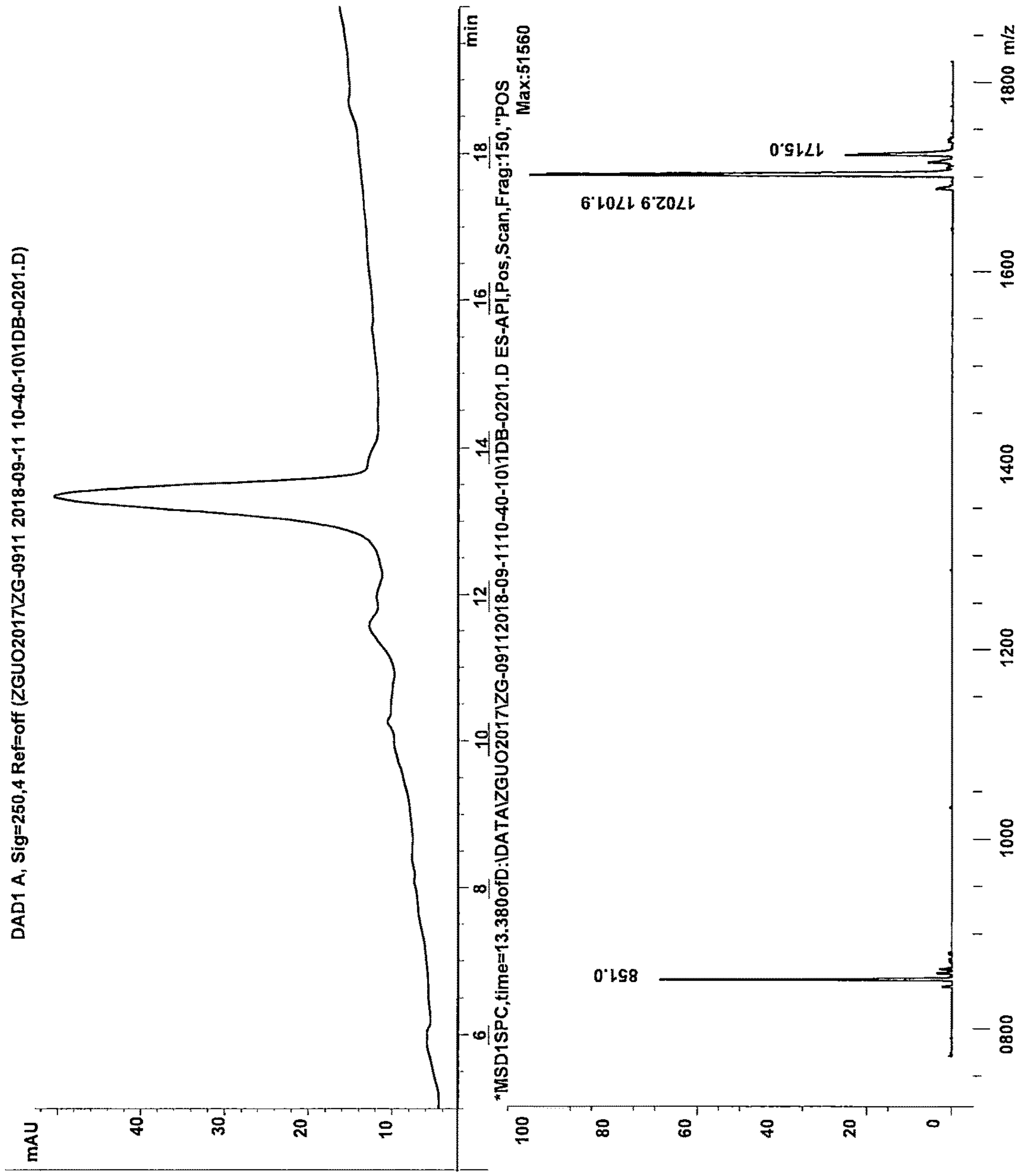
Figure 21:
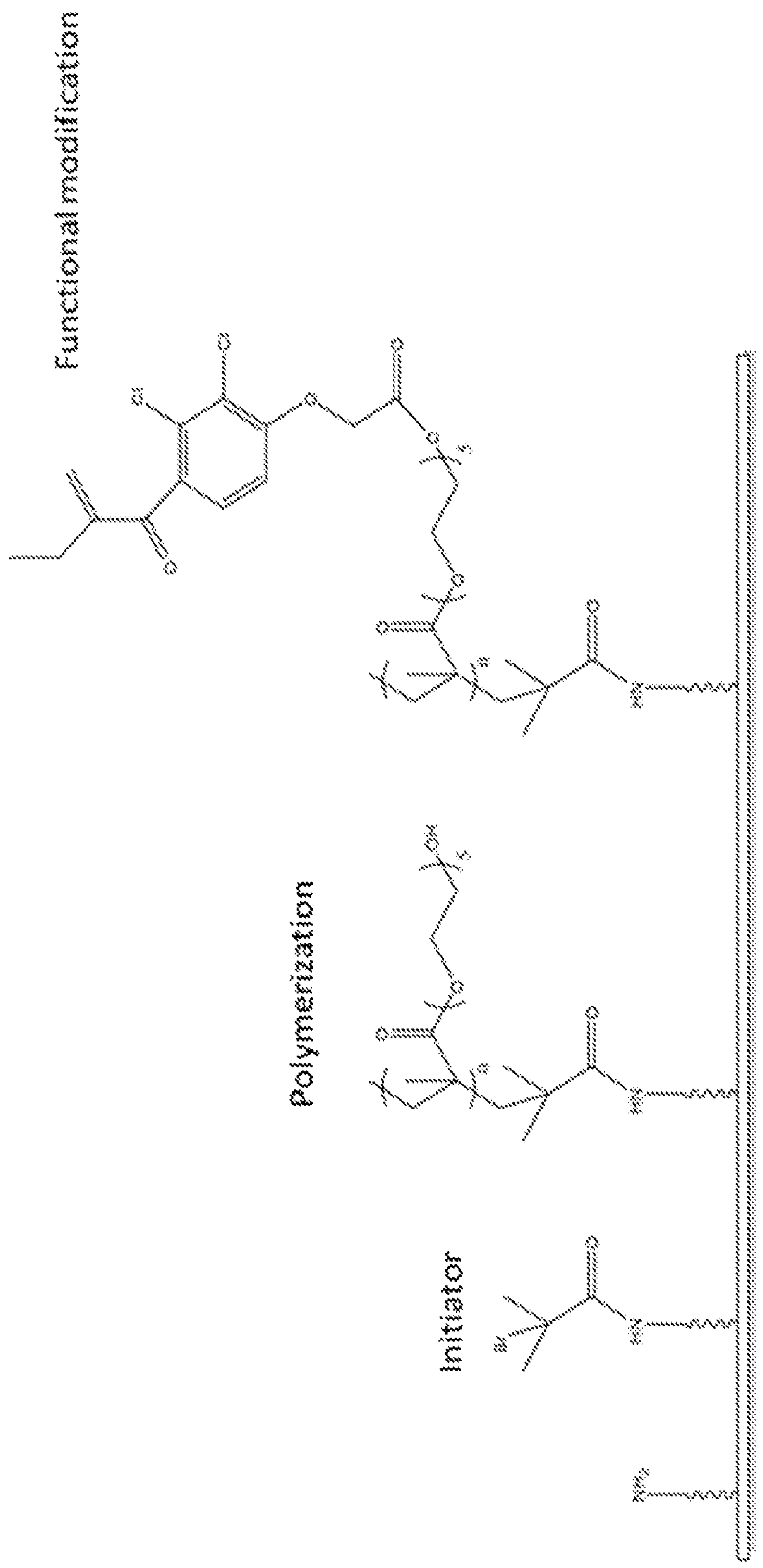
Figure 22:
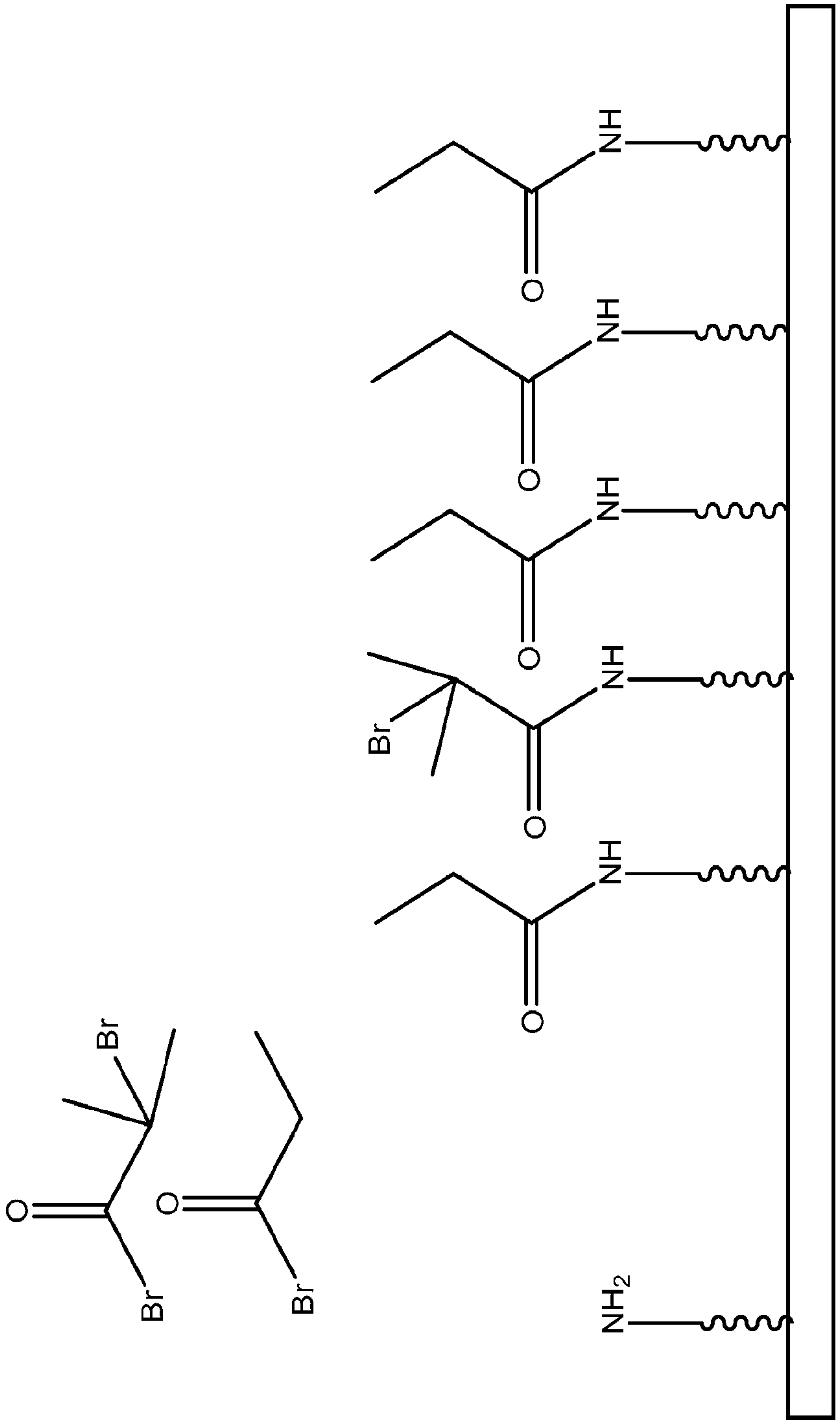
Figure 23:
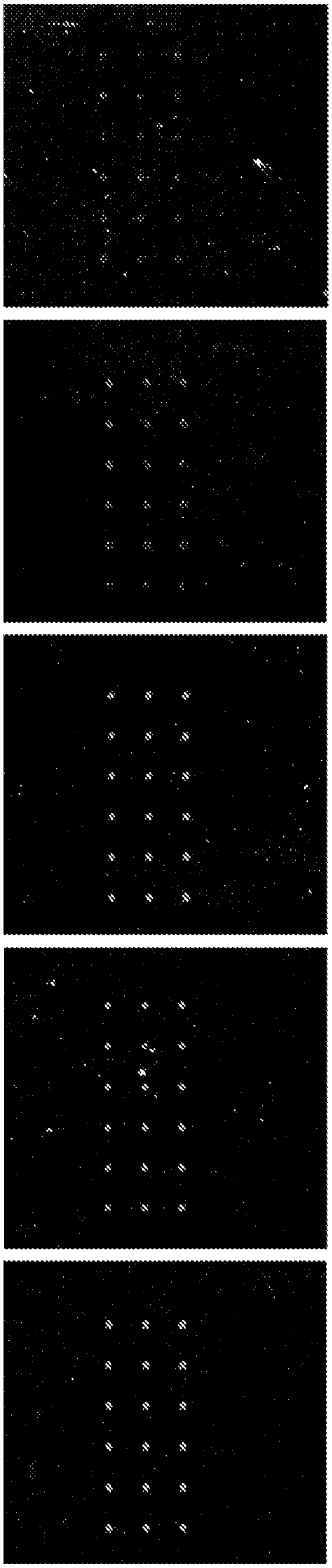
Figure 24:
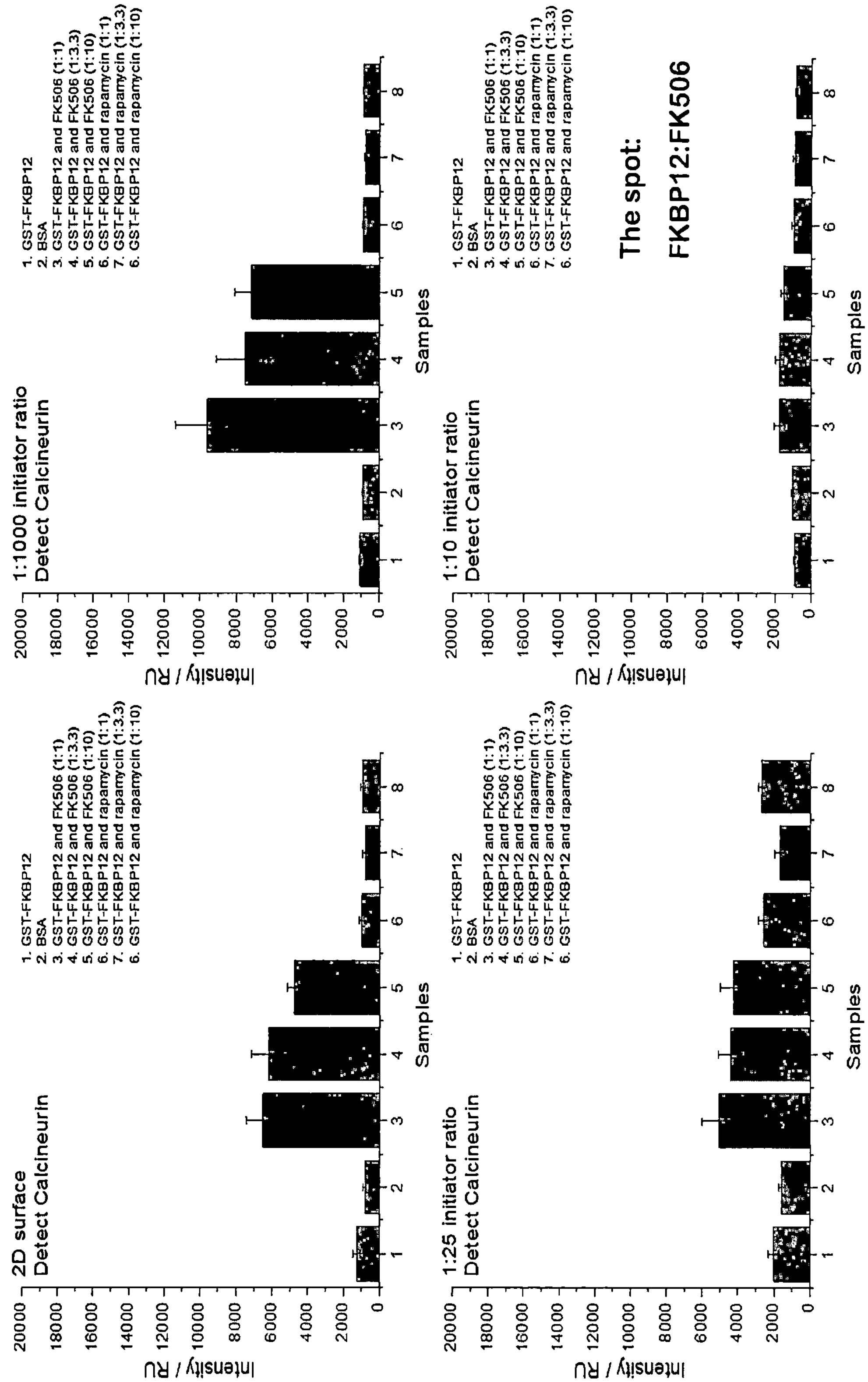
Figure 24:
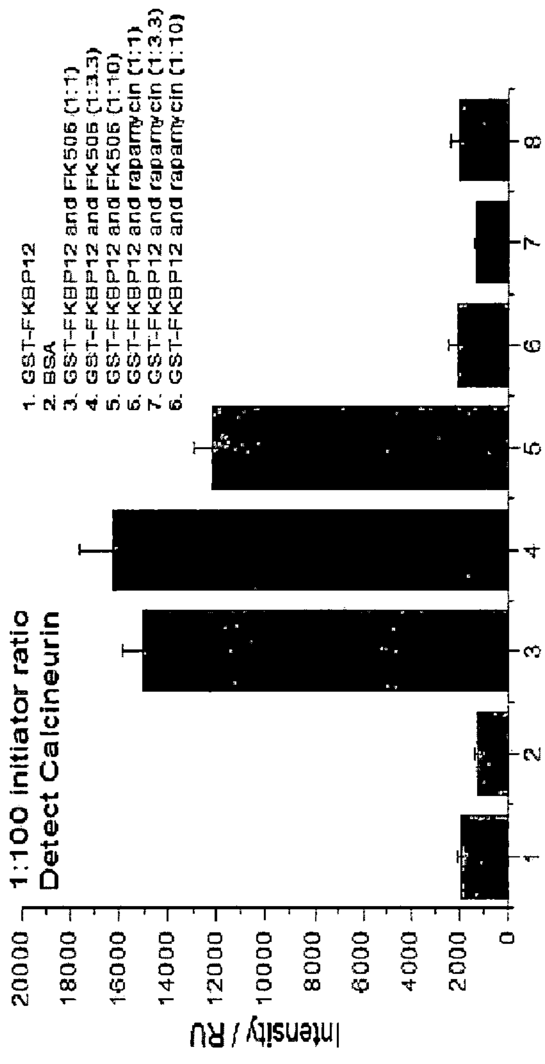
Figure 25:
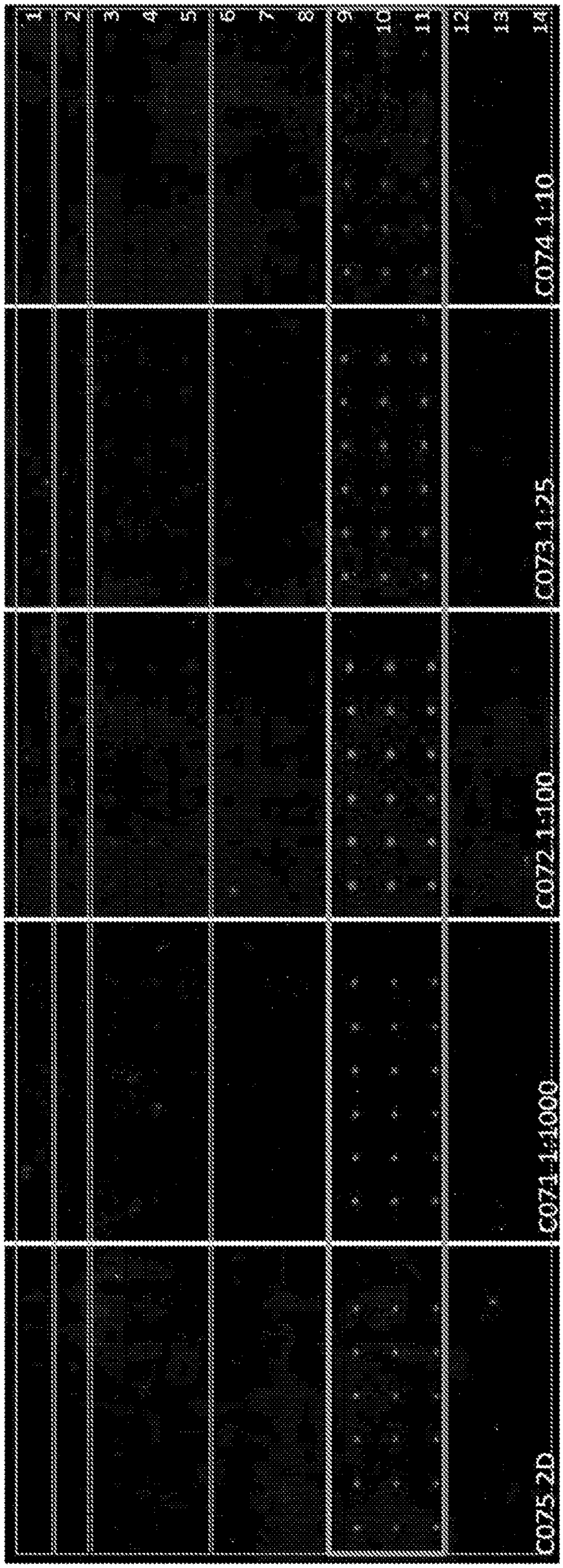
Figure 26:
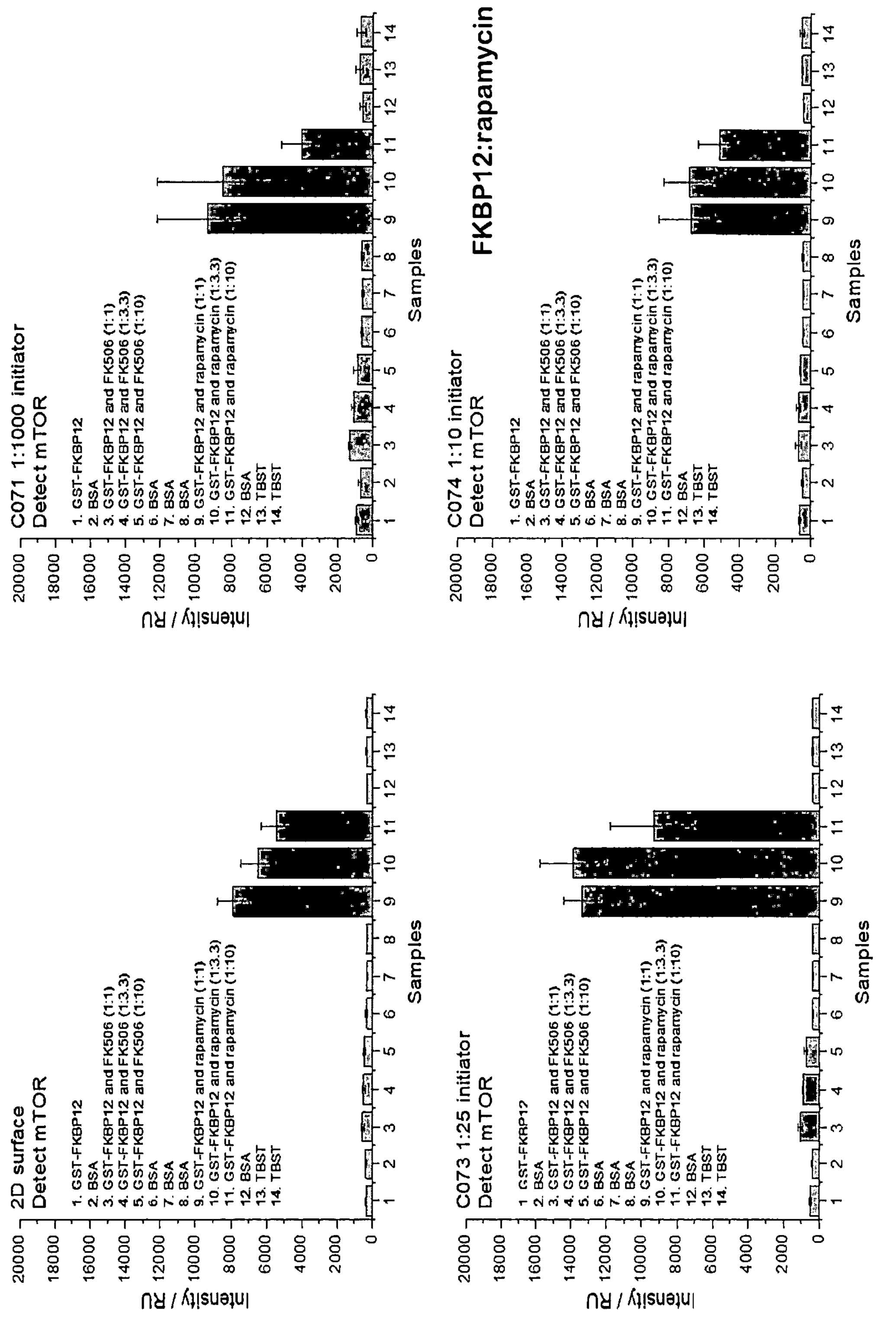
Figure 26:
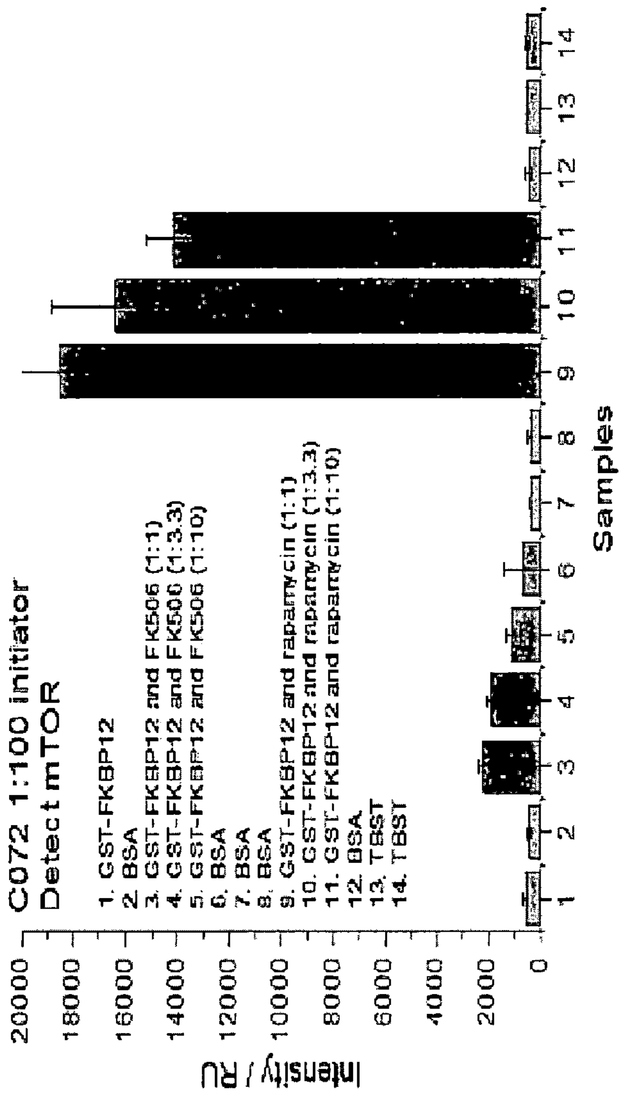
Figure 27:
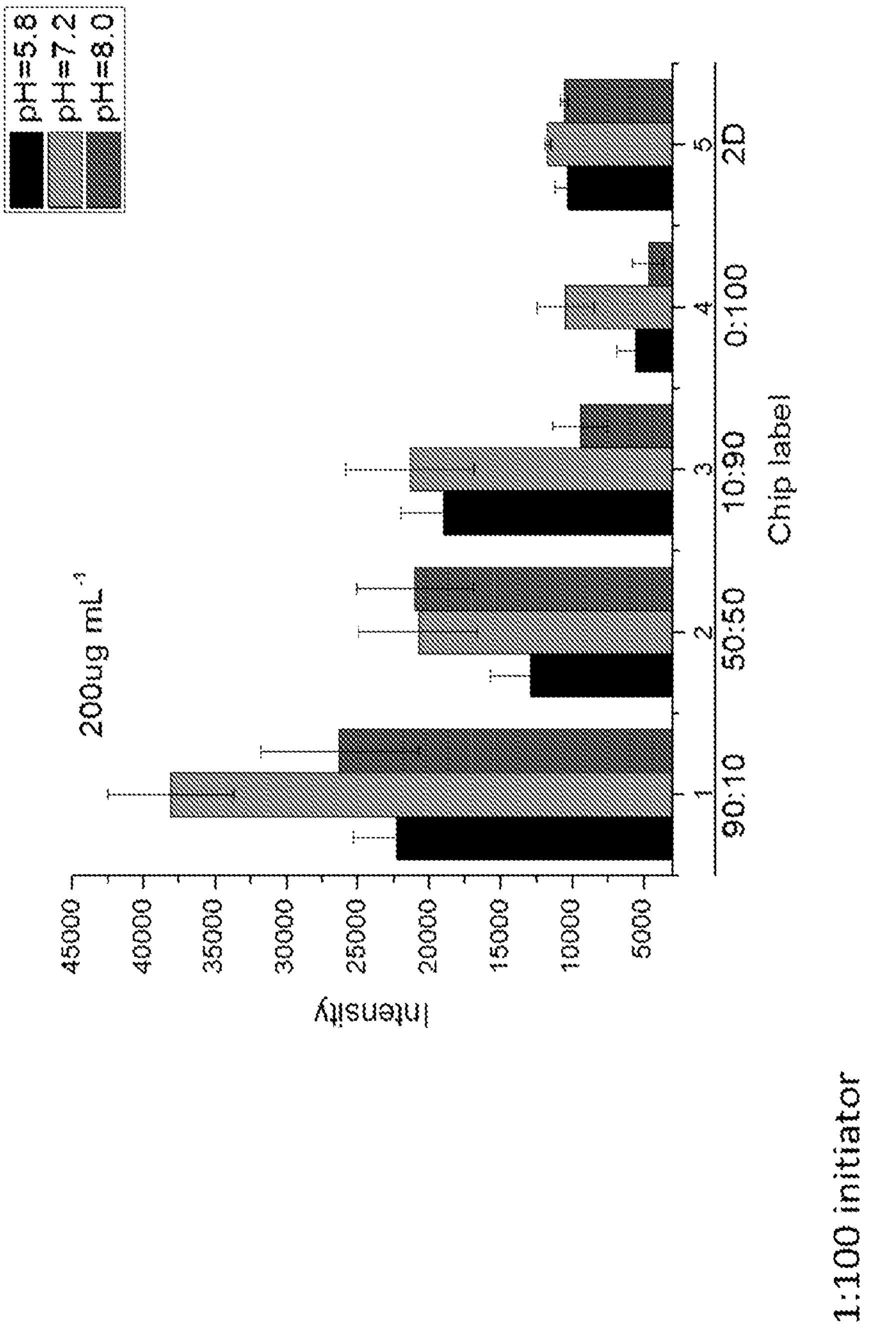
Figure 28:
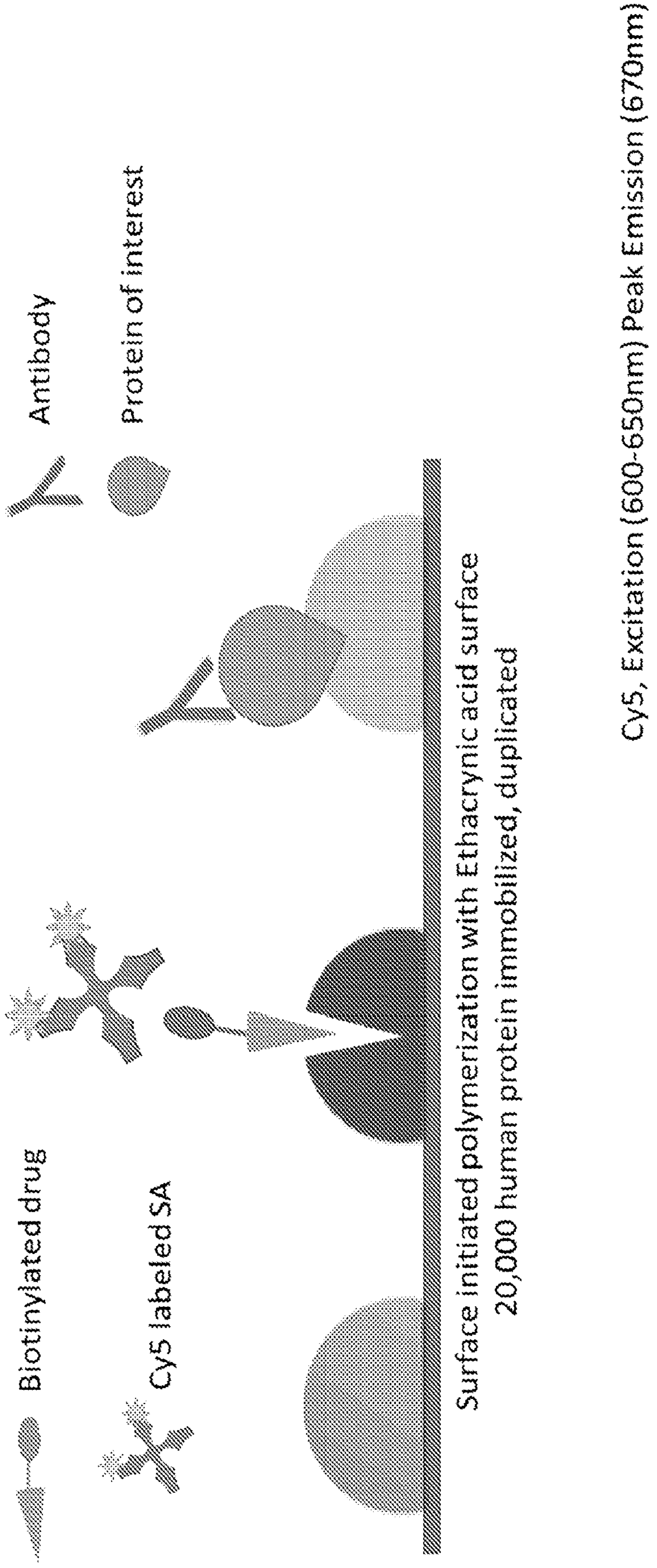
Figure 29:
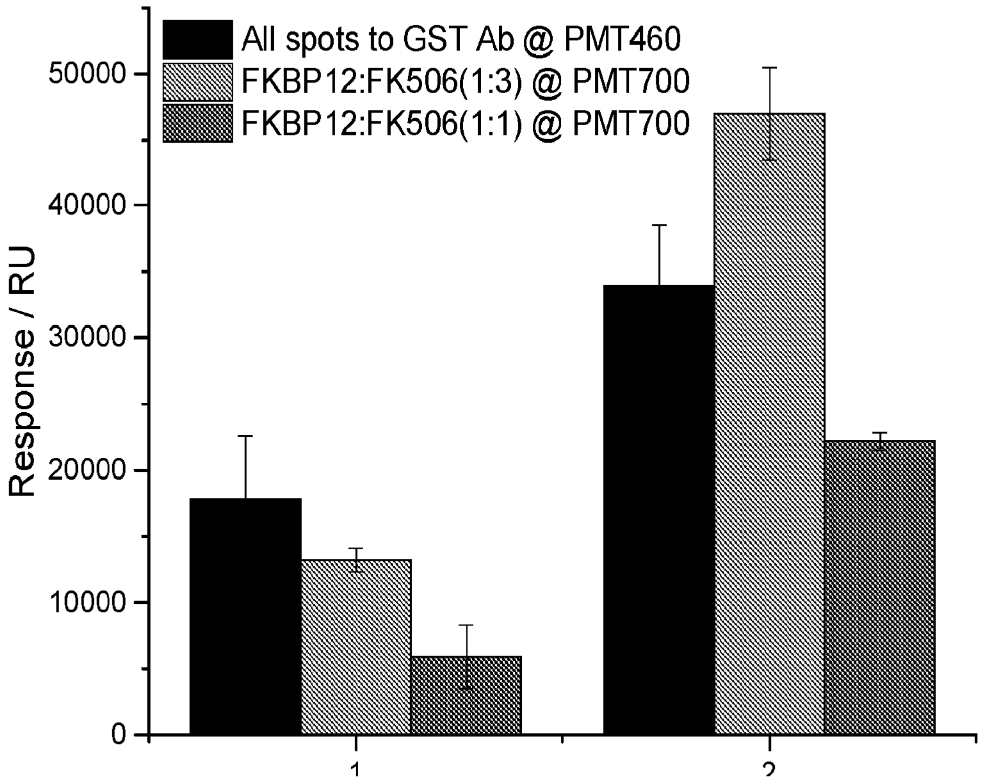
Figure 30:
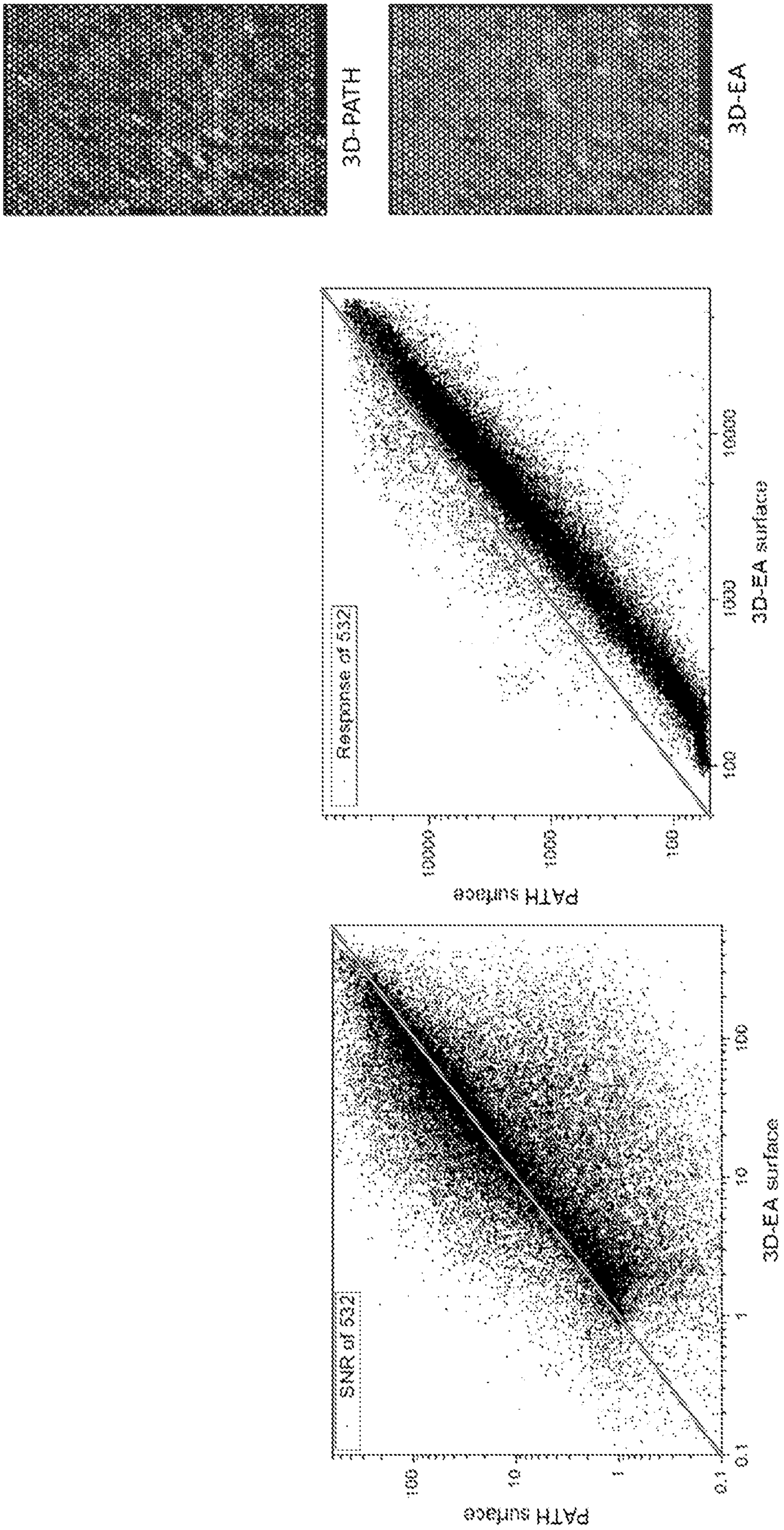
Figure 31:
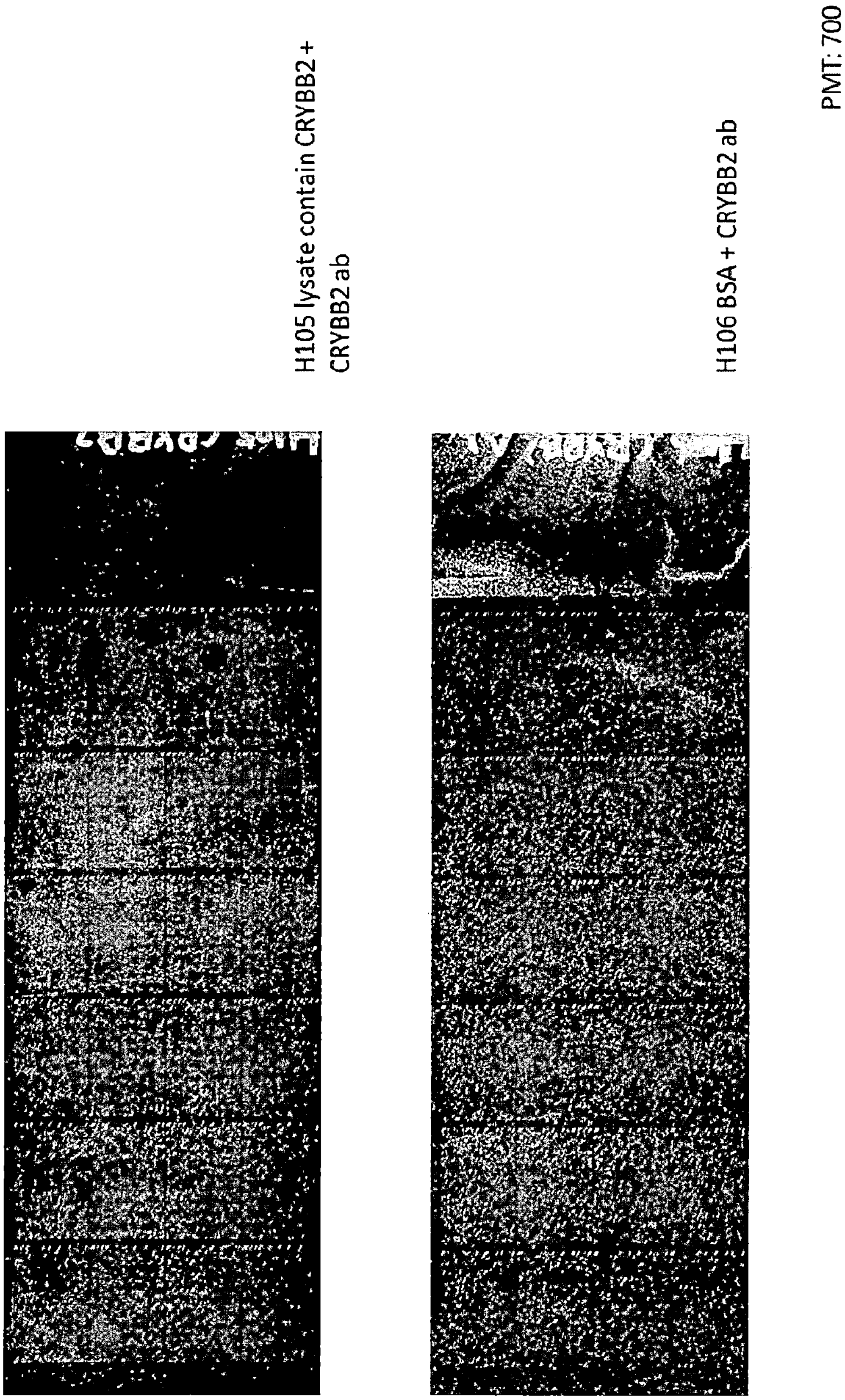
Figure 33:
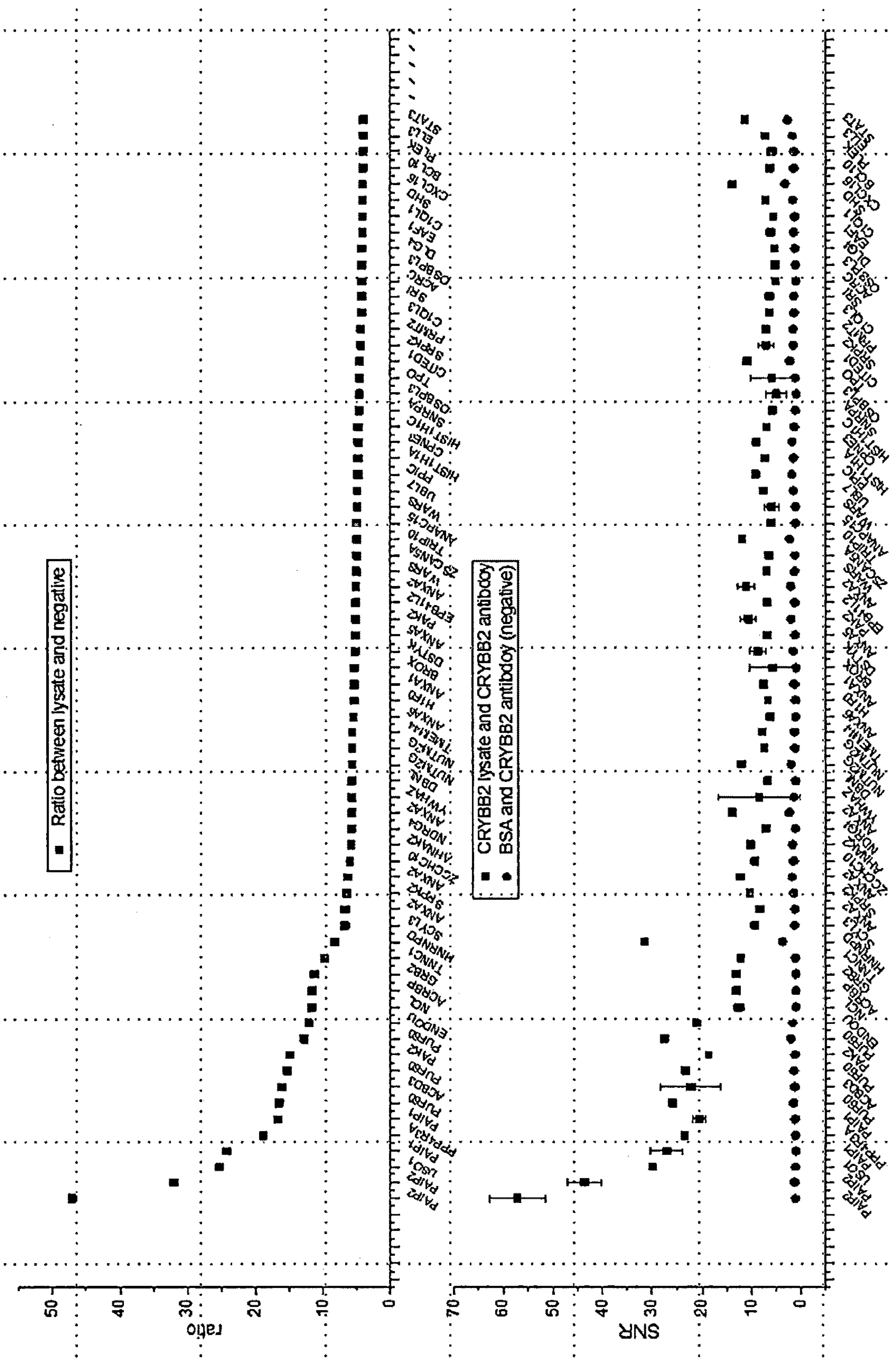
Figure 34:
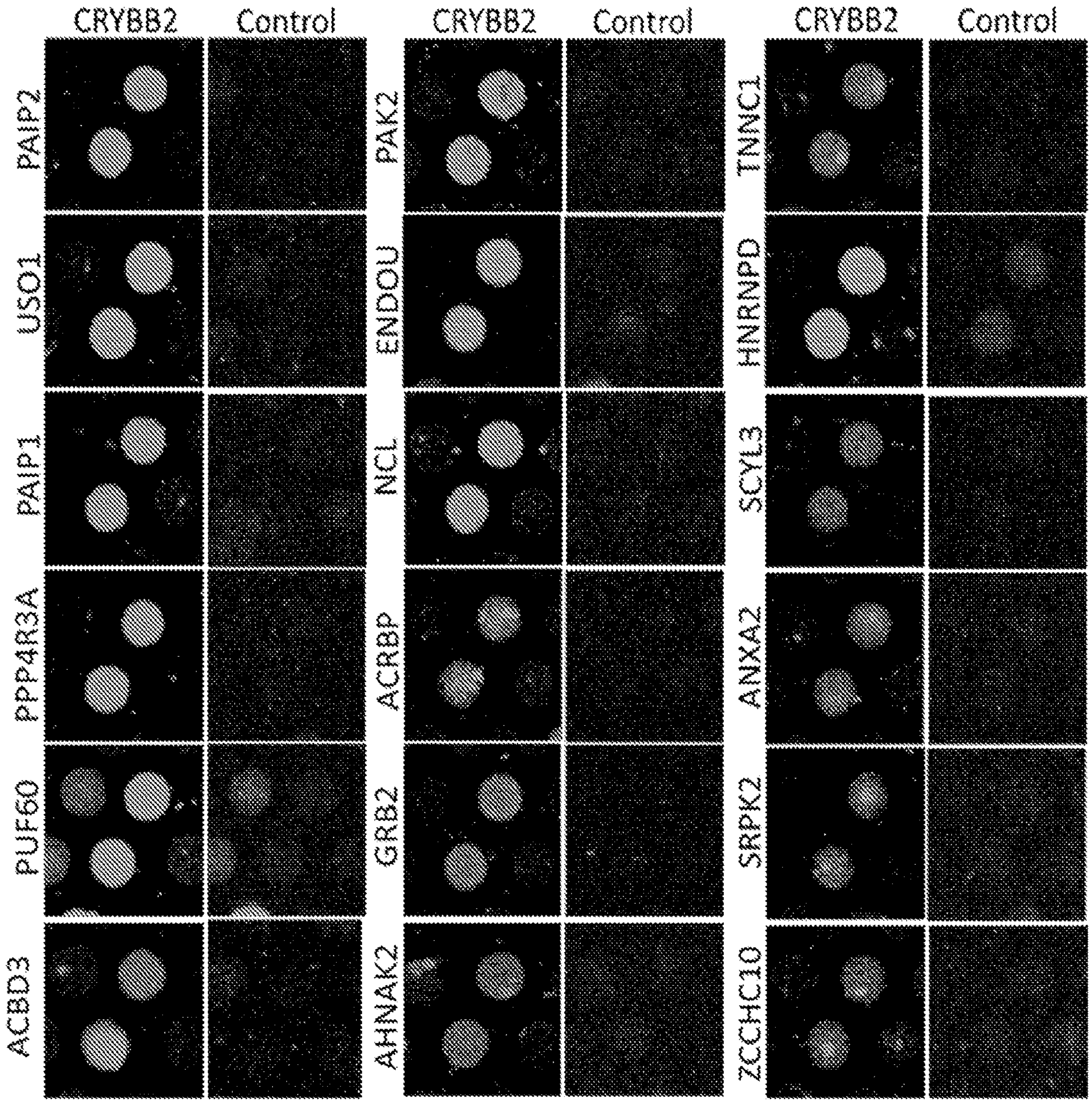
Figure 35:
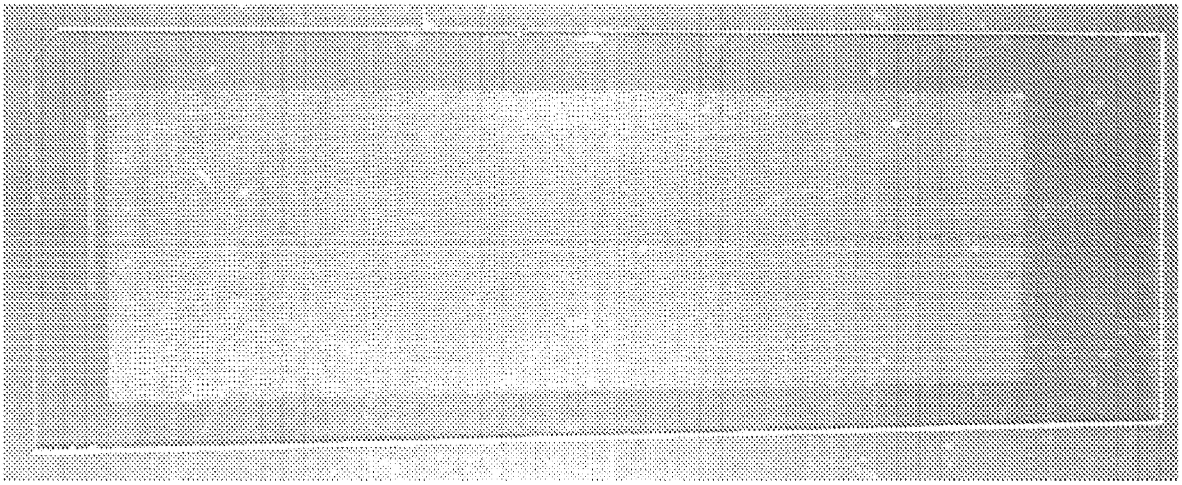
Figure 36:
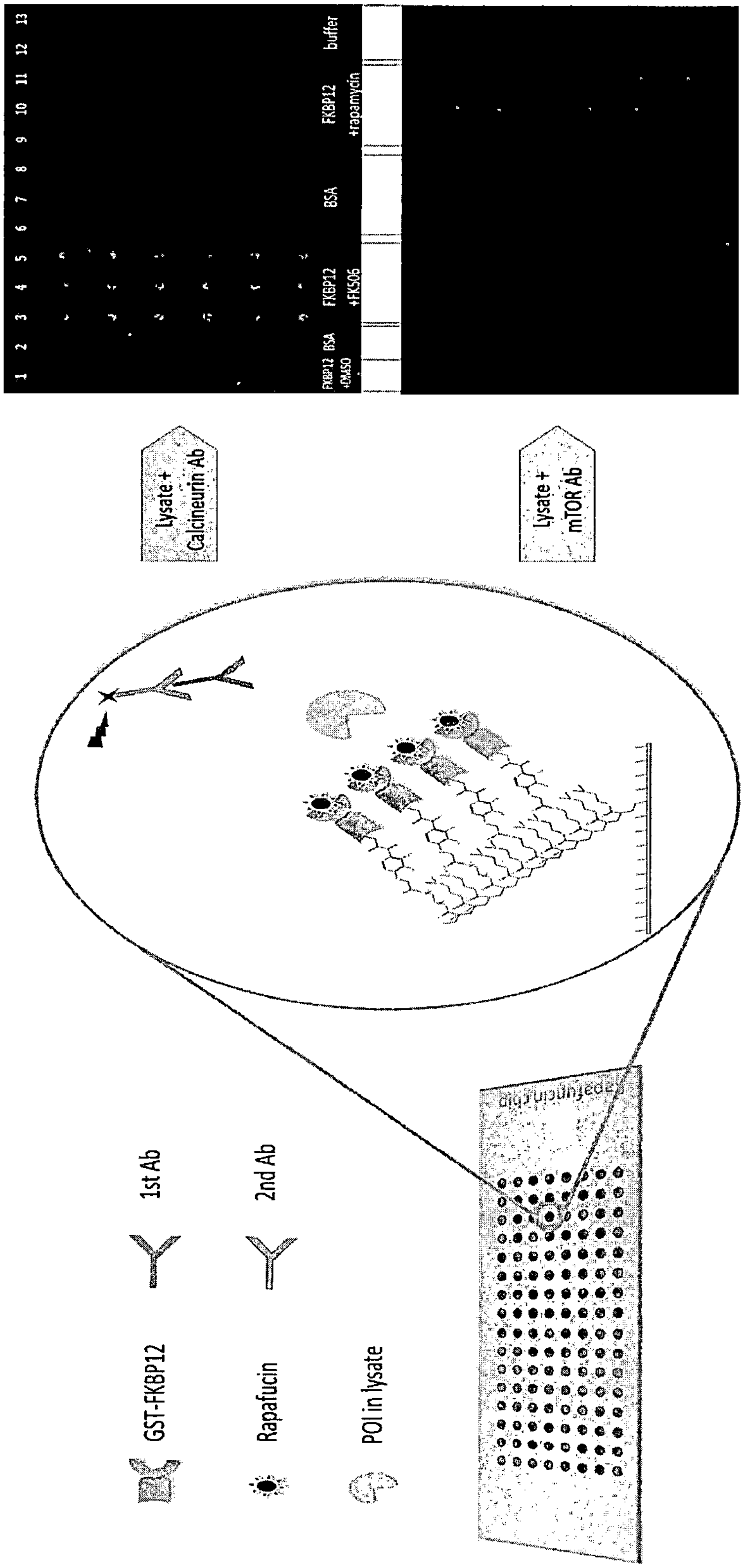
Figure 37:
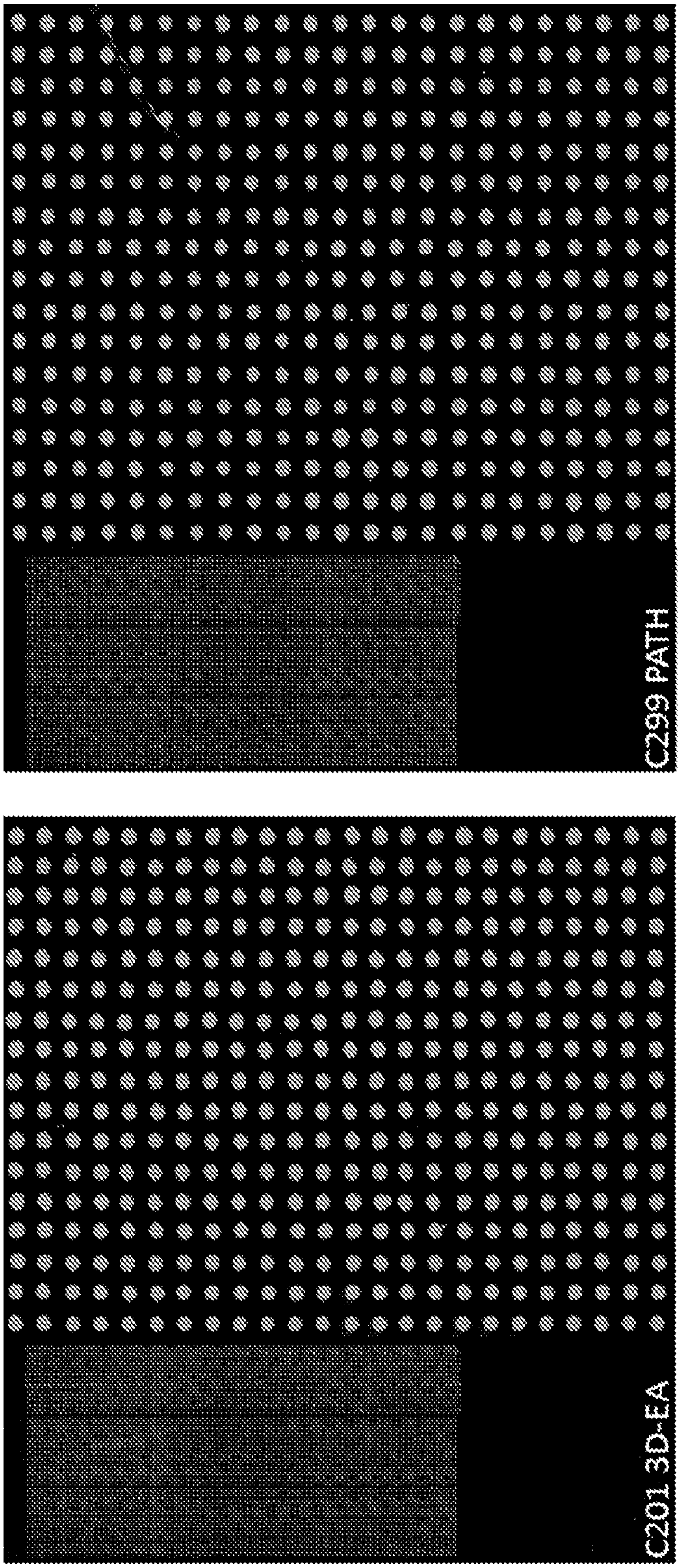
Figure 38:
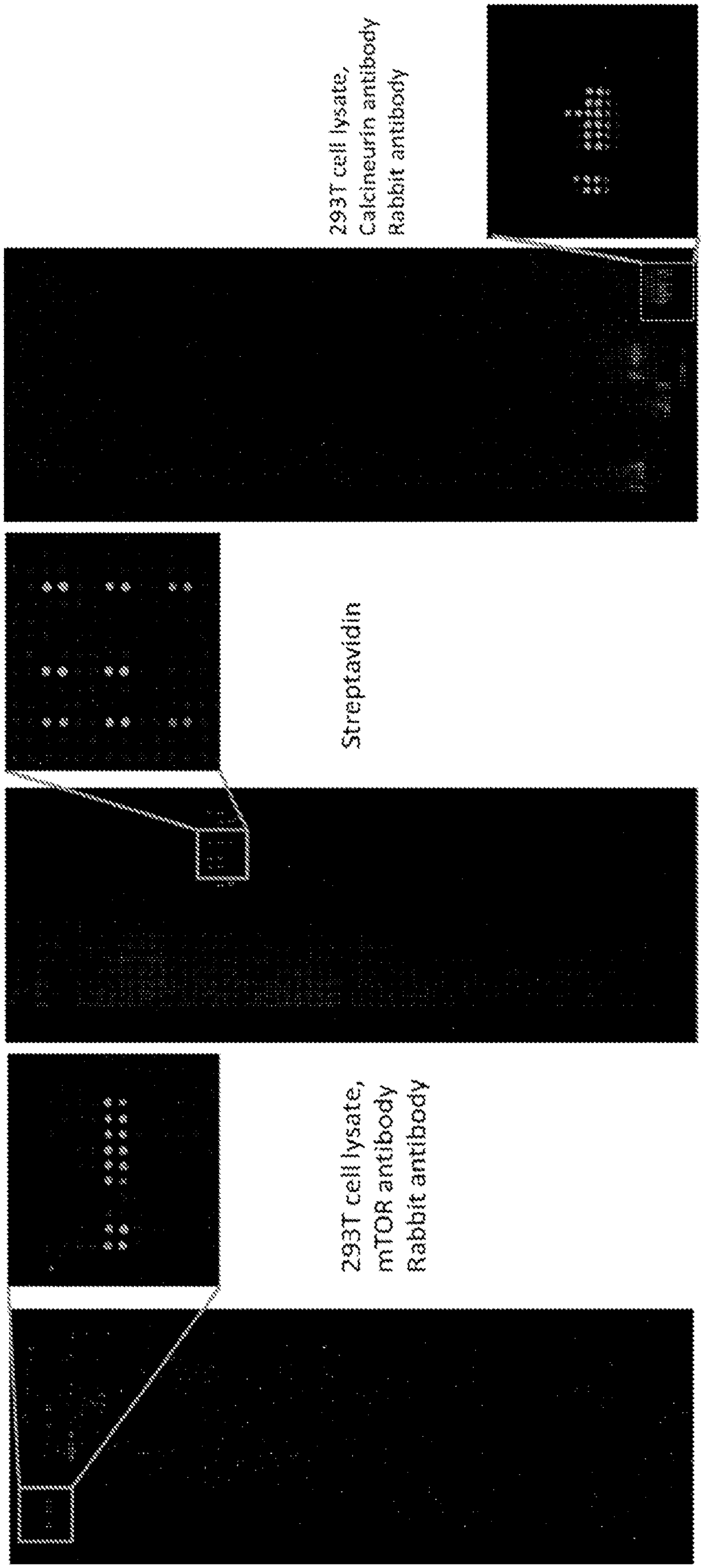
Figure 39:
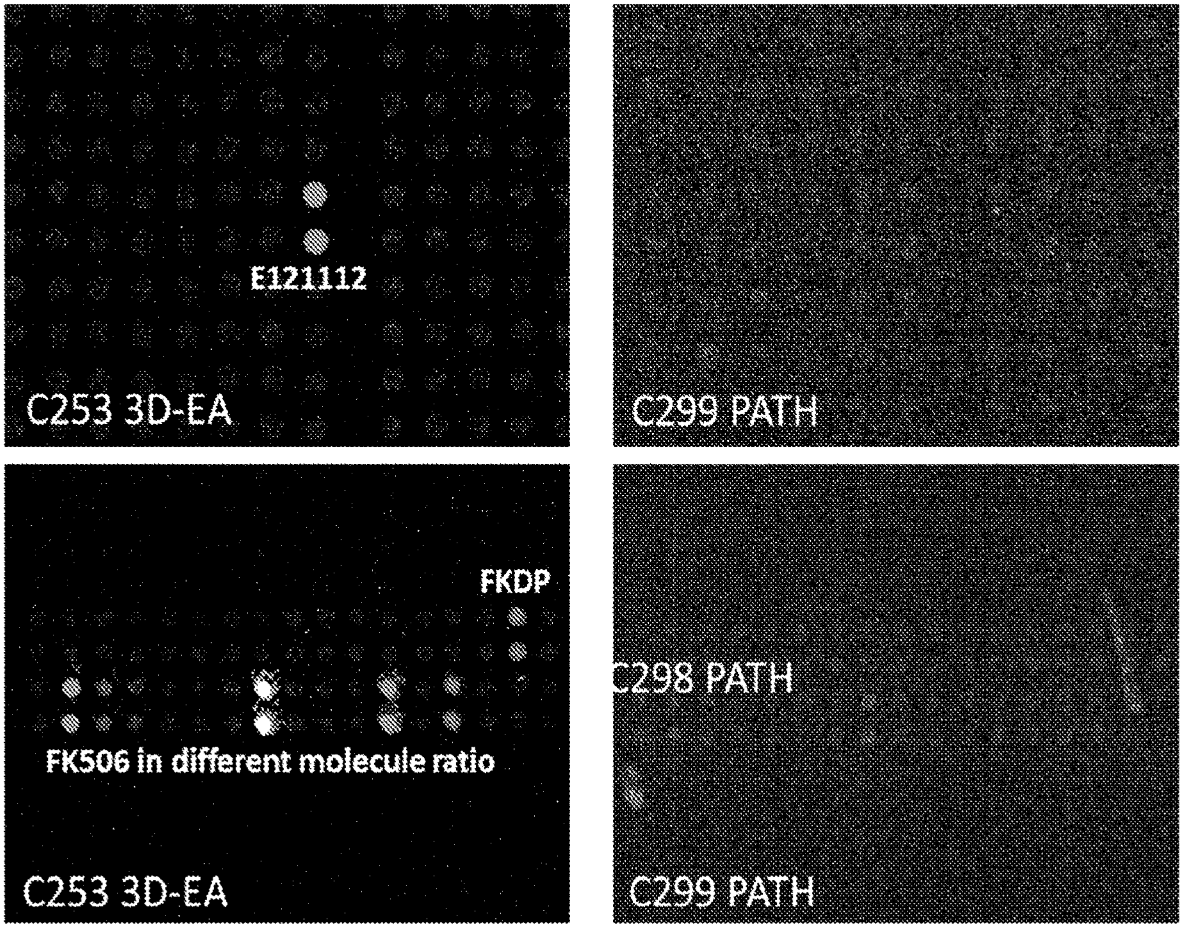
Figure 40:
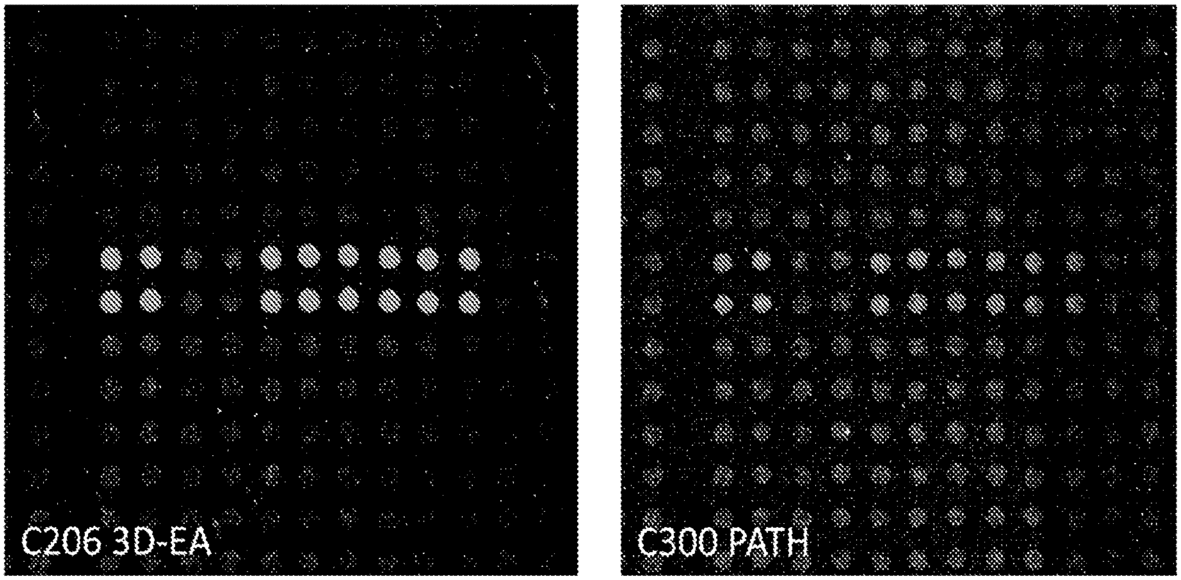
Figure 41:
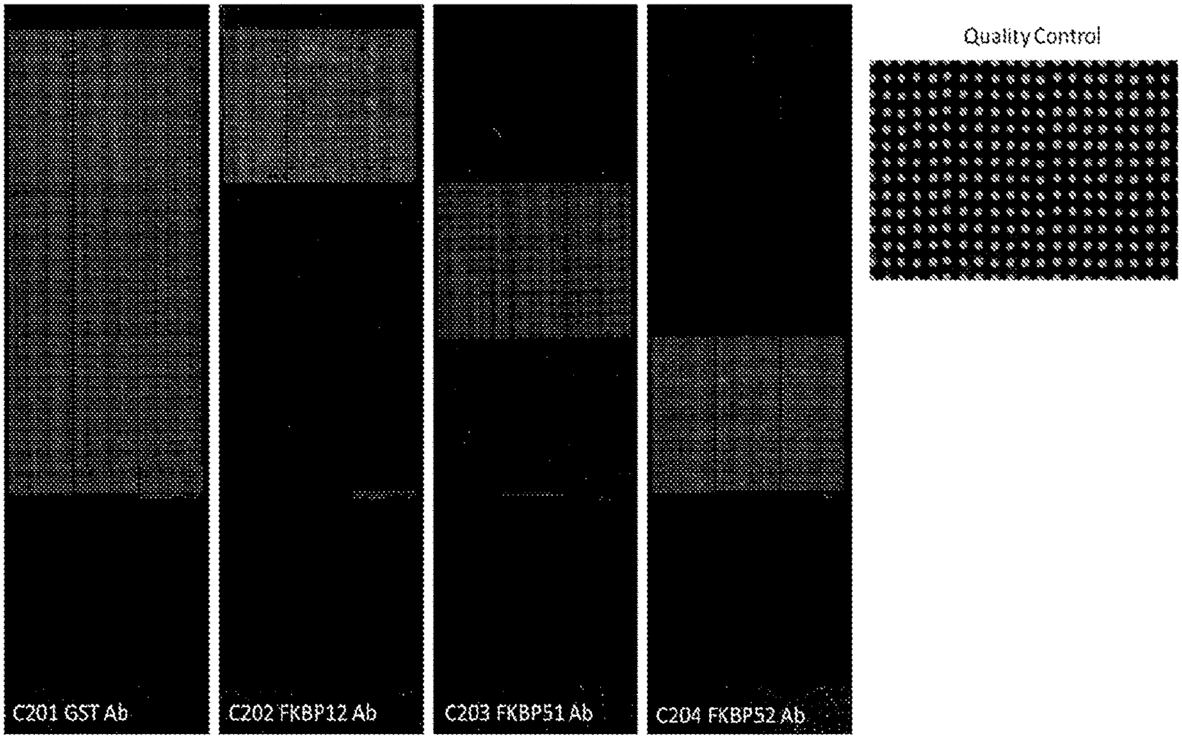
Figure 42:
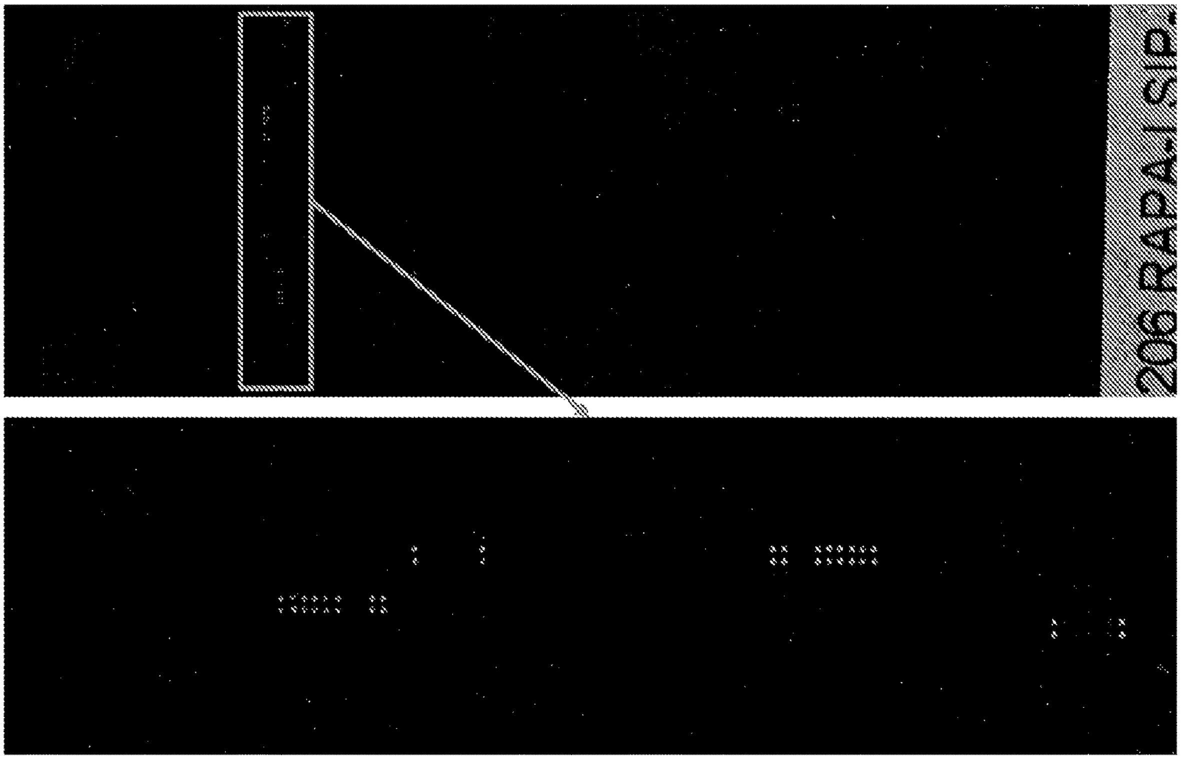
Figure 43:
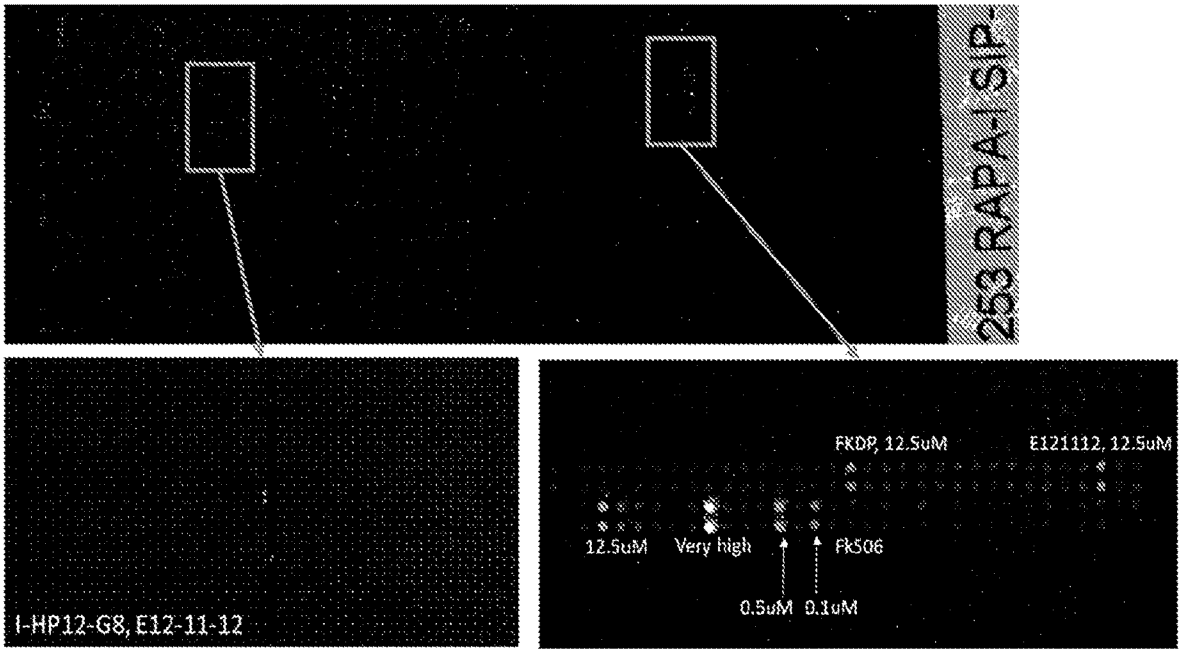
Figure 44:
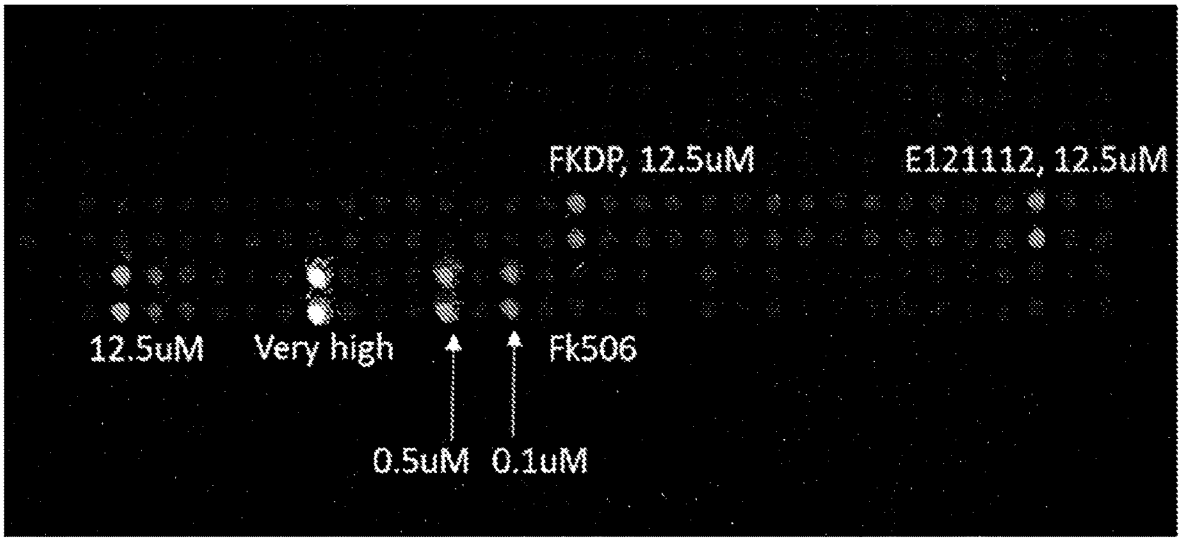
Figure 45:
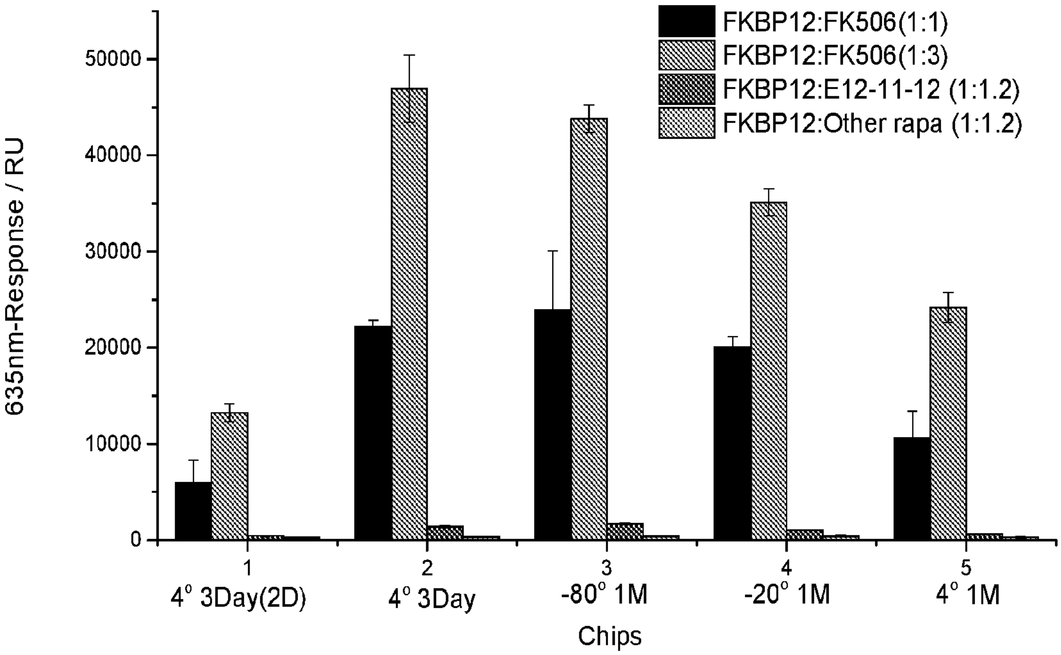

Having thus described the presently disclosed subject matter in general terms, reference will now be made to the accompanying Figures, which are not necessarily drawn to scale, and wherein:

FIG. 1A, FIG. 1B, and FIG. 1C show the development of the presently disclosed rapafucin 3D microarray. (FIG. 1A) The construction of the rapafucin 2D and 3D microarrays. Ab, antibody; POI, protein of interest; red star, positive POI binder; green star, negative POI binder. (FIG. 1B) Optimization of 3D microarray. Small molecule array screening against purified GST-FKBP12 on 3D copolymer diazirine surface with different ratios of monomers, PEGMA and DMEAMA (PEGMA:DMEAMA=0:10, 2:8, 5:5, 8:2 or 10:0). (FIG. 1C) Comparison of the interaction between rapafucins and FKBP12 on 2D and 3D surfaces. Microarray images of the rapafucin 2D and 3D microarrays probed by purified GST-FKBP12. All of the compounds were spotted in duplicate;

FIG. 2A, FIG. 2B, FIG. 2C, and FIG. 2D demonstrate the identification of Rapafucin JW11-D2 as a GLUT1 binder. (FIG. 2A) 3D Microarray images of two positive hits JW11-D2 and HP17-C2. (FIG. 2B) Chemical structures of JW11-D2 (Rapaglutin A, RgA) and HP17-C2. (FIG. 2C) Inhibition of 2-deoxy-D-[3H] glucose (3H-2DG) uptake in A549 cells by RgA and HP17-C2. (FIG. 2D) The competition profile of biotin-RgA binding to GLUT1 in HEK 293T cell lysate by RgA. Representative image of n=3 independent experiments with similar results. Error bars represent s.d.; data are mean±s.d.;

FIG. 3A, FIG. 3B, FIG. 3C, and FIG. 3D demonstrate that RgA is a potent, isoform-nonspecific, and FKBD-independent inhibitor of glucose transporters. (FIG. 3A) Inhibition of 2-deoxy-D-[3H] glucose ([3H]-2DG) uptake in A549, HCC1954, and MCF-7 cells by RgA; (FIG. 3B) Inhibition of [3H]-2DG uptake in DLD1 wild type or GLUT1 knock out cells by RgA, BAY-876, and Cytochalasin B (CytoB); (FIG. 3C) Pulldown of GLUT1, GLUT3, or GLUT4 by a biotin-RgA conjugate. GLUT1, GLUT3, or GLUT4 protein levels were detected by Western blot. (FIG. 3D) Inhibition of [3H]-2DG uptake in MCF-7 cells by 100 nM of RgA, 20 μM of FK506, 20 μM of Rapamycin and their combinations. In all graphs, Error bars represent s.d.; data are mean±s.d.;

FIG. 4A and FIG. 4B demonstrate that RgA inhibits glycolysis, actives AMPK and blocks mTOR pathway. (FIG. 4A) Volcano plots showing metabolite profiles of MCF-7 cells treated with RgA for 30 min or 6 h treatment periods compared to cells treated with vehicle (DMSO). Log 2 fold change versus-log 10 p value. Dotted lines along x-axis represent±log 2 (2) fold change and dotted line along y-axis represents-log 10 (0.05). Metabolites±log 2 (2) fold change shown as red dots with metabolite names denoted. All other metabolites are black dots. G6P, glucose-6-phosphate; F 1,6-BP, fructose 1,6-bisphosphate; DHAP, dihydroxyacetone phosphate; 6PGA, 6-phosphogluconic acid; R5P, ribose 5-phosphate; E4P, erythrose-4-phosphate. Data represented as mean with n=3 biological replicates. (FIG. 4B) Upper glycolysis metabolites and pentose phosphate pathway decrease after 30 min or 6 h treatments with RgA; In all graphs, Error bars represent s.d.; data are mean±s.d . . . . P value is from two-sided student t-test. * means p<0.0001;  means p<0.001. (c) RgA activates AMPK and inhibits S6K in MCF-7 cells. MCF-7 cells were treated with RgA for the different time (left) or different concentration (right), and cell lysates were subjected to Western blot analysis with the indicated antibodies;

FIG. 5A, FIG. 5B, FIG. 5C, and FIG. 5D demonstrate that RgA induces G1 cell cycle arrest and cell apoptosis. (FIG. 5A) RgA inhibits cell cycle progression in the G1 phase. MCF-7 were incubated with DMSO, 5 μM of RgA, 1 μM of RgA, or 0.2 μM of RgA for 24 h before they were harvested for cell cycle analysis. (FIG. 5B) RgA activates p53 and p21 in MCF-7 cells. MCF-7 cells were treated with different concentration of RgA for 24 h and cell lysates were subjected to Western blot analysis with the indicated antibodies. (FIG. 5C) RgA induces apoptosis in MCF-7 cells. MCF-7 cells were treated with different concentration of RgA for 72 h and cell lysates were subjected to Western blot analysis with the indicated antibodies. (FIG. 5D) A proposed mechanism for the anticancer activity of RgA;

FIG. 6A, FIG. 6B, FIG. 6C, and FIG. 6D demonstrate the effect of RgA on the growth of human breast cancer xenografts in mice. (FIG. 6A) Inhibition of cell proliferation in A549, HCC1954, and MCF-7 cells by RgA. Analysis of tumor volume index (FIG. 6B), tumor weight (FIG. 6C), and body weight (FIG. 6D). Twelve female NSG mice (n=6 mice per group) bearing MCF-7, ER+/HER2− human breast cancer cells, were injected intraperitoneally with vehicle or RgA (2 mg/kg) every day. The tumor volume index was calculated as a ratio of the tumor volume on a given day divided by the tumor volume of day 0. Error bars represent s.d.; data are mean±s.d.; p=0.0012 vs vehicle control (b); p=0.0021 vs vehicle control (c); P value is from two-sided student t-test;

FIG. 7 show representative surface chemistry of the presently disclosed 3D microarray;

FIG. 8 is a comparison on the ratios of signal-to-background (SBR) was made from FIG. 1B. Error bars represent s.d.; data are mean±s.d.; n=2 independent experiments;

FIG. 9 is a comparison of the interaction between rapafucins and FKBP12 on 3D and 2D surfaces. Quantification of signals using signal-to-background ratio (SBR). Error bars represent s.d.; data are mean±s.d.; n=2 independent experiments;

FIG. 10 shows GLUT1, GLUT3, and GLUT4 protein levels of HEK 293T wild type (WT) and over-expressed (OE) cells analyzed by Western blotting. Representative image of n=2 independent experiments with similar results;

FIG. 11A, FIG. 11B, and FIG. 11C show the comparison of 3D (FIG. 11A) and 2D (FIG. 11B) surface and the JW11-D2 and GLUT1 binder found. The SBR of JW11-D2 on 3D surface is 7.0, while the SBR of JW11-D2 on 2D surface is 1.9 under the same condition. Representative image of n=3 independent experiments with similar results. (FIG. 11C) The histograms of SBR of 3918 rapafucin compounds against GLUT1 from the 3D microarray screening. Numbers in the x-axis were referred to compound entry # according to the decoding table in Table 1. Representative hits (SBR>3) and their compound # are shown on top of each histogram, and colored in red;

FIG. 12 shows inhibition of [3H]-2DG uptake in human red blood cells and sealed erythrocyte membranes by JW11-D2. Error bars represent s.d.; data are mean±s.d.; n=3 independent experiments;

FIG. 13A and FIG. 131B show (FIG. 13A) structure of Biotin-RgA; (FIG. 13B) inhibition of [3H]-2DG glucose uptake in A549 cells by Biotin-RgA. Error bars represent s.d.; data are mean±s.d.; n=3 independent experiments;

FIG. 14 shows the activity of RgA is not FKBP-dependent. Inhibition of [3H]-2DG uptake in Jurkat T wild type (WT), FKBP12 knock out (KO), FKBP51 knock out (KO), and FKBP52 knock out (KO) cells by RgA. Error bars represent s.d.; data are mean±s.d.; n=3 independent experiments;

FIG. 15A, FIG. 15B, and FIG. 15C show that TCA cycle metabolites (FIG. 15A) and Redox status (FIG. 15B), but not Energy status (FIG. 15C), were unaffected after 30 min or 6 h treatments with RgA in MCF-7 cells. GSH, reduced glutathione; GSSG, oxidized glutathione. Error bars represent s.d.; data are mean±s.d.; n=3 independent experiments. P value is from two-sided student t-test; ** means p<0.001;

FIG. 16 is a summary of the % of cells in each phase of the cycle. MCF-7 were incubated with DMSO, 5 μM of RgA, 1 μM of RgA, or 0.2 μM of RgA for 24 h before they were harvested for cell cycle analysis. Error bars represent s.d.; data are mean±s.d.; n=3 independent experiments;

FIG. 17 shows the effect of RgA on the growth of human breast cancer xenografts in mice. Analysis of tumor volume (a) and body weight (b). Twelve female athymic nude mice (BALB/c, nu/nu-NCr) (n=6 mice per group) bearing HCC1954, HER2-positive human breast cancer cells, were injected intraperitoneally with vehicle or RgA (2 mg/kg) every day; The tumor volume index was calculated as a ratio of the tumor volume on a given day divided by the tumor volume of day 0. Error bars represent s.d.; data are mean±s.d.; p=0.0005 vs vehicle control; P value is from two-sided student t-test;

FIG. 18 shows chemical structures of FKBD10, FKBD11, FKBD12, FKBD13, and FKBD14;

FIG. 19 is a representative NMR spectrum of RgA;

FIG. 20 is an LC-MS spectrum of biotinylated JW11-D2 (biotin-RgA);

FIG. 21 is a scheme depicting application of an ethacrynic acid linker to a surface initiated polymerization (SIP) 3D surface;

FIG. 22 is a scheme depicting horizontal density optimization where initiator density is controlled by a spacer;

FIG. 23 shows calcineurin detection from different initiator ratios:

FIG. 24 shows ratios of initiator compared by calcineurin detection;

FIG. 25 shows mTOR detection from different initiator ratios;

FIG. 26 shows ratios of initiator comparison for mTOR detection;

FIG. 27 shows that a higher ratio of DMAEMA increases the immobilization amount in high concentration of protein;

FIG. 28 shows a Huprot microarray on a 3D-EA surface;

FIG. 29 is a comparison of the 2D-EA and 3D-EA surface;

FIG. 30 is a comparison of the PATH and 3D-EA surface;

FIG. 31 shows H105 lysate containing CRYBB2+CRY882 ab (upper) and H106 BSA+CRYBB2 ab (lower);

FIG. 32 shows the ratios between lysate group and negative;

FIG. 33 shows the ratio between lysate and negative (upper) and signal-to-noise of CRYBB2 lysate and CRY882 antibody and BSA and CRYBB2 antibody (negative);

FIG. 34 shows spot screening of CRYBB2 and control;

FIG. 35 is a rapafucin microarray printing (real chip);

FIG. 36 is schematic depicting an FKBP12 displaying rapafucin microarray;

FIG. 37 is a comparison between a PATH surface and 3D-EA-rapafucin microarray for anti-GST antibody detection;

FIG. 38 is a FKBP12 displaying rapafucin microarray and its screening on endogens mTOR streptavidin and Glut1, respectively, is illustrated. Rapamycin induced a specific binding between FKBP12 and mTOR. Biotinylated rapafucin induced a specific binding between FKBP12 and streptavidin. FK506 induced a specific binding between FKBP12 and calcineurin;

FIG. 39 is a comparison between PATH surface and 3D-EA-rapafucin microarray for calcineurin;

FIG. 40 is a comparison between PATH surface and 3D-EA-rapafucin microarray for mTOR;

FIG. 41 is a microarray comprising rapafucins displayed by FKBP12, FKBP51 and FKBP52, respectively, for anti-FKBP12, anti-FKBP51 and anti-FKBP52 antibodies detection;

FIG. 42 is mTOR detection;

FIG. 43 is calcineurin detection;

FIG. 44 is calcineurin results analysis;

FIG. 45 is sensitivity evaluation by storage conditions; and

Figure 46:
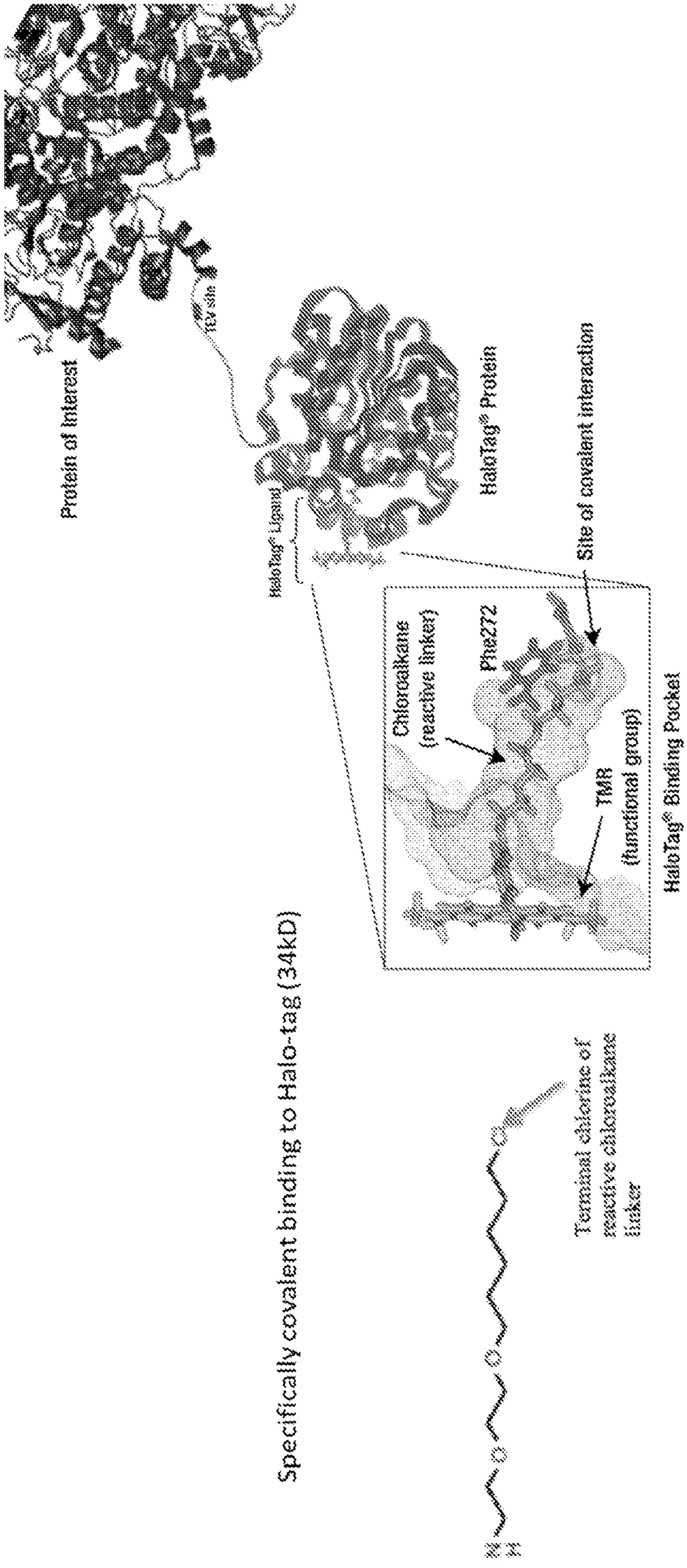

FIG. 46 is an embodiment of a surface strategy.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Three-Dimensional Surface for Protein and Small Molecule Microarrays

In some embodiments, the presently disclosed subject matter provides a three-dimensional microarray comprising a surface-modified substrate having one or more polymer chains attached thereto, wherein the one or more polymers chains have one or more diazirine functional groups bound thereto, and wherein the one or more diazirine functional groups have one or more rapafucins covalently bound thereto, wherein the one or more rapafucins are disclosed in WO/2017/136708, for Synthesis and Composition of Rapafucin Libraries, to Liu et al., published Aug. 10, 2017, U.S. Patent Application No. US20190092808 for Synthesis and Composition of Rapafucin Libraries, to Liu et al., published Mar. 28, 2019, and Guo et al., *Nat. Chem.* 2019, 11, 254-263, each of which are incorporated herein by reference in their entirety.

In particular embodiments, the one or more rapafucins are selected from compound A or compound E presented immediately herein below, each of which is disclosed in WO/2017/136708 and US20190092808:

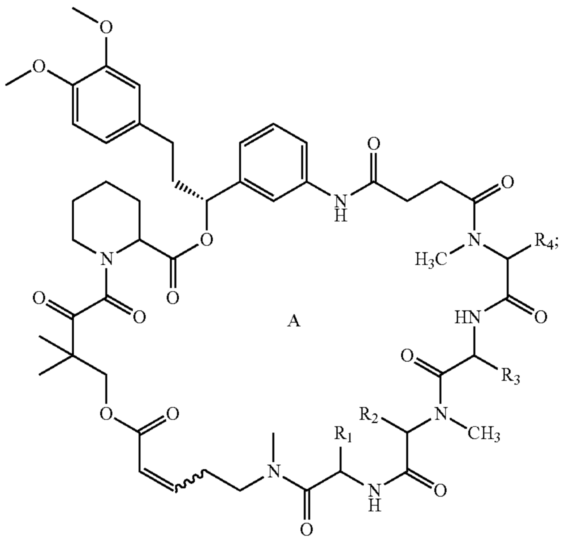

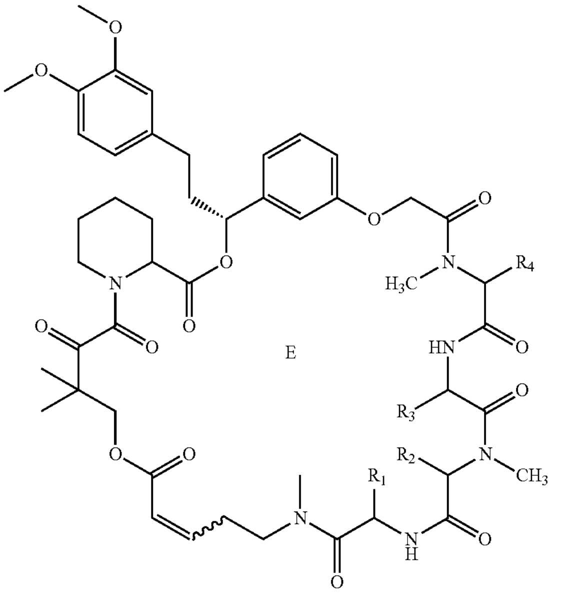

wherein $R_1$ and $R_3$ are selected from:

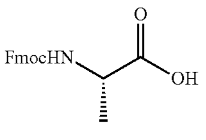

Ala

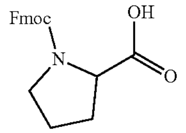

Pro

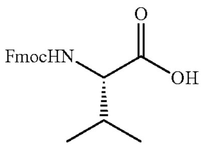

Val

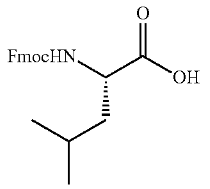

Leu

-continued

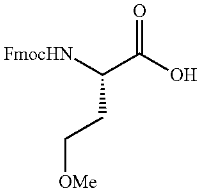

HoSerMe

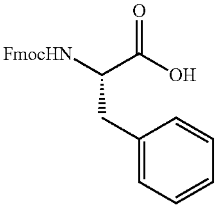

Phe

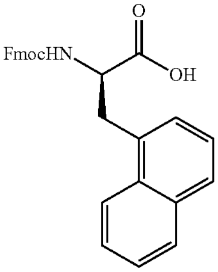

NaI

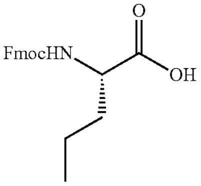

Nva

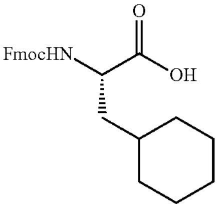

ChA

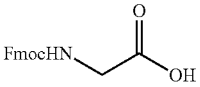

Gly

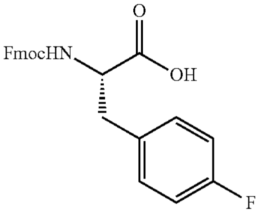

PhF

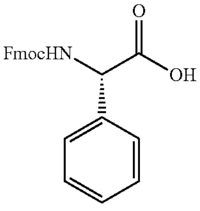

PhG

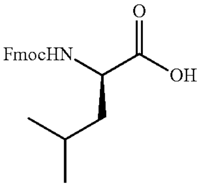

dLeu

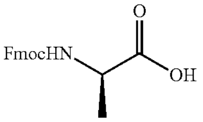

dAla and

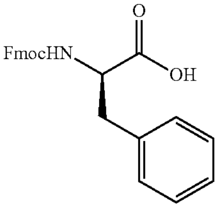

dPhe $R_2$ and $R_4$ are selected from:

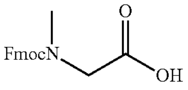

MGly

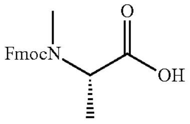

mAla

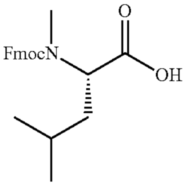

mLeu

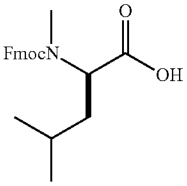

mdLeu

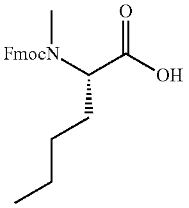

mNle

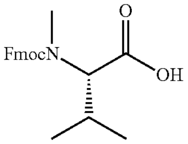

mYal

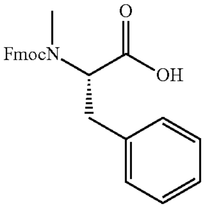

mPhe

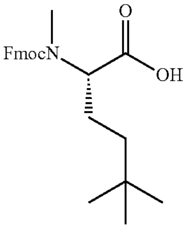

mSerBu

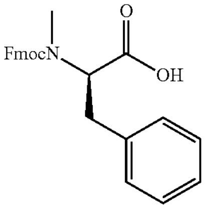

mdPhe

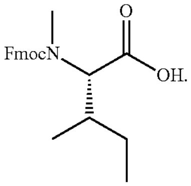

mIle

Other suitable libraries are disclosed in U.S. Patent Application Publication No. US20140073581 for Hybrid Cyclic Libraries and Screens Thereof, to Liu et al., published Mar. 13, 2014, which is incorporated herein by reference in its entirety.

In particular embodiments, the surface-modified substrate comprises one or more amine functional groups. In certain embodiments, the surface-modified substrate comprises a glass substrate.

In some embodiments, the one or more diazirine functional groups comprise a moiety having the following general structure, wherein $R_1$ and $R_2$ can be aryl, e.g., phenyl, or $CF_3$.

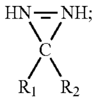

In particular embodiments, the one or more diazirine functional groups comprise a trifluoromethylphenyl diazirine moiety.

In some embodiments, the one or more polymer chains comprise an initiator and a spacer. In particular embodiments, the one or more polymer chains comprise a halogenated carboacyl group. As used herein, a "carboacyl" group has the general structure of —C(═O)—R. In some embodiments, R can be a halogen. In particular embodiments, the halogenated carboacyl group is selected from 2-bromoisobutyryl bromide and propionyl bromide. In certain embodiments, the propionyl bromide is a spacer on the surface-modified substrate.

In some embodiments, the 2-bromoisobutyryl bromide and propionyl bromide are present in a predetermined molar ratio. In representative embodiments, the predetermined molar ratio of 2-bromoisobutyryl bromide to propionyl bromide has a range from about 1:10, 1:15, 1:20, 1:30; 1:40, 1:50, 1:60, 1:70, 1:80, 1:90; 1:100, 1:110; 1:120, 1:130, 1:140, and 1:150. In particular embodiments, the predetermined molar ratio comprises about a 1:100 ratio of 2-bromoisobutyryl bromide to propionyl bromide.

In certain embodiments, the presently disclosed three-dimensional array further comprises a linker group positioned between the one or more polymers chains and the one or more diazirine functional groups. In particular embodiments, the linker comprises a polyethylene glycol (PEG). In more particular embodiments, the linker comprises a poly-(PEGMA-co-DMAEMA) copolymer matrix. In certain embodiments, the PEGMA-to-DMAEMA has a ratio of about 16:2, 12:2, 8:2, 4:2, and 2:2. In more certain embodiments, the PEGMA-to-DMAEMA has a ratio of about 8:2.

In some embodiments, the presently disclosed subject matter provides a three-dimensional array, wherein the surface-modified substrate comprises a scaffold having the following molecular structure:

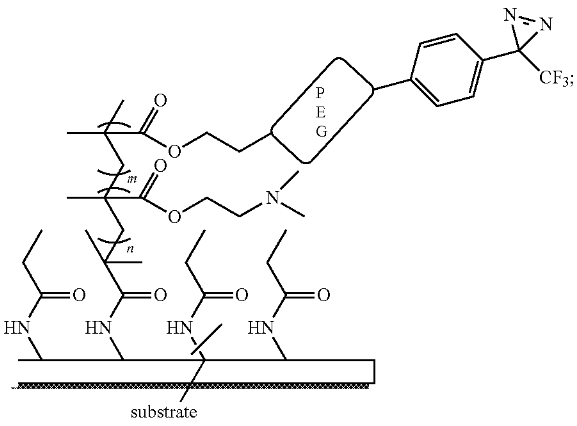

wherein m and n are each independently an integer from 1 to 1000.

In certain embodiments, the presently disclosed three-dimensional array further comprises a library of small molecules printed on one or more locations on the surface, wherein the library of small molecules are immobilized to the surface through photocrosslinking to the diazirine functional groups.

In other embodiments, the presently disclosed subject matter provides a method of generating a three-dimensional microarray comprising a library of small molecules, the method comprising:

providing a surface-modified substrate having one or more polymer chains attached thereto, wherein the one or more polymers chains have one or more diazirine functional groups bound thereto;

providing a library of small molecules in a solvent carrier;

printing the library of small molecules in the solvent carrier onto the surface;

evaporating substantially all of the solvent carrier from the surface; and exposing the printed library of small molecules to UV light of an appropriate wavelength to cause crosslinking of the small molecules to the surface through photoactivation of the one or more diazirine functional groups into one or more reactive carbene species.

In yet other embodiments, the presently disclosed subject matter provides a method of screening the presently disclosed three-dimensional microarray, the method comprising:

exposing the three-dimensional microarray to a cell lysate expressing a protein of interest (POI) or purified recombinant POI;

washing the three-dimensional microarray to remove unbound protein; and detecting a POI bound to a specific small molecule by using a fluorescently labeled primary antibody against the POI or a tag that is fused to the POI, wherein the specific small molecule bound to the POI is identified by a predetermined location of the specific small molecule.

In yet other embodiments, the presently disclosed subject matter provides a three-dimensional array comprising a surface-modified substrate having one or more polymer chains attached thereto, wherein the one or more polymer chains have one or more ethacrynic acid (EA) moieties bound thereto, the structure of EA is provided immediately herein below:

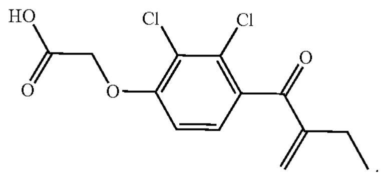 [SMILES: C=C(CC)C(=O)c1ccc(OCC(=O)O)c(Cl)c1Cl]

In particular embodiments of the presently disclosed three-dimensional array, the scaffold has the following molecular structure:

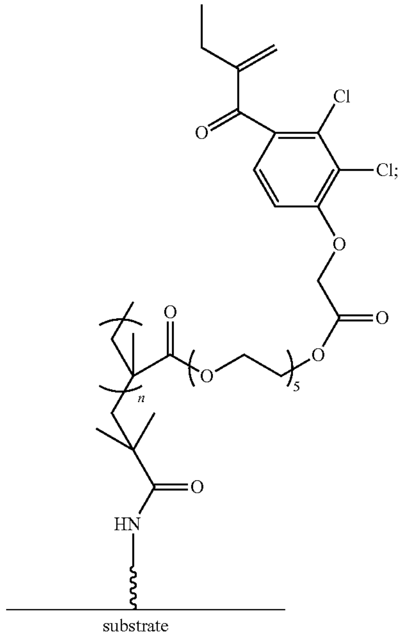

wherein n is an integer from 1 to 1000.

In certain embodiments, the three-dimensional microarray further comprises a library of human proteome printed thereon, wherein each protein of the human proteome is fused to glutathione S-transferase (GST) through interaction of GST with the one or more ethacrynic acid moieties bound to the one or more polymer chains.

In other embodiments, the three-dimensional microarray further comprises a covalent protein-ligand pair comprising a covalent bond between an immobilized small molecule ligand and its corresponding fusion tag of a protein of interest (POI), wherein the fusion tag is selected from a haloTag, a SNAP-tag, and a CLIP-tab.

In other embodiments, the presently disclosed subject matter provides a method of screening the EA three-dimensional microarray for new protein-protein, protein-nucleic acid and protein-small molecule interactions, the method comprising contacting the three-dimensional microarray with one or more proteins, nucleic acids, or small molecules of interest.

In yet other embodiments, the presently disclosed subject matter provides a method for identifying a glucose transporter inhibitor, the method comprising contacting a presently disclosed three-dimensional microarray(s) with one or more cells expressing a glucose transporter protein, wherein the glucose transporter protein binds to one or more rapafucins of the three-dimensional microarray, and detecting the bound glucose transporter protein.

In certain embodiments, the glucose transporter protein is selected from GLUT1, GLUT3, and GLUT4. In more certain embodiments, the glucose transporter protein is GLUT1.

In other embodiments, the presently disclosed subject matter provides a glucose transporter inhibitor identified by the presently disclosed methods.

In yet other embodiments, the presently disclosed subject matter provides a method for treating a disease, condition, or disorder associated with one or more glucose transporters, the method comprising administering to a subject in need of treatment thereof a therapeutically effective amount of a glucose transporter inhibitor or a pharmaceutically effective salt thereof.

In certain embodiments, the administration of the glucose transporter inhibitor inhibits glucose uptake.

In certain embodiments, the administration of the glucose transporter inhibitor induces cell apoptosis.

In certain embodiments, the administration of the glucose transporter inhibitor inhibits tumor growth.

In particular embodiments, the disease, disorder, or condition is a cancer. In more particular embodiments, the cancer is breast cancer.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments±50%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Discovery of a Potent GLUT Inhibitor Using Rapafucin 3D Microarrays

1.1 Overview

Glucose transporters, including glucose transporter 1 (GLUT1), play an essential role in cancer cell proliferation and survival and have been pursued as promising cancer drug targets.

In some aspects, the presently disclosed subject matter includes microarrays of a new macrocycle library known as rapafucins, which are related to rapamycin, and use of the rapafucin three-dimensional (3D) microarrays for screening for new inhibitors of GLUT1. In representative results, multiple hits from the rapafucin 3D microarray were identified. One hit was confirmed as a bona fide GLUT1 ligand, named Rapaglutin A (RgA).

In other aspects, the presently disclosed subject matter demonstrates that RgA is a potent inhibitor of GLUT1, as well as GLUT3 and GLUT4, with a low nanomolar $IC_{50}$ value for GLUT1. RgA was found to inhibit glucose uptake, which led to a decrease in cellular ATP synthesis, activation of AMP-dependent kinase, inhibition of mTOR signaling, and induction of cell cycle arrest and apoptosis in cancer cells. Moreover, RgA was capable of inhibiting tumor xenografts in vivo without apparent side effects. RgA is a new chemical tool to study GLUT function and a promising lead to develop anticancer drugs.

1.2 Results and Discussion

A library of macrocycles named rapafucins that are related to the natural products rapamycin and FK506 was generated. The premise of the rapafucin design is to exploit the FKBP-binding domain of rapamycin and FK506 that confers favorable cellular and pharmacokinetic advantages and use it as a key scaffold to display non-natural oligopeptides in place of the effector domains of rapamycin and FK506. The ability of rapafucins to bind FKBP proteins to form a tight complex confers a number of advantages as drug leads, including greater stability, higher intracellular accumulation, larger size and superior pharmacokinetic and pharmacodynamic properties. Yang et al., *Nature* 2013, 497, 217-223; Griffith et al., *Cell* 1995, 82, 507-522; Kissinger et al., *Nature* 1995, 378, 641-644; and Marinec et al., *Proc. Natl. Acad. Sci. USA* 2009, 106, 1336-1341.

More particularly, a 45,000-compound rapafucin library was designed and synthesized. Guo et al., *Nat. Chem.* 2019, 11, 254-263. Promising hits against several targets were identified, including a potent and isoform-specific inhibitor of the human equilibrative nucleoside transporter (hENT) 1 that showed in vivo efficacy in an animal model of ischemic kidney reperfusion injury. Guo et al., *Nat. Chem.* 2019, 11, 254-263. Given that hENT1 and GLUT belong to the same superfamily of solute carrier transporters, the rapafucin library was screened for new GLUT1 inhibitors.

Accordingly, in some embodiments, a 3D small molecule microarray was developed by immobilizing 3,918 rapafucins on a single chip. Cell lysates containing stably expressed GLUT1 were screened against this microarray. A potent inhibitor, named rapaglutin A (RgA), was identified that inhibited GLUT1, as well as GLUT3 and GLUT4. RgA also inhibited glucose uptake, induced cell apoptosis, and inhibited the growth of tumor xenografts of breast cancer cells in vivo.

Small molecule microarrays have been shown to be a powerful platform for high-throughput screening. Foong et al., *Curr. Opin. Chem. Biol.* 2012, 16, 234-242; Hong et al., *Curr. Opin. Chem. Biol.* 2014, 18, 21-28; and Uttamchandani and Yao, *Methods Mol. Biol.* 2017, 1518, 1-17. Among the different methods of small molecule immobilization, preassembled diazirine that upon activation by UV light generates a reactive carbene species to covalently react with and capture small molecules was used in the presently disclosed design. As macrocycles, rapafucins are particularly suitable for this platform as multiple sites for immobilization exist around the periphery of the macrocycles. Given the stochastic nature of the carbene-mediated crosslinking reaction, there is a high probability that a fraction of a given rapafucin species will be covalently immobilized via positions that would not interfere with its binding to target protein. To develop a rapafucin microarray for high-throughput screening, both 2D and 3D surface structures prefabricated on glass slides were explored (FIG. 1A).

Unlike the 2D surface structure, Kanoh et al., *Angew. Chem. Int. Ed. Engl.* 2003, 42, 5584-5587; Miyazaki et al., *Nat. Chem. Biol.* 2010, 6, 667-673, the 3D surface structure was fabricated by growing polymers on the glass surface with each polymeric chain carrying up to hundreds of trifluoromethylphenyl diazirine moieties, significantly increasing the number of sites for rapafucin immobilization on the 3D surface and at the same time providing a biocompatible environment for rapafucin-protein interactions (FIG. 1A, FIG. 7). Barbey et al., *Chem. Rev.* 2009, 109, 5437-5527; Lee et al., *Biomacromolecules* 2004, 5, 877-882.

To develop the 3D surface for rapafucin microarray fabrication, the polymer density was optimized both horizontally and vertically to achieve the highest sensitivity. Horizontal density was controlled by mixing 2-bromoisobutyryl bromide and propionyl bromide (as the spacer) at different molar ratios to control the density of active atom transfer radical polymerization (ATRP) initiation sites as previously described. Barbey et al., *Chem. Rev.* 2009, 109, 5437-5527; Ma et al., *ACS Appl. Mater. Interfaces* 2010, 2, 3223-3230; Lee et al., *Biomacromolecules* 2004, 5, 877-882.

A 1:100 ratio of 2-bromoisobutyryl bromide and propionyl bromide was applied to the 3D surface without further optimization as this ratio is commonly used to achieve high sensitivity of 3D surface. Barbey et al., *Chem. Rev.* 2009, 109, 5437-5527; Lee et al., *Biomacromolecules* 2004, 5, 877-882. Vertical density was manipulated using a poly-(PEGMA-co-DMAEMA) matrix to maximize the binding of proteins to adjacent ligands displayed on the same polymer. The vertical density was optimized by adjusting the gradient ratio of monomer PEGMA and DMAEMA followed by determination of binding of FKBP12 to the resultant 3D surface as all rapafucins contain an embedded FKBP-binding domain. The highest signal-to-background ratio (SBR) was obtained at a PEGMA-to-DMAEMA ratio of 8:2 (FIG. 1B, FIG. 8). Using this optimized diazirine-containing 3D surface grafted on a glass slide, a rapafucin library, Guo et al., *Nat. Chem.* 2019, 11, 254-263, containing 3,918 individual compounds to the glass was robotically arrayed. As a comparison, the same 3,918 individual rapafucins also were arrayed on a 2D surface grafted slide displaying the same diazirine as previously described. Kanoh et al., *Angew. Chem. Int. Ed. Engl.* 2003, 42, 5584-5587; Miyazaki et al., *Nat. Chem. Biol.* 2010, 6, 667-673.

Once stock solutions of the rapafucin library were arrayed on the 2D or 3D surface and most of solvent carrier was evaporated, the crosslinking reaction was initiated by irradiating the surfaces with 365-nm wavelength UV light. Kawatani and Osada, *Medchemcomm* 2014, 5, 277-287. Next, the 2D and the newly developed 3D surface were compared for their capacity to bind FKBP12 under the same conditions, the SBR of the binding of FKBP12 on the 3D surface is on average 6-fold greater than that on the 2D surface (FIG. 1C, FIG. 9), indicating that the 3D microarray of rapafucins is a superior platform for screening target proteins. To screen for GLUT1-interacting rapafucins, GLUT1 was stably overexpressed in HEK293T cells and generated cell lysates containing detergent-solubilized recombinant GLUT1 (FIG. 10). The GLUT1-containing cell lysate was then incubated on both 2D and 3D rapafucin microarrays. After washing the slides to remove unbound proteins, the bound GLUT1 protein was detected with anti-GLUT1 antibodies, followed by visualization with Cy5-labeled secondary antibodies using a microarray scanner. Rapafucins were scored as positive hits when the corresponding SBR was greater than 3. Based on this criterion, a total of 17 rapafucin hits and one positive control BAY-876, a specific GLUT1 inhibitor, Siebeneicher et al., *ChemMedChem* 2016, 11, 2261-2271, were identified on the 3D rapafucin microarray. In contrast, only one hit (WL13-F11, also among the 17 hits identified from the 3D rapafucin microarray) was identified on the 2D rapafucin microarray (Table 1, FIG. 11).

TABLE 1

Validation of GLUT1 microarray hits using [3H]-2DG uptake assay in A549 cells.

| Entry | Name | Residue 1 | Residue 2 | Residue 3 | Residue 4 | FKBD | 3D SBR | 2D SBR | $IC_{50}$ (nM) |
|---|---|---|---|---|---|---|---|---|---|
| 1 | WL13-F11 | LysAc | mSertbu | Phe-4-NH2 | mLeu | FKBD11 | 12.4 ± 4.9 | 6.4 ± 2.4 | >3000 |
| 2 | JW15-E6 | mGly | Phe | Phe | mGly | FKBD3 | 10.6 ± 0.7 | <3.0 | >3000 |
| 3 | WL12-G5 | dPro | mVal | PheNO2 | mGly | FKBD11 | 8.8 ± 2.0 | <3.0 | >3000 |
| 4 | HP05-F5 | dPhe | mIle | PhF | mGly | FKBD11 | 7.9 ± 2.6 | <3.0 | >3000 |
| 5 | HP08-C2 | dPro | Pyr | PhF | mGly | FKBD11 | 7.3 ± 2.6 | <3.0 | >3000 |
| 6 | JW11-D2 | Gly | mIle | dPhe | mLeu | FKBD10 | 6.5 ± 1.4 | <3.0 | 11.6 ± 1.8 |
| 7 | JW01-C6 | mLeu | dPro | mPhe | Pyr | FKBD10 | 6.5 ± 1.7 | <3.0 | >3000 |
| 8 | WL05-D8 | mPhe | β-Ala | mGly | Tyr | FKBD11 | 6.4 ± 1.8 | <3.0 | >3000 |
| 9 | WL11-E6 | dPro | mNle | Phe-4-NH-Boc | nGly | FKBD11 | 5.4 ± 0.3 | <3.0 | >3000 |
| 10 | WL03-G11 | Gly | mGly | Tyr | dmPhe | FKBD11 | 5.1 ± 0.7 | <3.0 | >3000 |
| 11 | HP16-H5 | dTyrOH | mGly | dTyrOH | mTyrOH | FKBD11 | 5.0 ± 1.1 | <3.0 | >3000 |
| 12 | WL11-G11 | dPro | mNle | Phe | mGly | FKBD13 | 4.9 ± 1.8 | <3.0 | >3000 |
| 13 | WL11-E7 | dPro | mNle | D-Phe-4-NH-Boc | mGly | FKBD11 | 4.8 ± 0.5 | <3.0 | >3000 |
| 14 | HP17-C2 | Pro | mSerBu | PhG | mAla | FKBD14 | 4.2 ± 0.4 | <3.0 | 243.2 ± 42.5 |
| 15 | HP12-G3 | Phe | mGly | dPyr | dmLeu | FKBD11 | 4.0 ± 0.5 | <3.0 | >3000 |
| 16 | WL11-G9 | dPro | mNle | Phe | mGly | FKBD12 | 3.9 ± 0.3 | <3.0 | >3000 |
| 17 | HP05-A9 | Phe | mNle | PhF | dmPhe | FKBD10 | 3.4 ± 1.4 | <3.0 | >3000 |
| 18 | BAY876 | | | | | | 3.2 ± 0.74 | <3.0 | |

Error bars represent s.d.; data are mean ± s.d.;
n = 3 independent experiments.

Figure 2:
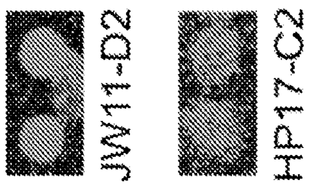
Figure 2:
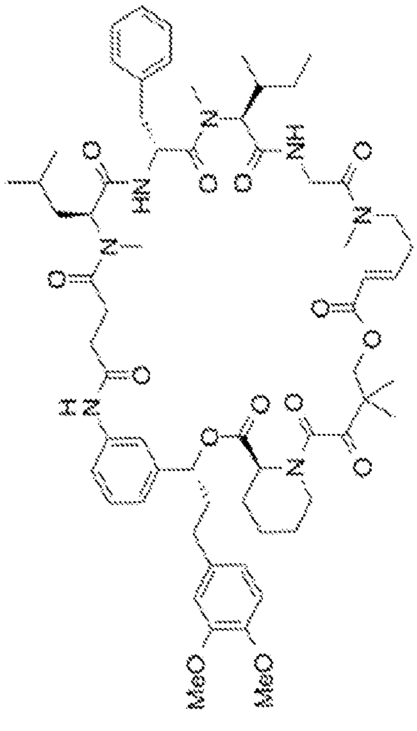
Figure 2:
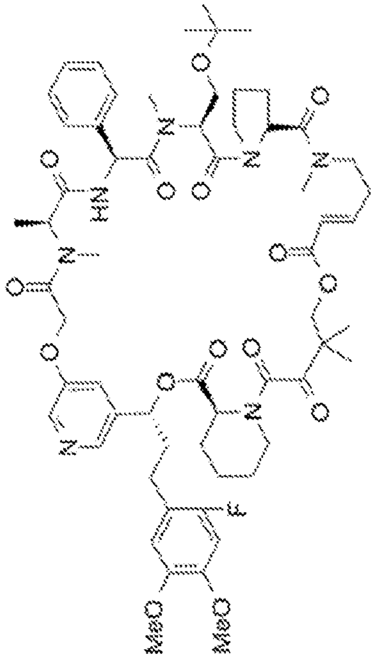
Figure 2:
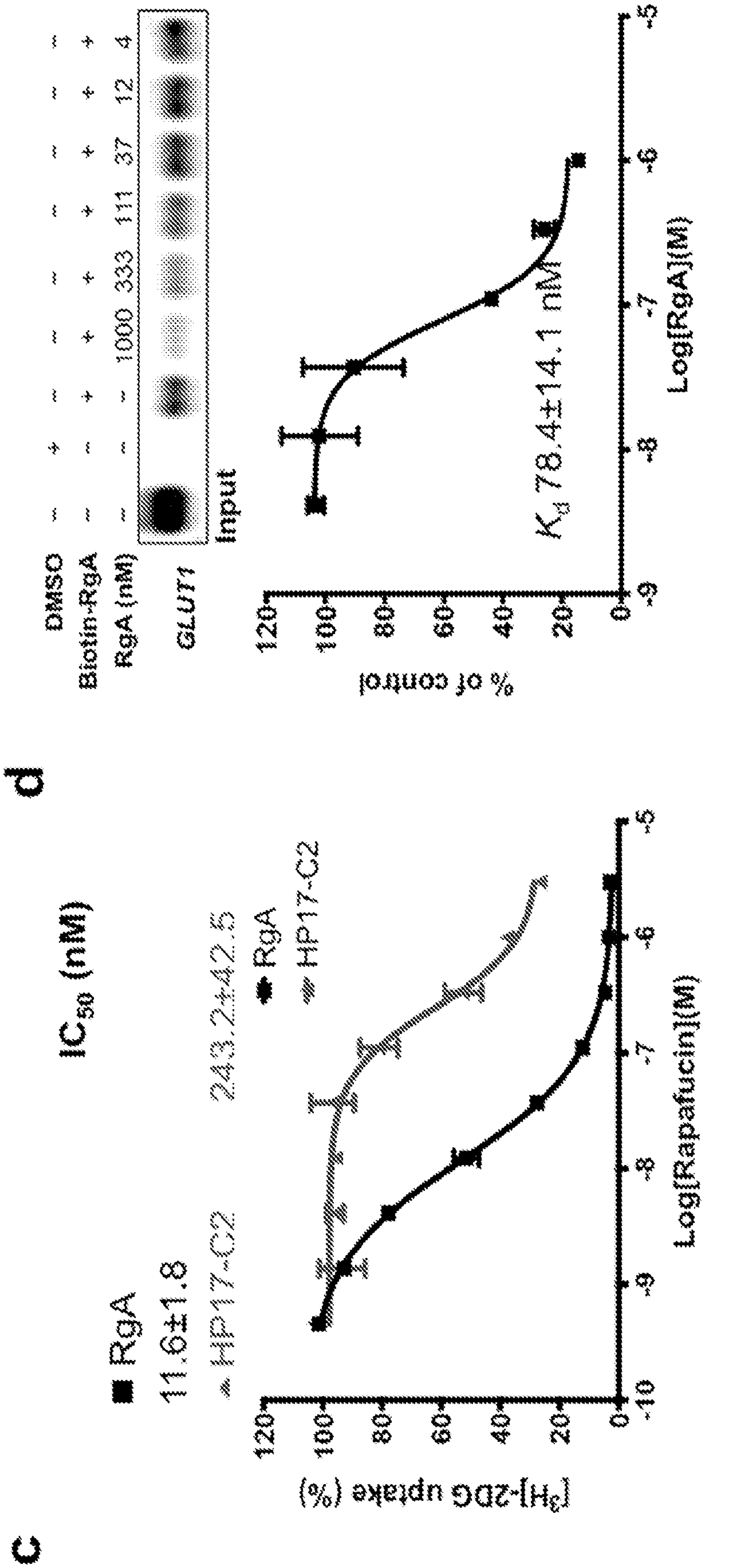

To determine which of the 17 rapafucin hits inhibited the transporter activity of GLUT1, an orthogonal glucose uptake assay using 2-deoxy-D-[3H] glucose ([3H]-2DG), a nonhydrolyzable, radioactive glucose analog, was employed. Each hit was separately incubated with A549 cells for 10 min before the amount of [3H]-2DG taken up by the cells was measured using scintillation counting. Two of the 17 hits, JW11-D2 and HP17-C2 (FIG. 2A and FIG. 2B), were found to block the uptake of [3H]-2DG appreciably with $IC_{50}$ values of 11.6 nM and 243.2 nM, respectively (FIG. 2C, Table 1). The effect of JW11-D2 on uptake of [3H]-2DG in human red blood cells that exclusively express GLUT1 was then determined. Helgerson and Carruthers, *J. Biol. Chem.* 1987, 262, 5464-5475. JW11-D2 showed dose-dependent inhibition of [3H]-2DG uptake into red blood cells and purified sealed erythrocyte membranes with IC50 values of 34.2 nM and 49.5 nM, respectively (FIG. 12), confirming that JW11-D2 is a bona fide GLUT1 inhibitor. To further improve the potency of JW11-D2, a structure-activity relationship (SAR) study was performed by synthesizing 21 new analogs of JW11-D2 using different amino acid building blocks. While a few active analogs were identified, JW11-D2 remained the most potent inhibitor of glucose uptake among the group (Table 2).

TABLE 2

Inhibition of 2-deoxy-D-[3H] glucose (3H-2DG) uptake in A549 cells by JW11-D2 and its analogues. Superscript M indicates N-Me amino acid and D indicates D amino acids used in the sequences.

| Rapafucins | AA sequences | $IC_{50}$ (nM) |
|---|---|---|
| JW11-D2 | Gly-$^{M}$Ile-$^{D}$Phe-$^{M}$Leu | 11.6 ± 1.8 |
| JW11-D2-1 | $^{M}$Gly-$^{M}$Ile-$^{D}$Phe-$^{M}$Leu | >3000 |
| JW11-D2-2 | Pro-$^{M}$Ile-$^{D}$Phe-$^{M}$Leu | >3000 |
| JW11-D2-3 | $^{D}$Pro-$^{M}$Ile-$^{D}$Phe-$^{M}$Leu | >3000 |
| JW11-D2-4 | Gly-$^{M}$Val-$^{D}$Phe-$^{M}$Leu | 30.2 ± 2.3 |
| JW11-D2-5 | Gly-$^{M}$le-$^{D}$Phe-$^{M}$Leu | >3000 |
| JW11-D2-6 | Gly-$^{M}$Phg-$^{D}$Phe-$^{M}$Leu | >3000 |
| JW11-D2-7 | Gly-$^{M}$Nle-$^{D}$Phe-$^{M}$Leu | >3000 |
| JW11-D2-8 | Gly-$^{M}$Nva-$^{D}$Phe-$^{M}$Leu | >3000 |
| JW11-D2-9 | Gly-$^{M}$Leu-$^{D}$Phe-$^{M}$Leu | >3000 |
| JW11-D2-10 | Gly-$^{M}$Ile-$^{D}$hoPhe-$^{M}$Leu | >3000 |
| JW11-D2-11 | Gly-$^{M}$Ile-$^{D}$Pyr-$^{M}$Leu | >3000 |
| JW11-D2-12 | Gly-$^{M}$Ile-$^{D}$PhdiCl-$^{M}$Leu | >3000 |
| JW11-D2-13 | Gly-$^{M}$Ile-$^{D}$Tyr-$^{M}$Leu | >3000 |
| JW11-D2-14 | Gly-$^{M}$Ile-$^{MD}$Phe-$^{M}$Leu | 38.5 ± 4.7 |
| JW11-D2-15 | Gly-$^{M}$Ile-$^{D}$Leu-$^{M}$Leu | >3000 |
| JW11-D2-16 | Gly-$^{M}$Ile-$^{D}$phe-Leu | >3000 |
| JW11-D2-17 | Gly-$^{M}$Ile-$^{D}$Phe-$^{M}$Ile | >3000 |
| JW11-D2-18 | Gly-$^{M}$Ile-$^{D}$Phe-$^{M}$Nva | >3000 |
| JW11-D2-19 | Gly-$^{M}$Ile-$^{D}$Phe-$^{M}$Nle | >3000 |
| JW11-D2-20 | Gly-$^{M}$Ile-$^{D}$Phe-$^{M}$Val | 62.3 ± 5.1 |
| JW11-D2-21 | Gly-$^{M}$Ile-$^{D}$Phe-$^{M}$Phe | >3000 |

Error bars represent s.d.;
data are mean ± s.d.;
n = 3 independent experiments.

Figure 13:
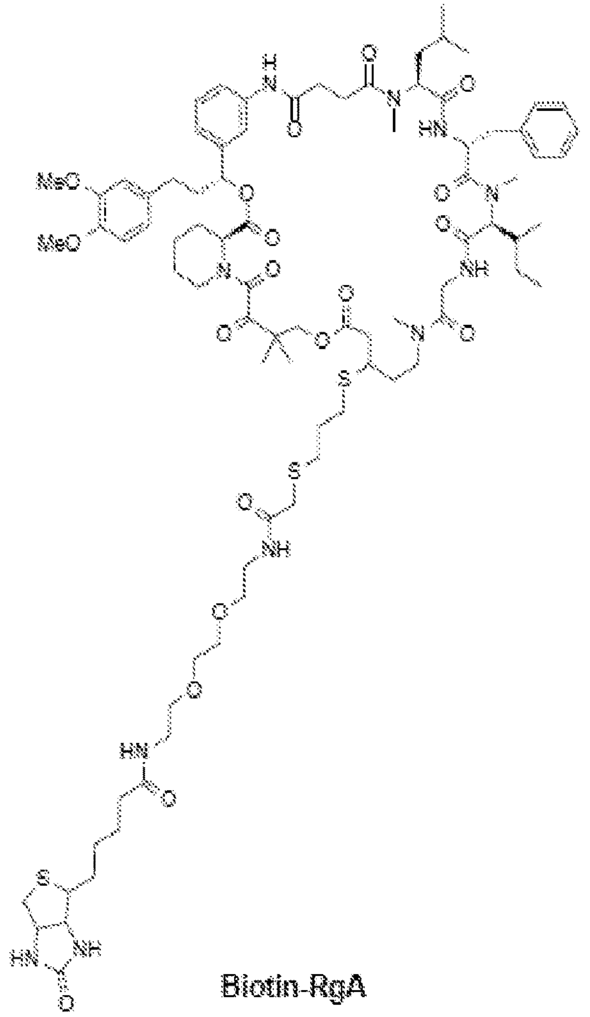
Figure 13:
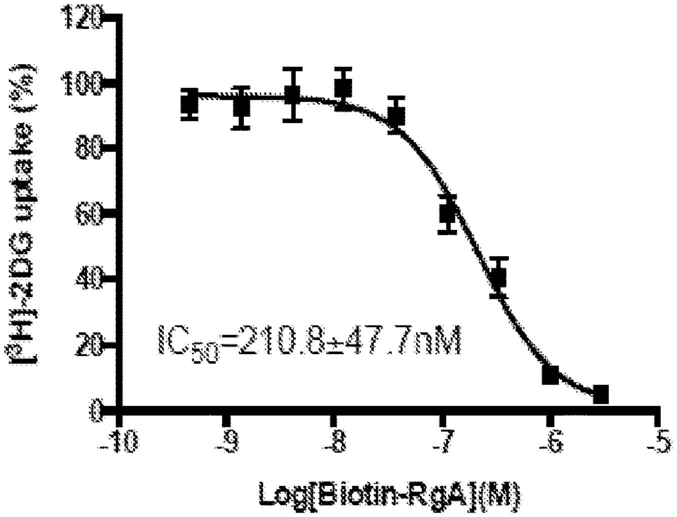

In light of the potent inhibition of glucose uptake by JW11-D2, it was named rapaglutin A (RgA). Next, the binding affinity of RgA for GLUT1 was determined using a RgA biotin pull-down assay. A biotin-RgA conjugate was synthesized by tethering the biotin moiety through carbon: carbon double bond in the FKBP-binding domain of RgA (FIG. 13). An [3H]-2DG uptake assay in A549 cells revealed that biotin-RgA retained inhibitory activity against GLUT1 with an $IC_{50}$ value of 210.8 nM (FIG. 13), suggesting that the biotin-RgA conjugate remained active against GLUT1 albeit with lower potency. Using the biotin-RgA conjugate, a pulldown experiment with cell lysate containing detergent-solubilized GLUT1 protein prepared from HEK293T cells overexpressing GLUT1 was performed, followed by Western blot analysis with a GLUT1-specific antibody. The biotin-RgA conjugate was capable of pulling down GLUT1 (FIG. 2D), further supporting that RgA directly interacts with GLUT1. Importantly, binding of GLUT1 to the biotin-RgA probe is dose-dependently competed by free RgA, allowing for determination of the binding affinity of RgA for GLUT1 with an estimated $K_d$ value of 78 nM (FIG. 2D).

Figure 3:
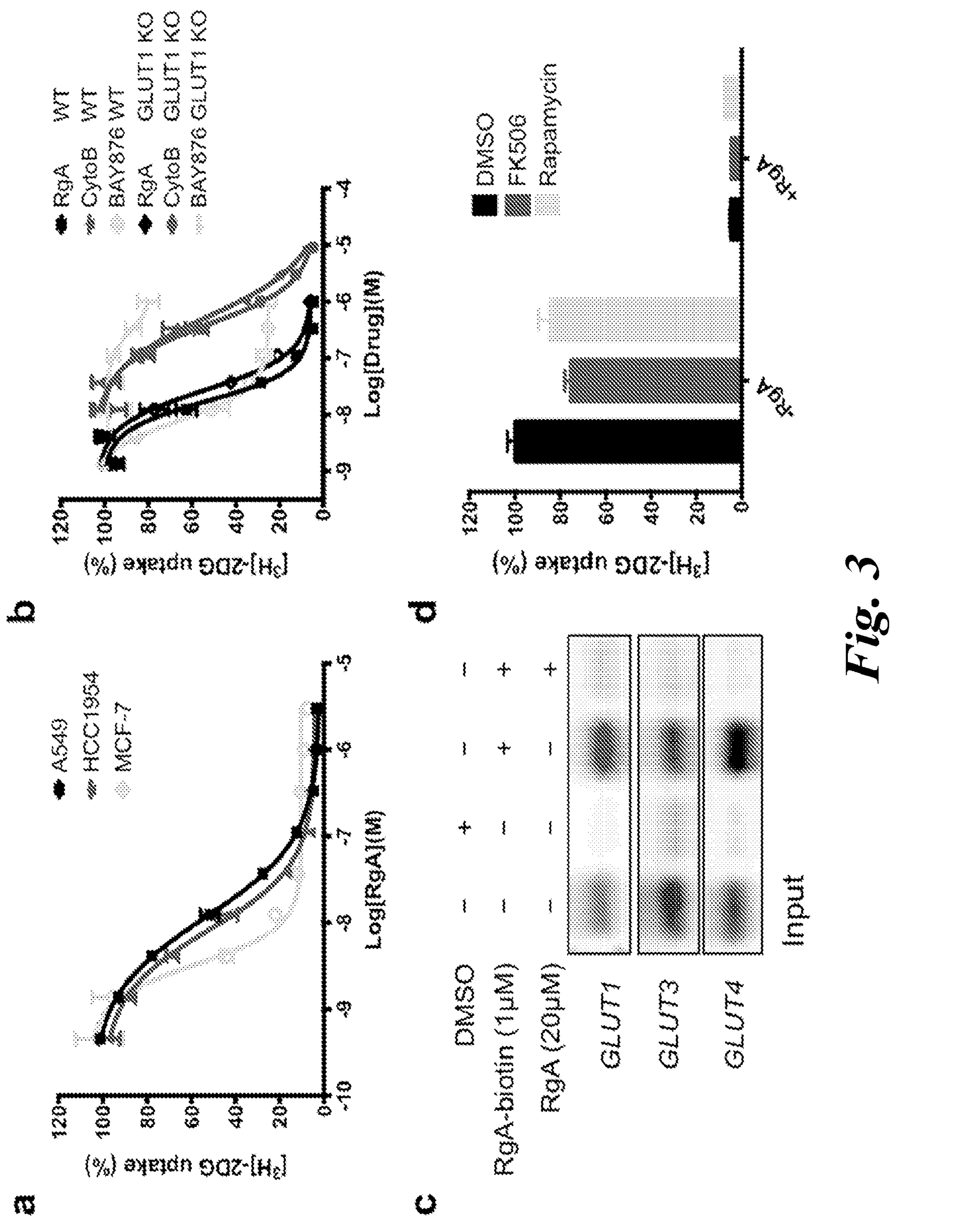

GLUT1 is a basal glucose transporter expressed in almost all cell types, and is upregulated in many cancer cells. Hay, *Nat. Rev. Cancer* 2016, 16, 635-649; Mueckler and Thorens, *Mol. Aspects Med.* 2013, 34, 121-138. To determine whether RgA could inhibit glucose uptake in cancer cell lines in addition to A549, the impact of RgA on [3H]-2DG uptake in six other cancer cell lines, including HCC1954, MCF-7, PANC10.05, Jurkat T, HeLa, and RKO was measured (FIG. 3A, Table 3). RgA dose-dependently inhibited glucose uptake in all cell lines tested with $IC_{50}$ values ranging from 3 nM to 19 nM (Table 3). Among them, breast cancer cell MCF-7 was most sensitive to RgA with an $IC_{50}$ of 3.3 nM. These results demonstrated that RgA has a general inhibitory effect on glucose uptake in all cancer cell lines tested.

TABLE 3

Potency of RgA against the [3H]-2DG uptake assay and the alamar blue assay on different cancer cell lines.

| | A549 | HCC1954 | MCF-7 | PANC 10.05 | Jurkat T | HeLa | RKO |
|---|---|---|---|---|---|---|---|
| $IC_{50}$ (nM) Assay A* | 11.6 ± 1.8 | 8.3 ± 1.9 | 3.3 ± 0.5 | 9.5 ± 1.4 | 10.1 ± 2.1 | 18.9± 2.5 | 10.8 ± 1.5 |
| $IC_{50}$ (nM) Assay B* | 189.3 ± 36.6 | 108.7 ± 17.8 | 87.3 ± 12.7 | 119.2 ± 17.9 | 131.7 ± 24.7 | 280.6 ± 40.1 | 114.5 ± 18.8 |

*Assay A: [H]-2DG uptake assay; Assay B: Alamar blue cell proliferation assay,
Error bars represent s.d.;
data are mean ± s.d.;
n = 3 independent experiments.

The human GLUT family consists of 14 members that differ in substrate affinity, specificity, and tissue distribution. Mueckler and Thorens, *Mol. Aspects Med.* 2013, 34, 121-138. It was further determined whether RgA is specific for GLUT1 using a pair of isogenic cell lines. DLD-1 wild type and DLD-1 GLUT1 knock out cells were treated in parallel with RgA, BAY-876, a reported GLUT1-specific inhibitor, and cytochalasin B, a non-specific GLUT inhibitor, Hellwig and Joost, *Mol. Pharmacol.* 1991, 40, 383-389, followed by assessment of [3H]-2DG uptake. As expected, BAY-876 lost its inhibitory activity, but cytochalasin B maintained its inhibitory activity in GLUT1 knock out cells (FIG. 3B). Similar to cytochalasin B, RgA retained its inhibitory activity in GLUT1 knock out cells, suggesting that RgA, unlike BAY-876, is not specific for GLUT1 (FIG. 3B, Table 4). To further assess the isoform specificity, three other isoforms of glucose transporters, including GLUT2, GLUT3, and GLUT4, were overexpressed in HEK 293T cells and their interaction with RgA was determined using the biotin-RgA pull-down assay. The overexpression of GLUT2 in HEK293T cells did not succeed due to unknown reasons.

TABLE 4

Potency of RgA, BAY-876 and Cytochalasin B against the [3H]-2DG uptake on DLD1 WT and DLD1 GLUT1 knockout cell lines.

| | RgA | BAY-876 | Cytochalasin B |
|---|---|---|---|
| $EC_{50}$ (nM) DLD1 WT | 17.5 ± 2.5 | 8.0 ± 1.1 | 544.9 ± 40.5 |
| $EC_{50}$ (nM) DLD1 GLUT1 KO | 27.1 ± 3.6 | >1000 | 389.8 ± 32.7 |

Error bars represent s.d.;
data are mean ± s.d.;
n = 3 independent experiments.

Similar to the result of GLUT1 pull-down, biotin-RgA was able to pull down both GLUT3 and GLUT4 (FIG. 3C). These results suggest that RgA is a non-specific inhibitor of multiple isoforms of GLUTs, including at least GLUT1, GLUT3, and GLUT4. Like FK506 and rapamycin, RgA contains an FKBP-binding domain. The binding affinity of RgA to different isoforms of FKBP was determined. Interestingly, RgA showed selectivity for different isoforms of FKBPs, with the highest affinity for FKBP12 ($K_i$=1.5 nM for inhibition of the prolyl isomerase activity) (Table 5). The ability of RgA to form a complex with FKBP12 raised the question of whether FKBP is required for its interaction with GLUTs. A hallmark of FKBP dependence is that the cellular effects can be antagonized by other FKBP-binding ligands with no or orthogonal biological activity as has been shown for FK506 and rapamycin. Bierer et al., *Proc. Natl. Acad. Sci. USA* 1990, 87, 9231-9235.

TABLE 5

Inhibition constants of RgA for the peptidyl prolyl cis-trans isomerase activity of different isoforms of FKBP.

| Rapafucin | FKBP12 $K_i$ (nM) | FKSP13 $K_i$ (nM) | FKBP25 $K_i$ (nM) | FKBP51 $K_i$ (nM) | FKBP52 $K_i$ (nM) |
|---|---|---|---|---|---|
| RgA | 1.5 ± 1.1 | 539 ± 207 | >5000 | 46 ± 10 | 32 ± 3 |

Error bars represent s.d.;
data are mean ± s.d.;
n = 3 independent experiments.

High concentration of FK506 and rapamycin had negligible effect on the inhibitory activity of RgA in the [3H]-2DG uptake assay (FIG. 3D). To further determine the dependence of RgA on endogenous FKBP, three major isoforms of FKBP, FKBP12, FKBP51 and FKBP52 were knocked out using CRISPR-Cas9 in Jurkat T cells. Guo et al., *Nat. Chem.* 2019, 11, 254-263. Unlike ENT1 inhibitor rapacodin, Guo et al., *Nat. Chem.* 2019, 11, 254-263, knockout of the three FKBP isoforms showed negligible effects on the sensitivity of cells to RgA (FIG. 14). Taken together, these results strongly suggested that the inhibitory activity of RgA is independent of the endogenous FKBP.

Figure 15:
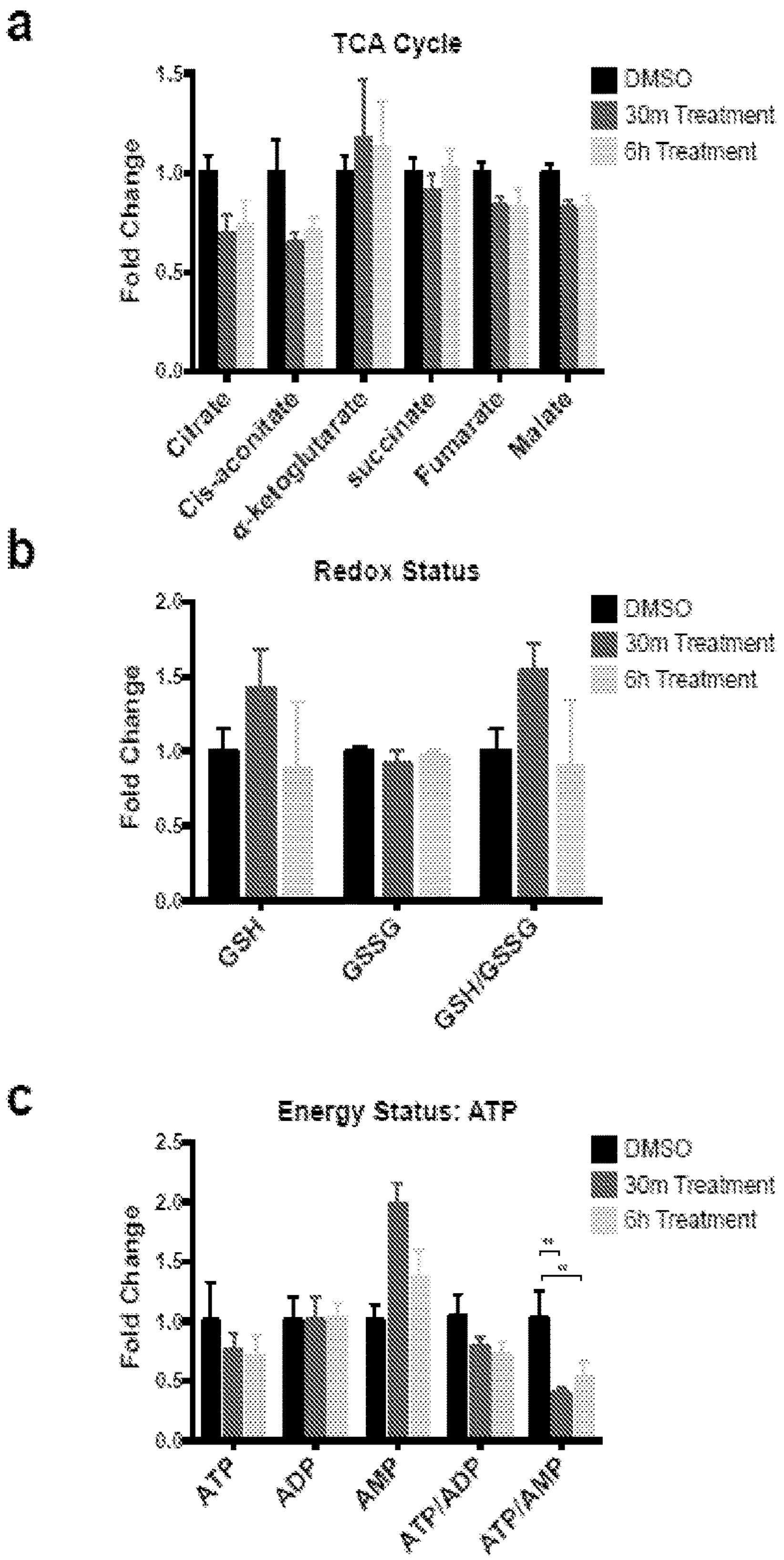

To understand the metabolic impact of GLUT inhibition by RgA, the steady-state levels of 272 metabolites was determined using LC/MS, Liu et al, *Anal. Chem.* 2014, 86, 2175-2184, in MCF-7 cells upon treatment with RgA for 30 min and 6 h, respectively. As shown in FIG. 4A, the most significant metabolic changes caused by RgA are related to glycolysis. Specifically, there were significant decreases in three upper glycolytic intermediates including glucose-6-phosphate (G6P), fructose 1,6-bisphosphate (F1,6-BP) and dihydroxyacetone phosphate (DHAP), and three key pentose phosphate pathway intermediates including 6-phosphogluconic acid (6PGA), ribose 5-phosphate (R5P), and erythrose-4-phosphate (E4P) (FIG. 4A and FIG. 4B). In contrast, the TCA cycle and redox status were not significantly affected by RgA treatment of MCF-7 cells ($p>0.001$) (FIG. 15). Together, these results suggested that metabolic effects of RgA were due almost exclusively to the inhibition of glucose uptake.

A major consequence of inhibition of GLUT is the decrease in the level of cellular ATP and the corresponding increase in the AMP/ATP ratio, which was indeed observed upon treatment of MCF-7 cells with RgA (FIG. 15). The increase in AMP/ATP ratio, in turn, is expected to activate AMPK, leading to the inhibition of the mTOR signaling pathway. Liu et al., *Mol. Cancer Ther.* 2012, 11, 1672-1682; Head et al., *ACS Chem. Biol.* 2017, 12, 174-182. The effect of RgA on AMPK and mTOR activity in MCF-7 cells was therefore determined. RgA activated AMPK and inhibited mTOR activity in both time- and dose-dependent manners (FIG. 4C). These results suggested that AMPK was likely to act as the key link between the upper glycolysis inhibition and subsequent mTOR pathway inhibition.

Figure 5:
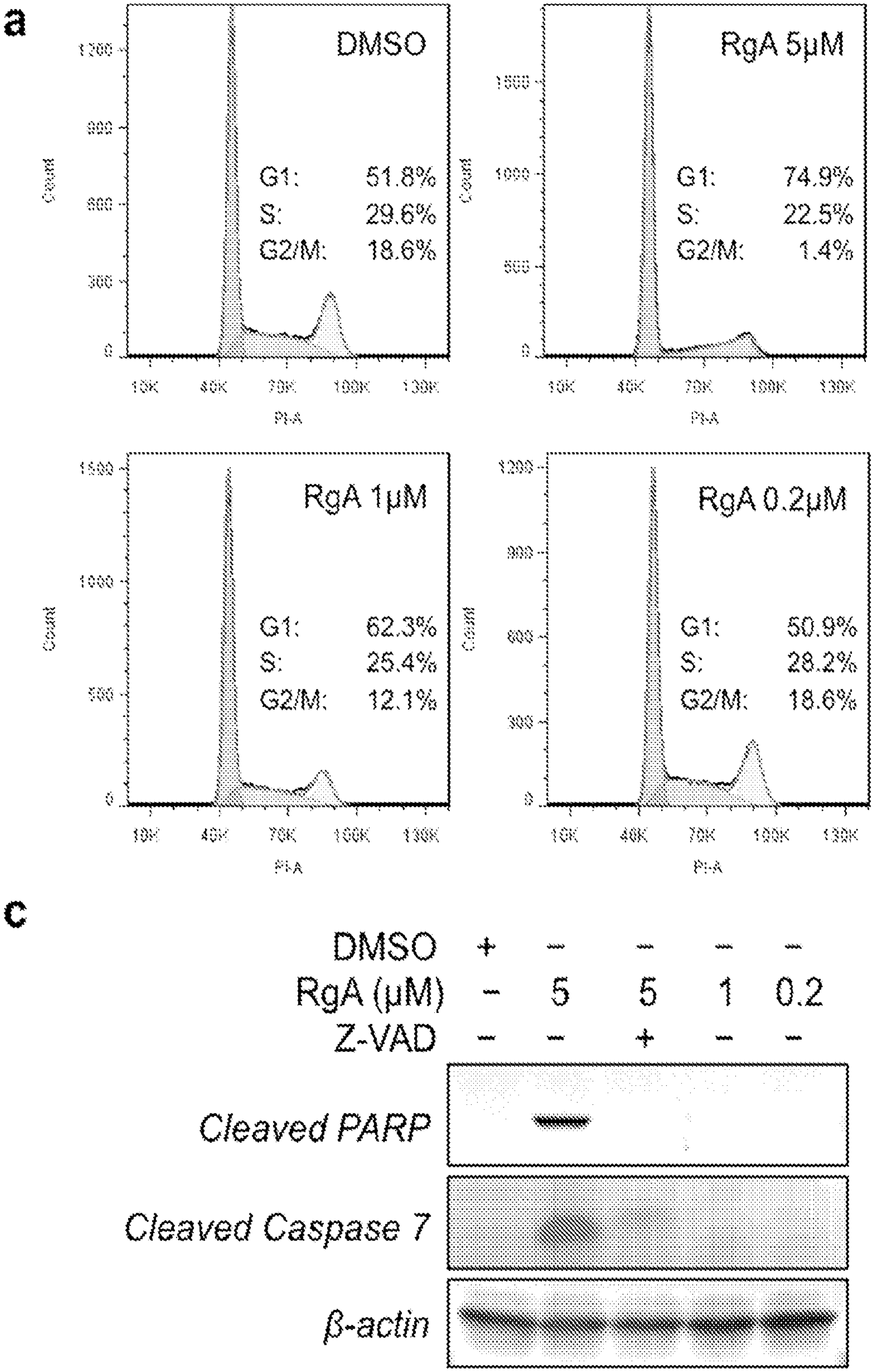
Figure 5:
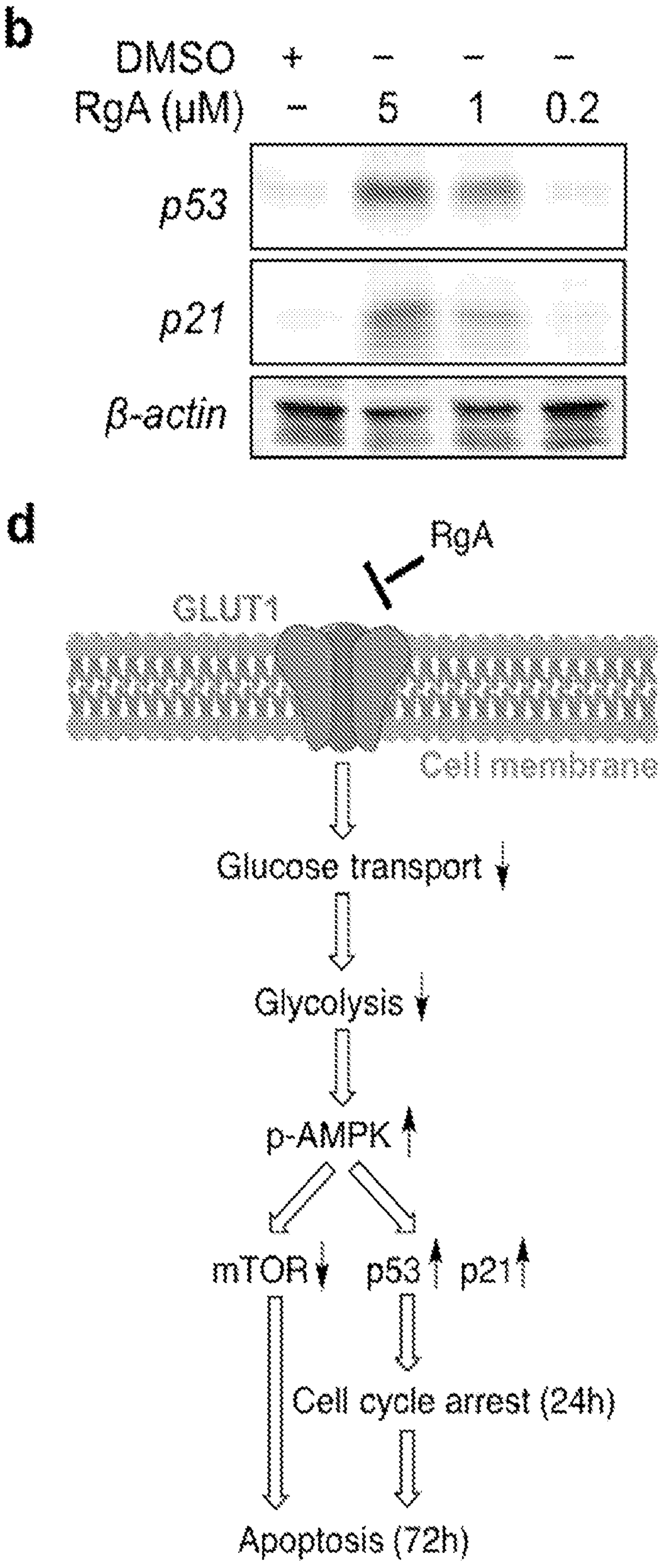

The effects of RgA on cell growth, survival, and cell death was then determined. Cell cycle analysis revealed that treatment of MCF-7 cells with RgA for 24 h led to G1 cell cycle arrest (FIG. 5A). Treatment with 5 μM of RgA caused an increase in G1 phase by approximately 23% in comparison to control and approximately 7% and 17% decreases in cells in S and G2/M phases, respectively. The induction in G1 phase cell cycle arrest by RgA is dose-dependent (FIG. 5A, FIG. 16). AMPK-activation has been shown to activate p53 and cell cycle inhibitor p21 to cause G1 cell cycle arrest. Jones and Thompson, *Genes Dev.* 2009, 23, 537-548. As expected, 24-h treatment with RgA led to activation of both p53 and p21 in a dose-dependent manner (FIG. 5*b*). Prolonged treatment of MCF-7, which is deficient in caspase 3, with 5 μM of RgA for 72 h resulted in poly(ADP-ribose) polymerase (PARP) and caspase 7 cleavage that was inhibited by cotreatment with the pancaspase inhibitor Z-VAD (FIG. 5C), indicative of apoptosis. The $IC_{50}$ values of RgA against several human cancer cell lines also was determined using the alamar blue cell proliferation assay. RgA dose-dependently inhibited proliferation of all the cancer cell lines tested, including the lung cancer cell line A549 and two breast cancer cell lines HCC1954 and MCF-7 (FIG. 6A), with $IC_{50}$ values ranging from 87 to 281 nM (Table 3), validating the antiproliferative activity of RgA.

Taken together, these data demonstrated that RgA treatment led to inhibition of glucose transport and glycolysis, activation of AMPK, inhibition of mTOR, and activation of p53 and p21, which culminated in G1 cell cycle arrest and apoptosis (FIG. 5D). Having demonstrated the anti-proliferative and apoptosis-inducing effects of RgA in vitro, whether RgA was capable of blocking tumor xenograft growth in vivo was determined. Given that RgA inhibited multiple isoforms of GLUTs, including GLUT1, 3, and 4, it raised the question of whether animals could tolerate RgA. As breast cancer cell lines are more sensitive to RgA than other cell lines (FIG. 6A and Table 3), the anti-breast cancer activity of RgA in vivo was assessed. Two breast cancer cell lines were selected for the xenograft experiment-MCF-7, an ER+, HER2− line, and HCC1954, an ER−, HER2+ breast line. NSG mice bearing MCF-7 tumors were given daily vehicle or RgA at a dose of 2 mg/kg for 38 days. Compared to vehicle control group, RgA treatment significantly delayed the xenograft growth of MCF-7 cells (FIG. 6B) with tumor volume indexes on day 38 being 2.84 vs. 1.70 between vehicle- and RgA-treatment groups. In addition, RgA treatment significantly decreased tumor weight from 454 mg (vehicle group) to 285 mg (treatment group) (FIG. 6C). Similarly, daily intraperitoneal injection of RgA at 2 mg/kg also effectively inhibited HCC1954 xenograft growth in nude mice (FIG. 17) with tumor volume indexes on day 38 of 26.14 vs. 12.97 between vehicle and RgA treatment groups. Importantly, no significant weight loss or any signs of adverse effects in animals receiving RgA were observed during the course of the experiments (FIG. 6D and FIG. 17), suggesting RgA at the efficacious dose was well tolerated in mice.

1.3 Materials and Methods

1.3.1. Biology

1.3.1.1 Biological Reagents

MCF-7, HCC1954, A549, Jurkat T, PANC 10.05, HeLa, RKO and HEK 293T cells were sourced from ATCC and were not further authenticated. DLD1 and its GLUT1 knockout cells were provided by Dr. Bert Vogelstein at Johns Hopkins University School of Medicine. Stable GLUT1, GLUT3, and GLUT4 overexpressing HEK 293T cells were generated by lentiviral infection of HEK 293T Null cells and were authenticated by western blot (FIG. 10). Human red blood cells were obtained from Fisher Scientific (Cat #: 50-643-497). Roswell Park Memorial Institute (RPMI) 1640 and Dulbecco's modified Eagle's medium (DMEM) media were purchased from Fisher Scientific (Cat #: 11875119 and Cat #: 11885092). 2-deoxy-D-[3H] glucose and 3-O-methyl-D-[3H] glucose were purchased from Perkin Elmer (Cat #: NET549 and Cat #: NET379). Streptavidin agarose beads were purchased from ThermoFisher Scientific (Cat #: 20359). Antibodies anti-GLUT1, anti-GLUT4, anti-p-AMPK, anti-AMPK, anti-p-S6K, anti-cleaved PARP, and anti-cleaved Caspase7 were purchased from Cell Signaling Technology (Cat #: 12939, 2213, 2535, 2532, 9205, 9541, 8438). Antibodies anti-GLUT3 anti-p21, antip53, and β-actin-HRP were purchased from Abcam (Cat #: ab15311, ab109199) and Santa Cruz Biotechnology (Cat #: sc-126, sc-47778), respectively.

1.3.1.2 Cell Culture

All cells were grown at 37° C. with 5% $CO_2$ in a humidified environment. MCF-7, A549, HeLa, RKO, HEK 293T, and DLD1 cells were cultured in DMEM supplemented with 10% (v/v) FBS, 50 U/mL penicillin, and 50 μg/mL streptomycin. Jurkat T, PANC10.05, and HCC1954 cells were cultured in RPMI 1640 medium supplemented with 10% (v/v) FBS, 50 μg/mL streptomycin and 50 U/ml penicillin. The cultures were checked periodically and found to be free of mycoplasma contamination.

1.3.1.3 Surface Chemistry Fabrication

The amine substrates (Arrayit, SMM) were immerged in a mixture of 2-bromoisobutyryl bromide (BIBB, 0.1 mM, as initiator) and propionyl bromide (10 mM, as horizontal spacer) with triethylamine (15 mM) in DCM for 4 hours. A degassed polymerization reaction mixture, containing copper (II) chloride dihydrate ($CuCl_2$, 4 mmol), 2,2'-bipyridine (2 mmol), 75 mmol monomers mixture of 2-(dimethylamino)ethyl methacrylate (DMAEMA) and poly(ethylene glycol) methacrylate (PEGMA Mn 360) in 500 mL Milli-Q/MeOH, was mixed with freshly made ascorbic acid (4 mmol). The mixture was applied to 50 slides for 6 hours under the argon atmosphere for the surface-initiated polymerization. A gradient ratio of PEGMA and DMAEMA was set, including 10:0, 8:2, 5:5, 2:8 and 0:10 for an optimization purpose. The terminals of the brushes were further functionalized by N,N'-disuccinimidyl carbonate (DSC, 10 mM) and 4-dimethylaminopyridine (DMAP,10 mM) in DMF overnight to form succinimidyl carbonate intermediate, and, successively, diazirine linker 1 (10 mM) and N,Ndiisopropylethylamine (DIPEA, 50 mM) in DMF for 2 hours to couple the photoaffinity linker in dark at room temperature. At the end, the substrates were immerged in a 50 mM ethanolamine in DMF to block the residual carboxylic moiety. The slides were thoroughly washed by DMF, EtOH and DCM and dried in a fuming cupboard and ready for spotting.

1.3.1.4 Small Molecule Microarray Spotting 10 mM of rapafucins in DMSO from the library were spotted onto the slides with a high-precision microarrayer (Nanoprint, Arrayit, CA) for a desired pattern in dark, which was loaded with 16 100-μm diameter micro-spotting pins. The pin heads were thoroughly washed and sonicated in ethanol and dried for 4 times under a compassed air between each sample loading. After overnight evaporation, the slides were exposed to 365-nm wavelength UV irradiation for 4 $J/cm^2$ by CL-1000L UV crosslinker (UVP, CA) for rapafucins covalent immobilization. The slides were ultrasonic cleaned successively in DCM, MeOH and Milli-Q water and stored in a −20° C. freezer.

1.3.1.5 Over-Expression of GLUT1, GLUT3, and GLUT4 in HEK293T

The full-length human SLC2A1, SLC2A3, and SLC2A4 genes were PCR amplified and inserted into pLenti6M vector 2. The cloned genes were confirmed not to contain any spurious mutations by sequencing the full length of the cloned inserts. The gene products were then transfected into HEK293T cells with pSPAX2 and pMD2G using lipofectamine 2000 and lentiviruses were harvested after 72 h. HEK293T cells were infected with the corresponding lentivirus and cells stably expressing GLUT1, GLUT3, and GLUT4 were selected with 10 g/mL blasticidin for two weeks and maintained at the same concentration of antibiotic for culture.

1.3.1.6 Affinity Pulldown with Biotinylated RgA.

GLUT1 or other isoforms overexpression HEK293T cells were washed once in buffer A (10 mM Tris-HCl, 150 mM KCl, 5 mM $MgCl_2$, 1 mM EGTA, pH 7.4). To extract GLUT1 or isoforms protein, cells were mixed in buffer C (10 mM Tris-HCl, 150 mM KCl, 5 mM $MgCl_2$, 1% DDM, 5% glycerol, 1 mM EGTA, protease inhibitor, pH 7.4) and incubated on ice for 1 h with frequent mixing. The supernatant was collected by centrifugation at 17,000 g for 10 min at 4° C., and then diluted four-fold in buffer A plus 5% glycerol to reduce the concentration of DDM. The diluted supernatant was quantified by protein assay kit and pre-incubated with streptavidin agarose beads at 4° C. for 30 min to remove the endogenous streptavidin-binding proteins. The supernatant was collected by centrifugation at 2,000 rpm for 1 min at 4° C., and diluted to 10 mg/mL for pull-down experiment. For a typical biotin pull- down reaction, 300 μL of supernatant was pretreated with competitor or equal volume of DMSO (as noted hereinabove) for 30 min, before the addition of RgA biotin probe or DMSO (as noted hereinabove). After incubation at 4° C. for 1 h with frequent mixing, 30 μL of streptavidin agarose beads in buffer A was added, and incubation was continued for 2 h. The agarose beads were precipitated by centrifugation and washed three times with 0.8 mL of buffer A and 0.05% DDM. The washed streptavidin agarose beads was then resuspended in 50 μL of 2×SDS sample buffer, heated at 100° C. for 5 min and centrifuged for 2 min. The supernatant was subjected to SDS-PAGE followed by western blot.

1.3.1.7 Microarray Assay

The slides were blocked by 5% BSA solution in buffer A (10 mM Tris-HCl, 150 mM KCl, 5 mM $MgCl_2$, 1 mM EGTA, pH 7.4) for 1 hour. In the optimization experiments, the slides were incubated with 50 nM purified recombinant FKBP12 for 1 hour, while in the GLUT1 screening, 10 mg/mL of cell lysate containing DDM-solubilized GLUT1 from GLUT1 overexpressed HEK293T was incubated for 1 hour. Successively, primary antibody and CY5 labeled secondary antibody were added for 1 hour. The chips were washed in buffer A for 5 mins 3 times after the sample and antibodies incubation. After centrifugation, the dried chips were scanned by a microarray scanner (Genepix, US) at 635-nm wavelength. The final result was analyzed by GenePix software.

1.3.1.8 Western Blot Analysis

For western blot analysis, cells were harvested and lysed by RIPA buffer plus protease inhibitor. Cell lysates or samples from pull-down experiment were subjected to SDS/PAGE and then transferred to a nitrocellulose membrane. Membranes were first blocked in 5% (wt/vol) BSA in Tris-buffered saline plus 0.1% Tween 20 (TBST) at room temperature for 30 min and incubated with primary antibodies at 4° C. for overnight. Membranes were then washed three times with TBST and incubated with secondary antibodies at room temperature for another 1 h. Membranes were washed with TBST three times again and incubated with ECL substrate for 1 min at room temperature. Pictures were captured using a GeneSys Image Station.

1.3.1.9 Measurement of $K_d$ Value for RgA

The estimation of $K_d$ value for RgA was determined with the biotin probe competition binding assay. The assay is similar with previous biotinylated RgA affinity pulldown except that the supernatant was incubated with increasing concentrations of RgA before adding 100 nM RgA biotin probe. After western blot, band intensities were quantified by densitometry analysis using Image J software. The assay was repeated three times. GraphPad Prism (v4.03) software was used to determine apparent Kd value for RgA using a nonlinear regression.

1.3.1.10 2-deoxy-D-[3H] glucose ([3H]-2DG) Uptake Assay

The inhibitory activity of compounds on glucose transport was analyzed by measuring the cell uptake of [3H]-2DG as previously described. Ulanovskaya et al., *Chem. Biol.* 2011, 18, 222-230. Briefly, cells were washed twice and incubated in low-glucose medium for 10 min. Cells were added drugs and incubated for another 10 min before adding [3H]-2DG. After 10 min incubation with [3H]-2DG, cells were washed twice and lysed with 0.2 N NaOH plus 0.2% SDS. The cell lysate was transferred to a new tube containing 1 mL of optiphase supermix. Glucose uptake was quantified with a scintillation counter.

1.3.1.11 Alamar Blue Cell Viability Assay

Cells were seeded into a 96-well plate (Costar) in 180 μL culture media. After an overnight recovery, drugs were added and incubated for 72 h. After drug incubation, cells were added with 20 μL of alamar blue reagent and the plates were incubated at 37° C. for 6 h before reading the fluorescence (544 nm Ex/590 nm Em) with a plate reader. GraphPad Prism (v4.03) software was used to determine $IC_{50}$ values using a four parameter logistic regression.

1.3.1.12 Metabolite Extraction and Analysis

MCF-7 Cells were seeded into 6-well plate at a density of $5\times10^5$ cells per well, allowed to recover overnight and subsequently treated with RgA or vehicle control for 30 min and 6 h, respectively. Metabolites were extracted and analyzed as previously described. Liu et al., *Anal. Chem.* 2014, 86, 2175-2184.

1.3.1.13 Cell Cycle Analysis

MCF-7 cells were seeded at $5\times10^5$ cells/15 cm dish, allowed to recover overnight and subsequently treated with drugs or vehicle control for 24 h. Media was then collected and set aside. Cells were washed with PBS, trypsinized, combined with set aside media, pelleted at 500×g and then washed with 10 mL PBS followed by another 500×g spin. The pellet was resuspended in 0.5 mL PBS and added dropwise using a Pasteur pipette to 2 mL 75% ethanol in a 5 mL polystyrene tube being slowly agitated by a vortex. The cells were stored at 4° C. until staining. To do so, cells were pelleted at 500×g, resuspended in 5 mL PBS, rested for 60 seconds, pelleted again and washed by 5 mL PBS. The cell pellet was then resuspended in 0.5 mL staining solution (0.1% Triton-X-100, 0.2 mg/mL DNase free RNase A, and 0.02 mg/mL propidium iodide). Cells were allowed to stain for 30 min prior for analysis. Propidium iodide incorporation was measured using a FACSCalibur. The percentage of cells in each cell cycle stage was determined with FlowJo (v7.5.5) using a Watson analysis.

1.3.1.14 In Vivo Breast Cancer Xenograft Assays

All animal studies were conducted in compliance with all relevant ethical regulations set forth by the Johns Hopkins University Animal Care and Use Committee (ACUC). Female mice aged 4-6 weeks and weighing 18-22 g were maintained in a pathogen-free facility at Johns Hopkins Medical Institutions and cared for according to National Institutes of Health guidelines and under a protocol approved by the Johns Hopkins University Animal Care Committee. For the xenograft experiment of MCF-7, 17β-estradiol pellets (0.72 mg per pellet, 60-day release, Innovative Research of America, FL) were implanted at 5 days prior to tumor cell injection. Approximately 5 million MCF-7 cells were implanted subcutaneously into NSG mice (n=6 per group, NSG, The Jackson Laboratory). For the xenograft experiment of HCC1954, approximately 2 million cells were implanted subcutaneously into athymic nude mice (n=6 per group, NCr-nu/nu, Charles River). After tumors became palpable, the mice bearing MCF-7 and HCC1954 tumors were treated with either vehicle (saline with 5% PEG400, 5% Tween80 and 5% DMSO) or RgA via intraperitoneal injection every day. The tumor volume was measured periodically using a Vernier caliper and calculated according to the modified ellipsoid formula: tumor volume ($mm^3$)=(short axis)$^2$×(long axis)×π/6. After 30 days of treatment, the mice were killed, and the tumor tissues were extracted and stored in 10% formalin solution for future use.

1.3.2. Chemistry 1.3.2.1 General Experimental for Synthesis 1.3.2.1.1 Synthetic Reagents Piperidine, N,N-diisopropylethylamine (DIPEA) were purchased from Alfa Aesar. Anhydrous pyridine was purchased from Acros. Solid support resin with 2-chlorotrityl chloride (Cat #: 03498) was purchased from Chem-Impex. HATU was purchased from ChemImpex. Fmoc protected amino acid building blocks were purchased from ChemImpex, Novabiochem or GL Biochem. Iodoacetyl-PEG2-biotin (Cat #: 21334) was purchased from Thermo Fisher. Dichloromethane (CH2Cl2), methanol (MeOH), hexanes, ethyl acetate (EtOAc), 1,2-dichloroethane (DCE, anhydrous), N,N'-dimethylformamide (DMF, anhydrous), CC14, methylamine (33%, methanol), Hoveyda-Grubbs catalyst 2nd generation, 1,3-propanedithiol, TBAF (1 M in THF) and all the other chemical reagents were purchased from Sigma-Aldrich.

1.3.2.1.2 Instruments for Synthesis and Purification

NMR spectra were recorded with Burker-400 and -500. High performance liquid chromatographic analyses were performed with Agilent LC-MS system (Agilent 1260 series, mass detector 6120 quadrupole). Orbital shaking for solid-phase reactions was performed on a Mettler-Toledo Bohdan MiniBlock system for 96 tubes (30-200 mg resin in SiliCycle tubes) or a VWR Mini Shaker (0.2-2 g resin in a plastic syringe with a fritted disc). Reagents were added with an adjustable Rainin 8-channel pipette for the MiniBlock system. Microwave reactions were performed with a Biotage Initiator Plus or Multiwave Pro with silicon carbide 24-well blocks from Anton Parr. Compound purification at 0.05-50 g scale was performed with Teledyne Isco CombiFlash Rf 200 or Biotage Isolera One systems followed by a Heidolph rotary evaporator.

1.3.2.1.3 General Procedures: Solid-Phase Peptide Synthesis (SPPS), Microwave-Assisted RCM Reaction, and Macrocycle Purification Protocol See Guo et al., *Nat. Chem.* 2019, 11, 254-263 for the general procedures.

1.3.2.1.4 FKBD Synthesis and Preparation of Cis-C6 Linker Conjugated Resin

See Guo et al., *Nat. Chem.* 2019, 11, 254-263 for the synthesis of FKBD and the preparation of cis-C6 linker conjugated resin.

1.3.2.2 Syntheses of Rapafucin JW11-D2 (RgA) and its Biotinylated Probe (Biotin-RgA)

Scheme 1. Synthetic route for rapafucin JW11-Ds (RgA) and its biotinylate probe.
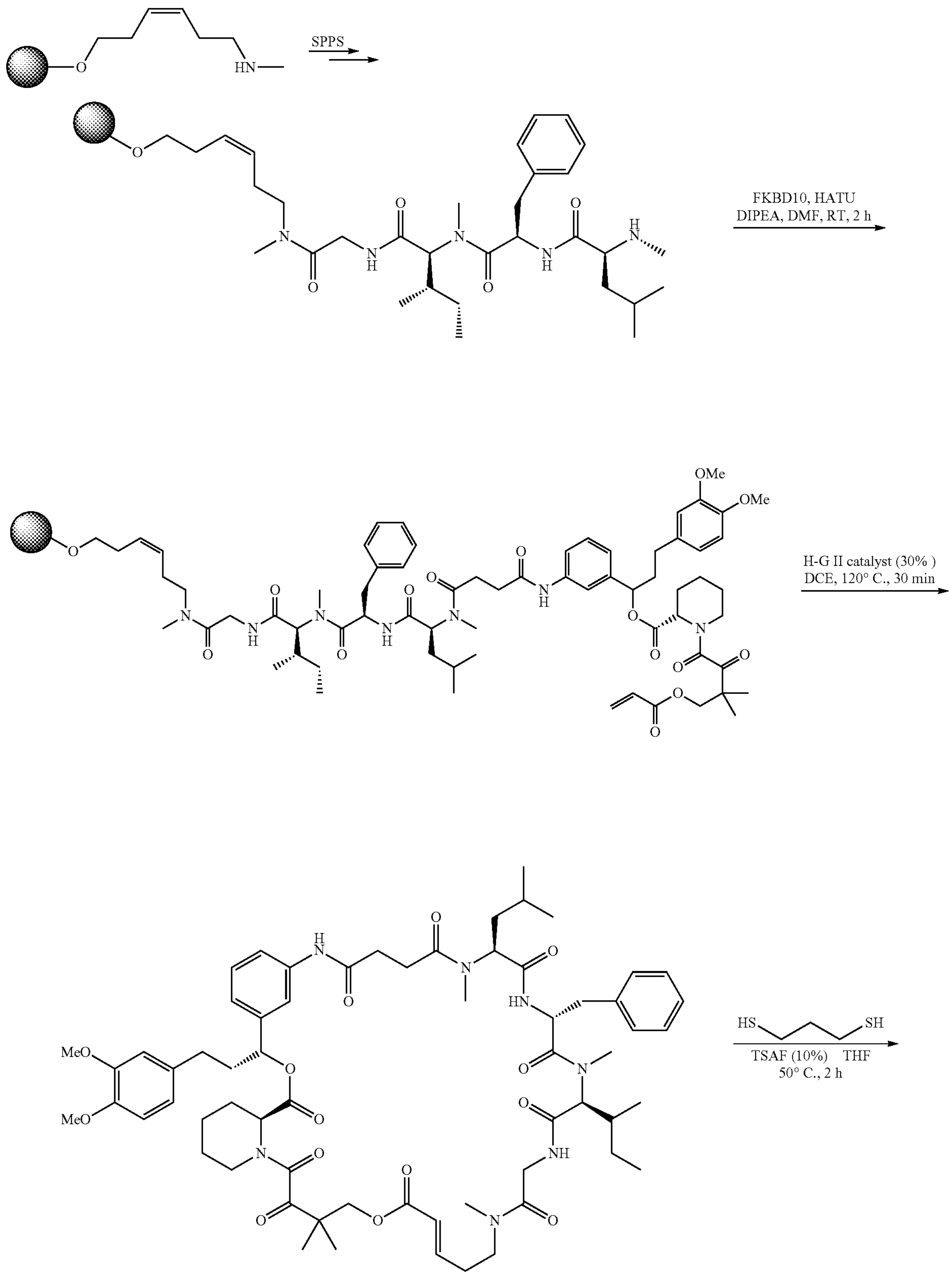
JW11-D2 (RgA)

-continued
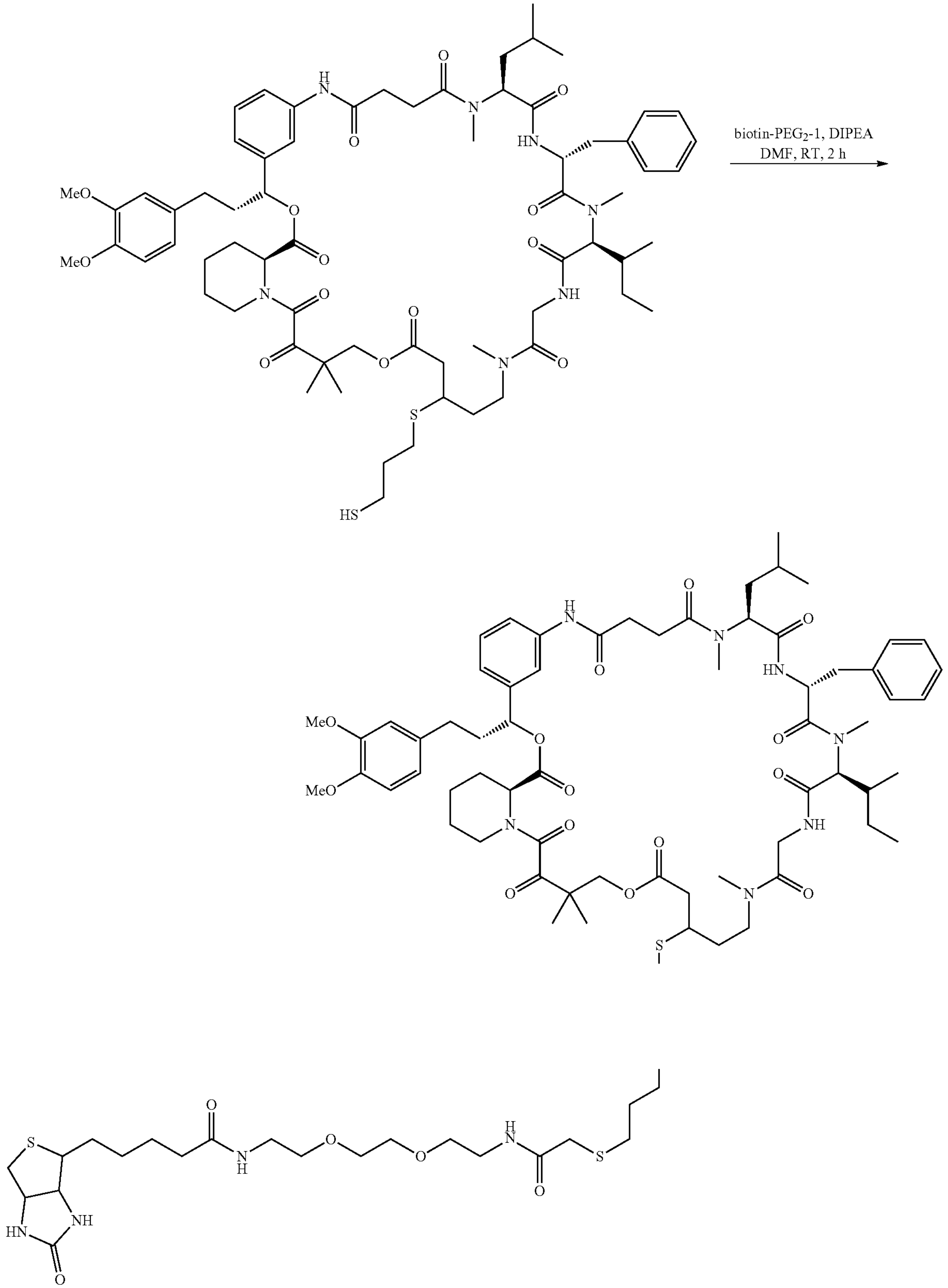
Biotin-JW11-D2
(Biotin-RgA)

-continued

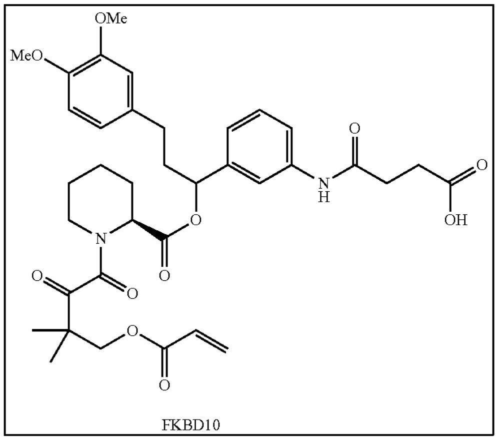

FKBD10

1.3.2.2.1 Synthesis of JW11-D2 (RgA)

Fmoc protected glycine, N-methyl isoleucine, phenylalanine, N-methyl isoleucine, D-leucine and FKBD10 were coupled in order on to cis-C6 linker conjugated beads (General Procedure A) before microwave-assisted RCM reaction (General Procedure B). Silica gel purification method was followed in General Procedure C to yield ~45% JW11-D2 at ~50 mg scale. 1H NMR (500 MHZ, CDCl3) δ 9.03 (s, 1H), 7.90 (s, 1H), 7.26-7.16 (m, 6H), 7.16-7.08 (m, 1H), 7.08-6.96 (m, 1H), 6.84-6.73 (m, 1H), 6.73-6.61 (m, 2H), 5.82-5.69 (m, 1H), 5.26 (d, J=5.4 Hz, 1H), 5.18-5.04 (m, 1H), 4.92-4.79 (m, 1H), 4.79-4.56 (m, 1H), 4.36-4.26 (m, 1H), 4.26-4.14 (m, 2H), 3.85 (s, 6H for 2 OCH3 groups), 3.48-3.37 (m, 1H), 3.27-3.14 (m, 2H), 2.99-2.90 (m, 2H), 2.87 (s, 3H), 2.77 (s, 3H), 2.68 (s, 3H), 2.64-2.52 (m, 4H), 2.38-2.17 (m, 4H), 2.13-1.89 (m, 4H), 1.79-1.54 (m, 3H), 1.35 (s, 3H), 1.30 (s, 3H), 1.28-1.19 (m, 4H), 0.95-0.89 (m, 3H), 0.88 (d, J=6.6 Hz, 3H), 0.83 (d, J=6.4 Hz, 3H), 0.78 (d, J=4.3 Hz, 3H).

1.3.2.2.2 Synthesis of Biotinylated JW11-D2 (Biotin-RgA)

11.8 mg JW11-D2 (0.010 mmol) was added into a 5 mL vial in 50 μL CH2Cl2 and stirred with 10.8 mg propanedithiol (0.10 mmol) and 0.20 mL TBAF (1 M in THF). After all rapaglutacin was dissolved, the reaction vessel was sealed and the reaction mixture was heated to 50° C. and stirred for 2 h. The reaction mixture was then dried with a rotary evaporator and co-evaporated twice to get rid of most of the excess propanedithiol. 19.1 mg iodoacetyl-PEG2-biotin (0.050 mmol), 17.4 μL DIPEA (0.10 mmol) and 0.20 mL DMF were added into the flask and stirred for 2 h at RT. The crude biotinylated probe was purified by silica gel column (MeOH in $CH_2Cl_2$: 0~10%). 2.5 mg biotinylated JW11-D2 (biotin-RgA) was obtained (15%).

1.4 Summary

In summary, to facilitate the screening of the rapafucin libraries against new protein targets, a microarray platform was developed by immobilizing rapafucins on a chip surface. Using an optimized 3D microarray with a total of 3,918 rapafucins on a single chip, cell lysates containing stably expressed GLUT1 were screened. Several hits were identified, two of which were confirmed as GLUT1 inhibitor in an orthogonal assay. The most potent inhibitor, named rapaglutin A (RgA), inhibited GLUT1, as well as GLUT3 and GLUT4, with an $IC_{50}$ value of low nanomolar for GLUT1. It was demonstrated that RgA inhibited glycolysis and ATP biogenesis, causing activation of AMPK, inhibition of mTOR, and induction of cell cycle arrest and apoptosis. RgA also inhibited the growth of tumor xenografts of breast cancer cells in vivo without obvious side effects. Using the newly developed 3D rapafucin microarrays, a successful screen against a multi-pass trans-membrane protein target was conducted for the first time. It will be interesting to screen the rapafucin microarrays against other types of multi-pass membrane proteins ranging from GPCRs to ion channels.

Example 2

3D Ethacrynic Acid Surface

In other embodiments, the presently disclosed subject matter provides a 3D microarray structure in which ethacrynic acid (EA) is covalently coupled, which can interact with glutathione S-transferase (GST), and can provide a surface for oriental protein immobilization.

Ethacrynic acid (EA), the structure of which is provided immediately herein below:

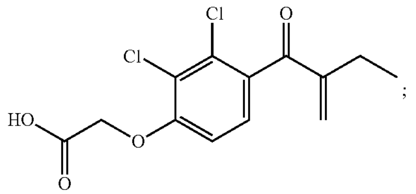 [SMILES: C=C(CC)C(=O)c1ccc(OCC(=O)O)c(Cl)c1Cl]

has been shown to produce competitive inhibition with respect to CDNB and non-competitive inhibition with respect to GSH. EA-GSH conjugation also was proved to be an enzyme inhibitor. EA can covalently bind to GST as a non-substrate ligand. In one study, a substantial proportion (13.5%) of ethacrynic acid bound to the glutathione S-transferases was bond covalently. Yamada and Kaplowitz, Biochemical Pharmacology, 1980, 29, 1205-1208. Owing to the chemical nature of the covalent binding (Michael addition), this reaction should be reversible. Indeed, full restoration of the catalytic activity of GST P1-1 inactivated by covalently-bound EA was reached in about 125 h by incubation with an excess of 10 mM glutathione.

Referring now to FIG. 21, the EA linker can be applied to a surface initiated polymerization (SIP) 3D surface. Extensive experiments were conducted to optimize the initiator density and to optimize the ratio of the poly(ethylene glycol) methacrylate (PEGMA) and 2-(Dimethylamino)ethyl methacrylate (DMAEMA) co-polymer. FIG. 22 shows one embodiment of optimizing the horizontal density by controlling the initiator density with a spacer. FIG. 23, FIG. 24, FIG. 25, and FIG. 26 show different aspects of horizontal density optimization.

Referring now to FIG. 27, experiments also were conducted to optimize the vertical density. It was found that a higher ratio of DMAEMA increases the immobilization amount in high concentration of protein. In one embodiment, a DMAEMA:PEGMA ratio of about 90:10 reached the highest response. It also was found that neutral pH, e.g., a pH around 7.2, produced better results. In other embodiments, other polymers, including, but not limited to, HEMA, MMA, DEAMA and more spacers with different ratios also could be used. In summary, representative parameters for 3D-EA surface chemistry preparation include: 1:100 initiator, a PEGMA-co-DMAEMA ratio of 1:9, about 4 hours polymerization, and overnight ethacrynic acid coupling. Representative printing conditions include: 2.5 μM protein (FKBP12) with 12.5 μM rapafucin individual fresh premixed, pH=7.4 in Tris-HCl, overnight immobilization, and avoid freezing cycles.

Example 3

Protein Microarray

Referring now to FIG. 28, is a schematic representation of a Huprot microarray on a 3D-EA surface. FIG. 29 is a comparison of the 2D-EA and 3D-EA surface for GST Ab probing with 293T cell lysate and then calcineurin AB probing (imaging data not shown). In this example, the 3D surface exhibits a 90% increase in response for anti-GST Ab detection and about a 260% increase in response for probing FKBP12:FK506 and calcineurin interaction by anti-calcineurin Ab.

Referring now to FIG. 30 is a comparison of a PATH surface and 3D-EA surface. In this example, since all protein on the protein microarray contains GST tag, anti-GST Ab were applied to probe the GST proteins immobilized on the surface. The 3D-EA surface exhibited a higher response than the PATH surface. The 3D-EA surface also exhibited a higher signal-to-noise ratio than the PATH surface.

The protein-protein interaction also was investigated for CRYBB2 as a representative example. CRYBB2 is known to be a protein of the eye lens and mutation leads to cataract. It also was described to be involved in axon and ovarian cells growth, but nothing with cancer. It overexpressed in African American breast, prostate and colorectal cancer, but there are no studies on the functional role of this gene in cancer. The inventors identified that this gene increase malignancy of breast cancer cells.

Briefly, the following protocol was used:

CDI huport chip, series 201703

3D PEGMA-PDMAMA surface with EA terminals.

Tris-HCl, with 2 mM Ca2+ and Mg2+, pH=7.5

Cells from 2 10 cm-diameter dishes, sonication

5% BSA

Lysate diluted into 6 mL

CRYBB2 antibody and secondary antibody premixed for one hour

Antibody applied with cover slip

Chip 1: lysate in BSA, CRYBB2 antibody, Cy5-labeled antibody

Chip 2: BSA, CRYBB2 antibody, Cy5-labeled antibody 20,000 proteins SNRs were calculated and compared.

Hits were only be considered when SNR on Chip 1 is high while the one on Chip 2 is low.

The number indicates the ratio between SNR (lysate) and SNR (negative)

Hits name may repeat for the reason of isomer.

FIG. 31, FIG. 32, FIG. 33, and FIG. 34 show representative results from this study.

Example 4

Small Molecule Induced Protein-Protein Interaction

Referring now to FIG. 35 is a photograph of a rapafucin microarray printing (real chip). FIG. 36 is a schematic depicting an FKBP12 displaying rapafucin microarray. FIG. 37 is a comparison between a PATH surface and a 3D-EA rapafucin microarray. For anti-GST antibody detection, the spot sizes on the 3D-EA surface are larger than those on the PATH surface. The intensity on the 3D-EA surface also is compared to that on the PATH surface (200-nm nitrocellulose film).

Referring now to FIG. 38, FKBP12 displaying rapafucin microarray and its screening on endogens mTOR streptavidin and Glut1, respectively, is illustrated. Rapamycin induced a specific binding between FKBP12 and mTOR. Biotinylated rapafucin induced a specific binding between FKBP12 and streptavidin. FK506 induced a specific binding between FKBP12 and calcineurin.

FIG. 39 also is a comparison between PATH surface and 3D-EA -rapafucin microarray using calcineurin. In this example, the intensity of FK506 is 10 times greater on the 3D-EA surface compared to on the PATH surface. E121112 and FKDP are significant hits on 3D-EA, but negative (or only 10% higher than negative) on PATH surface. A high background also was observed on the PATH surface.

FIG. 40 is a comparison between PATH and 3D-EA-rapafucin microarray for mTor. In this example, the intensity of rapamycin is 7 times greater on the 3D-EA surface than on the PATH surface. The negative spots are two-fold less on the 3D-EA surface compared to on the PATH surface. Also, the signal-to-noise ratio significantly improved on the 3D-EA surface relative to that on the PATH surface.

Referring now to FIG. 41, the following protocol was used:

C201:

1:1000 Anti-GST Ab, 3 ml, 1 h

1:1000 Cy5-Anti-M, 3 ml, 0.5 h

Tris buffer, $Ca^{2+}$

C202:

1:1000 Anti-FKBP12 Ab, 3 ml, 1 h

1:1000 Cy5-Anti-R, 3 ml, 0.5 h

Tris buffer, $Ca^{2+}$

C201:

1:1000 Anti-FKBP51 Ab, 3 ml, 1 h

1:1000 Cy5-Anti-R, 3 ml, 0.5 h

Tris buffer, $Ca^{2+}$

C201:

1:500 Anti-FKBP52 Ab, 3 ml, 1 h

1:1000 Cy5-Anti-G, 3 ml, 0.5 h

Tris buffer, $Ca^{2+}$

FIG. 42 is an example demonstrating mTOR detection. In this example, the following protocol was used:

C206 3D-EA-3 hours

293T Cell lysate 1 hours.

3 ml shacking

Tris ($Ca^{2+}$+I)

1:1000 mTOR Ab
1 hour
3 ml shacking
Tris ($Ca^{2+}$)
1:1000 $2^{nd}$ Rabbit
0.5 hour
3 ml shacking
Tris ($Ca^{2+}$)

In this example, the sensitivity of rapamycin spots slightly decrease due to the FKBP protein concentration decrease 50%, and droplet decrease 75%. The total protein amount per spot in 2nd is ⅛ of 1st rapafucin microarray.

FIG. 43 is an example of calcineurin detection. The following protocol was used:

C253 3D-EA-8 hours
293T Cell lysate
1 hours
3 ml shacking
Tris ($Ca^{2+}$+I)
1:1000 calcineurin Ab
1 hour.
3 ml shacking
Tris ($Ca^{2+}$)
1:1000 $2^{nd}$ Rabbit
0.5 hour
3 ml shacking
Tris ($Ca^{2+}$)

FIG. 44 is calcineurin results analysis. This analysis included 11 compounds: FKVP, FKAM, FKDVP, FKTHF, FKABT, FKTM, FKVAM, FKN4, FKDEA, FKSAS, FKDP and Zufeng 24 compounds, with blind screening, including original E121112, purified E121112, HPLC sections. Representative results included: Brandon Compounds: Only FKDP (12.5 μM) is positive to Calcineurin on chip screening. Others are negative. FKDP's signal is comparable to 0.1 uM FK506 group Zufeng Compounds: Only original E121112 (12.5 μM) is positive to Calcineurin. Signal is comparable to 0.1 uM FK506 group. All purified or HPLC sections of E121112 are negative on chip detection.

FIG. 45 shows a sensitivity evaluation by storage conditions. The parameters included 4° C. for 3 days as a beginning point, then −80° C. for one month, −20° C. for one month, and 4° C. for one month.

FIG. 46 shows another embodiment for a representative surface strategy including specifically covalently binding to halo-tag (34 kD), including a terminal chlorine of a reactive chloroalkane linker.

FIG. 45 is sensitivity evaluation by storage conditions; and

FIG. 46 is an embodiment of a surface strategy.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

O. Warburg, *Science* 1956, 124, 267-272.

N. Hay, *Nat. Rev. Cancer* 2016, 16, 635-649.

F. Schwartzenberg-Bar-Yoseph, M. Armoni, E. Karnieli, *Cancer Res.* 2004, 64, 2627-2633.

J. Yun, C. Rago, I. Cheong, R. Pagliarini, P. Angenendt, H. Rajagopalan, K. Schmidt, J. K. Willson, S. Markowitz, S. Zhou, L. A. Jr Diaz, V. E. Velculescu, C. Lengauer, K. W. Kinzler, B. Vogelstein, N. Papadppoulos, *Science,* 2009, 325, 1555-1559.

C. Chen, N. Pore, A. Behrooz, F. Ismail-Beigi, A. Maity, *J. Biol. Chem.* 2001, 276, 9519-9525.

X. Cao, L. Fang, S. Gibbs, Y. Huang, Z. Dai, P. Wen, X. Zheng, W. Sadee, D. Sun, *Cancer Chemother. Pharmacol.* 2007, 59, 495-505.

Y. Liu, Y. Cao, W. Zhang, S. Bergmeier, Y. Qian, H. Akbar, R. Colvin, J. Ding, L. Tong, S. Wu, J. Hines, X. Chen, *Mol. Cancer Ther.* 2012, 11, 1672-1682.

D. A. Chan, P. D. Sutphin, P. Nguyen, S. Turcotte, E. W. Lai, A. Banh, G. E. Reynolds, J. T. Chi, J. Wu, D. E. Solow-Cordero, M. Bonnet, J. U. Flanagan, D. M. Bouley, E. E. Graves, W. A. Denny, M. P. Hay, A. J. Giaccia, *Sci. Transl. Med.* 2011, 3, 94ra70.

W. Zhang, Y. Liu, X. Chen, S. C. Bergmeier, *Bioorg. Med. Chem. Lett.* 2010, 20, 2191-2194.

L. K. Gunnink, O. D. Alabi, B. D. Kuiper, S. M. Gunnink, S. J. Schuiteman, L. E. Strohbehn, K. E. Hamilton, K. E. Wrobel, L. L. Louters, *Biochimie* 2016, 125, 179-185.

T. E. Wood, S. Dalili, C. D. Simpson, R. Hurren, X. Mao, F. S. Saiz, M. Gronda, Y. Eberhard, M. D. Minden, P. J. Bilan, A. Klip, R. A. Batey, A. D. Schimmer, *Mol. Cancer Ther.* 2008, 7, 3546-3555.

L. G. Melstrom, M. R. Salabat, X. Z. Ding, B. M. Milam, M. Strouch, J. C. Pelling, D. J. Bentrem, *Pancreas* 2008, 37, 426-431.

J. C. Vera, A. M. Reyes, J. G. Carcamo, F. V. Velasquez, C. I. Rivas, R. H. Zhang, P. Strobel, R. Iribarren, H. I. Scher, J. C. Slebe, et al., *J. Biol. Chem.* 1996, 271, 8719-8724.

O. A. Ulanovskaya, J. Cui, S. J. Kron, S. A. Kozmin, *Chem. Biol.* 2011, 18, 222-230.

K. Kapoor, J. S. Finer-Moore, B. P. Pedersen, L. Caboni, A. Waight, R. C. Hillig, P. Bringmann, I. Heisler, T. Muller, H. Siebeneicher, R. M. Stroud, *Proc. Natl. Acad. Sci. USA* 2016, 113, 4711-4716.

B. J. DeBosch, M. R. Heitmeier, A. L. Mayer, C. B. Higgins, J. R. Crowley, T. E. Kraft, M. Chi, E. P. Newberry, Z. Chen, B. N. Finck, N. O. Davidson, K. E. Yarasheski, P. W. Hruz, K. H. Moley, *Sci. Signal* 2016, 9, ra21.

H. Siebeneicher, A. Cleve, H. Rehwinkel, R. Neuhaus, I. Heisler, T. Muller, M. Bauser, B. Buchmann, *ChemMedChem* 2016, 11, 2261-2271.

H. Yang, D. G. Rudge, J. D. Koos, B. Vaidialingam, H. J. Yang, N. P. Pavletich, *Nature* 2013, 497, 217-223.

J. P. Griffith, J. L. Kim, E. E. Kim, M. D. Sintchak, J. A. Thomson, M. J. Fitzgibbon, M. A. Fleming, P. R. Caron, K. Hsiao, M. A. Navia, *Cell* 1995, 82, 507-522.

C. R. Kissinger, H. E. Parge, D. R. Knighton, C. T. Lewis, L. A. Pelletier, A. Tempczyk, V. J. Kalish, K. D. Tucker, R. E. Showalter, E. W. Moomaw, et al., *Nature* 1995, 378, 641-644.

P. S. Marinec, L. Chen, K. J. Barr, M. W. Mutz, G. R. Crabtree, J. E. Gestwicki, *Proc. Natl. Acad. Sci. USA* 2009, 106, 1336-1341.

Z. Guo, S. Y. Hong, J. Wang, S. Rehan, W. Liu, H. Peng, M. Das, W. Li, S. Bhat, B. Peiffer, B. R. Ullman, C. M. Tse, Z. Tarmakova, C. Schiene-Fischer, G. Fischer, I. Coe, V. O. Paavilainen, Z. Sun, J. O. Liu, *Nat. Chem.* 2019, 11, 254-263.

Y. M. Foong, J. Fu, S. Q. Yao, M. Uttamchandani, *Curr. Opin. Chem. Biol.* 2012, 16, 234-242.

J. A. Hong, D. V. Neel, D. Wassaf, F. Caballero, A. N. Koehler, *Curr. Opin. Chem. Biol.* 2014, 18, 21-28.

M. Uttamchandani, S. Q. Yao, *Methods Mol. Biol.* 2017, 1518, 1-17.

N. Kanoh, S. Kumashiro, S. Simizu, Y. Kondoh, S. Hatakeyama, H. Tashiro, H. Osada, *Angew. Chem. Int. Ed. Engl.* 2003, 42, 5584-5587.

I. Miyazaki, S. Simizu, H. Okumura, S. Takagi, H. Osada, *Nat. Chem. Biol.* 2010, 6, 667-673.

R. Barbey, L. Lavanant, D. Paripovic, N. Schuwer, C. Sugnaux, S. Tugulu, H. A. Klok, *Chem. Rev.* 2009, 109, 5437-5527.

H. Ma, J. He, X. Liu, J. Gan, G. Jin, J. Zhou, *ACS Appl. Mater. Interfaces* 2010, 2, 3223-3230.

J. O. Zoppe, N. C. Ataman, P. Mocny, J. Wang, J. Moraes, H. A. Klok, *Chem. Rev.* 2017, 117, 1105-1318.

S. B. Lee, R. R. Koepsel, S. W. Morley, K. Matyjaszewski, Y. Sun, A. J. Russell, *Biomacromolecules* 2004, 5, 877-882.

M. Kawatani, H. Osada, *Medchemcomm* 2014, 5, 277-287.

A. L. Helgerson, A. Carruthers, *J. Biol. Chem.* 1987, 262, 5464-5475.

M. Mueckler, B. Thorens, *Mol. Aspects Med.* 2013, 34, 121-138.

B. Hellwig, H. G. Joost, *Mol. Pharmacol.* 1991, 40, 383-389.

B. E. Bierer, P. S. Mattila, R. F. Standaert, L. A. Herzenberg, S. J. Burakoff, G. Crabtree, S. L. Schreiber, *Proc. Natl. Acad. Sci. USA* 1990, 87, 9231-9235.

X. Liu, Z. Ser, J. W. Locasale, *Anal. Chem.* 2014, 86, 2175-2184.

S. A. Head, W. Q. Shi, E. J. Yang, B. A. Nacev, S. Y. Hong, K. K. Pasunooti, R. J. Li, J. S. Shim, J. O. Liu, *ACS Chem. Biol.* 2017, 12, 174-182.

R. G. Jones, C. B. Thompson, *Genes Dev.* 2009, 23, 537-548.

J. Heitman, N. R. Movva, M. N. Hall, *Science* 1991, 253, 905-909.

J. Liu, J. D. Farmer, W. S. Lane, J. Friedman, I. Weissman, S. L. Schreiber, *Cell* 1991, 66, 807-815.

F. Zhang, S. Bhat, S. B. Gabelli, X. Chen, M. S. Miller, B. A. Nacev, Y. L. Cheng, D. J. Meyers, K. Tenney, J. S. Shim, P. Crews, L. M. Amzel, D. Ma, J. O. Liu, *J. Med. Chem.* 2013, 56, 3996-4016.

T. Yamada and N. Kaplowitz, Biochemical Pharmacology, 1980, 29, 1205-1208.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A three-dimensional microarray comprising a surface-modified substrate-comprising a scaffold having the following molecular structure:

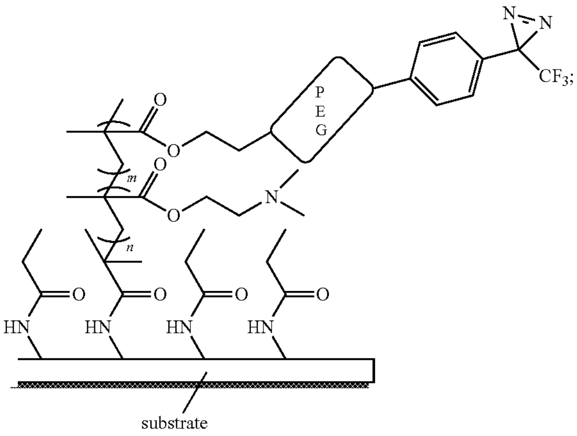

wherein m and n are each independently an integer from 1 to 1000.

2. The three-dimensional array of claim 1, further comprising a library of small molecules printed on one or more locations on the surface, wherein the library of small molecules are immobilized to the surface through photocross-linking to the diazirine functional groups.

3. A method for identifying a glucose transporter inhibitor, the method comprising contacting a three-dimensional microarray of claim 1 with one or more cells expressing a glucose transporter protein, wherein the glucose transporter protein binds to one or more rapafucins of the three-dimensional microarray, and detecting the bound glucose transporter protein.

4. The method of claim 3, wherein the glucose transporter protein is selected from GLUT1, GLUT3, and GLUT4.

5. The method of claim 4, wherein the glucose transporter protein is GLUT1.

* * * * *